United States Patent
Deshpande et al.

(10) Patent No.: US 12,133,917 B2
(45) Date of Patent: Nov. 5, 2024

(54) PEDIATRIC DOSAGE FORMS, METHODS OF MAKING AND USING

(71) Applicant: EIRGEN PHARMA LTD., Waterford (IE)

(72) Inventors: Praful Balavant Deshpande, Waterford (IE); Stephen James Quinlan, Waterford (IE); Marta Golec, Waterford (IE); John Gerard O'Brien, Waterford (IE); James Joseph McDonald, Waterford (IE); Reem Elamein Elsiddig, Waterford (IE); Ken O'Shea, Waterford (IE)

(73) Assignee: EIRGEN PHARMA LTD., Waterford (IE)

( * ) Notice: Subject to any disclaimer, the term of this patent is extended or adjusted under 35 U.S.C. 154(b) by 62 days.

(21) Appl. No.: 17/478,395

(22) Filed: Sep. 17, 2021

(65) Prior Publication Data

US 2022/0000783 A1    Jan. 6, 2022

Related U.S. Application Data

(63) Continuation of application No. 17/224,768, filed on Apr. 7, 2021, which is a continuation of application No. 16/869,273, filed on May 7, 2020, now Pat. No. 11,000,480, which is a continuation of application No. PCT/IB2019/057360, filed on Aug. 30, 2019.

(60) Provisional application No. 62/725,940, filed on Aug. 31, 2018.

(51) Int. Cl.
*A61K 9/16* (2006.01)
*A61K 9/00* (2006.01)
*A61K 31/592* (2006.01)
*A61K 31/593* (2006.01)

(52) U.S. Cl.
CPC .......... *A61K 9/1652* (2013.01); *A61K 9/0002* (2013.01); *A61K 9/0053* (2013.01); *A61K 9/1617* (2013.01); *A61K 9/1635* (2013.01); *A61K 9/1694* (2013.01); *A61K 31/592* (2013.01); *A61K 31/593* (2013.01)

(58) Field of Classification Search
None
See application file for complete search history.

(56) References Cited

U.S. PATENT DOCUMENTS

| | | |
|---|---|---|
| 4,729,895 A | 3/1988 | Makino et al. |
| 5,487,900 A | 1/1996 | Itoh et al. |
| 5,505,983 A | 4/1996 | Kamada |
| 5,614,513 A | 3/1997 | Knutson et al. |

(Continued)

FOREIGN PATENT DOCUMENTS

| | | |
|---|---|---|
| CL | 201700317 | 2/2017 |
| CL | 201701335 | 5/2017 |

(Continued)

OTHER PUBLICATIONS

CN108420797B—Google English Translation (Year: 2018).*

(Continued)

*Primary Examiner* — Kyung S Chang
(74) *Attorney, Agent, or Firm* — MARSHALL, GERSTEIN & BORUN LLP

(57) ABSTRACT

Pediatric and modified release dosage forms of vitamin D compounds, and methods of making and using the dosage forms, are disclosed.

30 Claims, 8 Drawing Sheets

(56) References Cited

U.S. PATENT DOCUMENTS

| | | |
|---|---|---|
| 8,207,149 B2 | 6/2012 | Tabash et al. |
| 9,861,644 B2 | 1/2018 | White et al. |
| 9,907,758 B2 | 3/2018 | Kaur et al. |
| 11,000,480 B2 | 5/2021 | Deshpande et al. |
| 2007/0104783 A1 | 5/2007 | Domb et al. |
| 2009/0176748 A1 | 7/2009 | Tabash et al. |
| 2009/0311316 A1 | 12/2009 | Bishop et al. |
| 2012/0213851 A1 | 8/2012 | Mahjour et al. |
| 2014/0349979 A1 | 11/2014 | White et al. |
| 2016/0008377 A1 | 1/2016 | Castor |
| 2016/0038514 A1* | 2/2016 | Petkovich ............ A61P 7/08 424/463 |
| 2020/0338006 A1 | 10/2020 | Deshpande et al. |

FOREIGN PATENT DOCUMENTS

| | | | | |
|---|---|---|---|---|
| CL | 201800739 | | 3/2018 | |
| CL | 201802734 | | 9/2018 | |
| CN | 101584683 | A | 11/2009 | |
| CN | 105246464 | A | 1/2016 | |
| CN | 108420797 | B * | 5/2022 | ........... A61K 31/593 |
| JP | H04-013625 | A | 1/1992 | |
| JP | H04-198129 | A | 7/1992 | |
| JP | 2009275007 | A | 11/2009 | |
| JP | 2011241150 | A | 12/2011 | |
| JP | 2015-509539 | A | 3/2015 | |
| JP | 2016-517430 | A | 6/2016 | |
| WO | WO-03/059358 | A1 | 7/2003 | |
| WO | WO-2012/047098 | A1 | 4/2012 | |
| WO | WO-2017/060320 | A1 | 4/2017 | |
| WO | WO-2017/182237 | A1 | 10/2017 | |

OTHER PUBLICATIONS

Office Action (English translation) from Chinese Application No. 2019800641834 dated Aug. 3, 2022.

International Search Report and Written Opinion from International Application No. PCT/IB2019/057360 dated Dec. 19, 2019.

Rayaldee (calcifediol) extended-release capsules, for oral use. Highlights of Prescribing Information, pp. 1-12, Jan. 2016.

Rayaldee, www.rxlist.com, (2016).

Notice of Reasons for Refusal for Japanese Patent Application No. 2021-510876, dated Aug. 1, 2023.

Shi et al., Preparation of chitosan/ethylcellulose complex microcapsule and its application in controlled release of Vitamin D2, Biomaterials, 23(23): 4469-4473 (Dec. 2002).

\* cited by examiner

PEDIATRIC DOSAGE FORMS, METHODS OF MAKING AND USING

CROSS REFERENCE TO RELATED APPLICATIONS

This is a continuation of U.S. application Ser. No. 17/224,768, filed Apr. 7, 2021, which is a continuation of U.S. application Ser. No. 16/869,273, filed May 7, 2020, which is a continuation of International Application PCT/1619/57360, filed Aug. 30, 2019, which claims the benefit under 35 U.S.C. § 119(e) of U.S. Provisional Patent Application Ser. No. 62/725,940 filed Aug. 31, 2018, the disclosures of which are hereby incorporated by reference herein.

BACKGROUND

Field of the Disclosure

The disclosure relates generally to dosage forms of vitamin D compounds, e.g. calcifediol, including forms suitable for pediatric use, and methods of making and using the same.

BRIEF DESCRIPTION OF RELATED TECHNOLOGY

Vitamin D compounds have traditionally been administered in immediate release formulations. More recently, some modified release dosage forms of vitamin D compounds have been described, e.g. in wax matrix form. The present disclosure relates to vitamin D preparations, including extended release preparations and those suitable for use in pediatric patient populations. Formulations for delivery of active vitamin D, analogs thereof, and prohormones thereof have been disclosed, including some extended release dosage forms. One such formulation is marketed in the United States under the brand name RAYALDEE® (calcifediol), a product which is approved to treat secondary hyperparathyroidism in stage 3 and 4 chronic kidney disease (CKD) patients. The prescribing information for this drug provides that the sustained release formulation for RAYALDEE® is a wax based extended release formulation of 25-hydroxyvitamin $D_3$.

SUMMARY

One aspect of the disclosure herein is a vitamin D formulation, comprising a vitamin D compound, optionally 25-hydroxyvitamin D or calcifediol, dispersed in a polymer composition. In embodiments, the formulation can be an extended release formulation, e.g. for oral use.

Another aspect of the disclosure herein is a vitamin D formulation, comprising a vitamin D compound, optionally 25-hydroxyvitamin D or calcifediol, embedded in a polymer network. The polymer can be water-insoluble, and optionally swellable. In embodiments, the formulation can be an extended release formulation, e.g. for oral use.

Another aspect of the disclosure herein is a spheronized pellet formulation comprising a vitamin D compound, optionally 25-hydroxyvitamin D or calcifediol, and a pharmaceutically acceptable excipient. In embodiments, the formulation can be an extended release formulation, e.g. for oral use.

Another aspect of the disclosure herein is an vitamin D formulation comprising a vitamin D compound, optionally 25-hydroxyvitamin D or calcifediol, dispersed in a fatty acid glyceride mixture. In embodiments, the formulation can be an extended release formulation, e.g. for oral use.

Another aspect of the disclosure herein is a nano/microparticle formulation comprising a vitamin D compound, optionally 25-hydroxyvitamin D or calcifediol, and a pharmaceutically acceptable excipient. In embodiments, the nano/microparticle formulation can provide extended release of the vitamin D compound, e.g. by using an extended release polymer as an excipient.

Another aspect of the disclosure herein is a lipid microparticle formulation comprising a vitamin D compound, optionally 25-hydroxyvitamin D or calcifediol, and a pharmaceutically acceptable lipid. In embodiments, the formulation can be an extended release formulation, e.g. for oral use.

Another aspect of the disclosure herein is a non-pareil seed formulation comprising a vitamin D compound, optionally 25-hydroxyvitamin D or calcifediol, and a pharmaceutically acceptable excipient. In embodiments, the formulation can be an extended release formulation, e.g. for oral use. In embodiments, the excipient can include an extended release polymer coating.

Another aspect of the disclosure herein is a pharmaceutical composition comprising a vitamin D compound, optionally 25-hydroxyvitamin D or calcifediol, and a pharmaceutically acceptable excipient selected from one or more excipients in the group of an absorption enhancer, a spheronizing aid, a water insoluble polymer, and a binder. In embodiments, the formulation can be an extended release formulation, e.g. for oral use.

Another aspect of the disclosure herein is a spray-congealed lipid vitamin D formulation comprising a vitamin D compound, optionally 25-hydroxyvitamin D or calcifediol, an extended release agent, and a surfactant. In embodiments, the formulation can be an extended release formulation, e.g. for oral use.

Another aspect of the disclosure herein is a pharmaceutical batch of dosage forms comprising a formulation according to the disclosure herein, and further characterized by low dosage form to dosage form variation in in vitro dissolution release. In embodiments, the dosage forms can be extended release dosage forms, e.g. for oral use.

Another aspect of the disclosure herein is pharmaceutical batches of dosage forms comprising a formulation according to the disclosure herein, and further characterized by low batch-to-batch variation in in vitro dissolution release. In embodiments, the dosage forms can be extended release dosage forms, e.g. for oral use.

Another aspect of the disclosure herein are methods of making the pharmaceutical formulations and dosage forms. In embodiments, the method can be a method of making an extended release pharmaceutical formulation, comprising compounding a vitamin D compound with a water-insoluble polymer, and optionally further with at least one pharmaceutically acceptable excipient selected from one or more of a diluent, an absorption enhancer, and a binder.

Another aspect of the disclosure herein is a method for improving batch to batch consistency in an in vitro release profile of an extended release vitamin D compound formulation, the method comprising compounding the vitamin D compound with a water-insoluble polymer material and optionally one or more additional excipients.

Another aspect of the disclosure herein is a method of treating a vitamin D responsive disease or condition comprising administering a formulation or dosage form according to the disclosure herein to a patient in need thereof.

For the compositions and methods described herein, optional features, including but not limited to components, compositional ranges thereof, substituents, conditions, and steps, are contemplated to be selected from the various aspects, embodiments, and examples provided herein.

Further aspects and advantages will be apparent to those of ordinary skill in the art from a review of the following detailed description, taken in conjunction with the drawings. While the compositions and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, four drawing figures are appended hereto.

DETAILED DESCRIPTION

Figure 1:
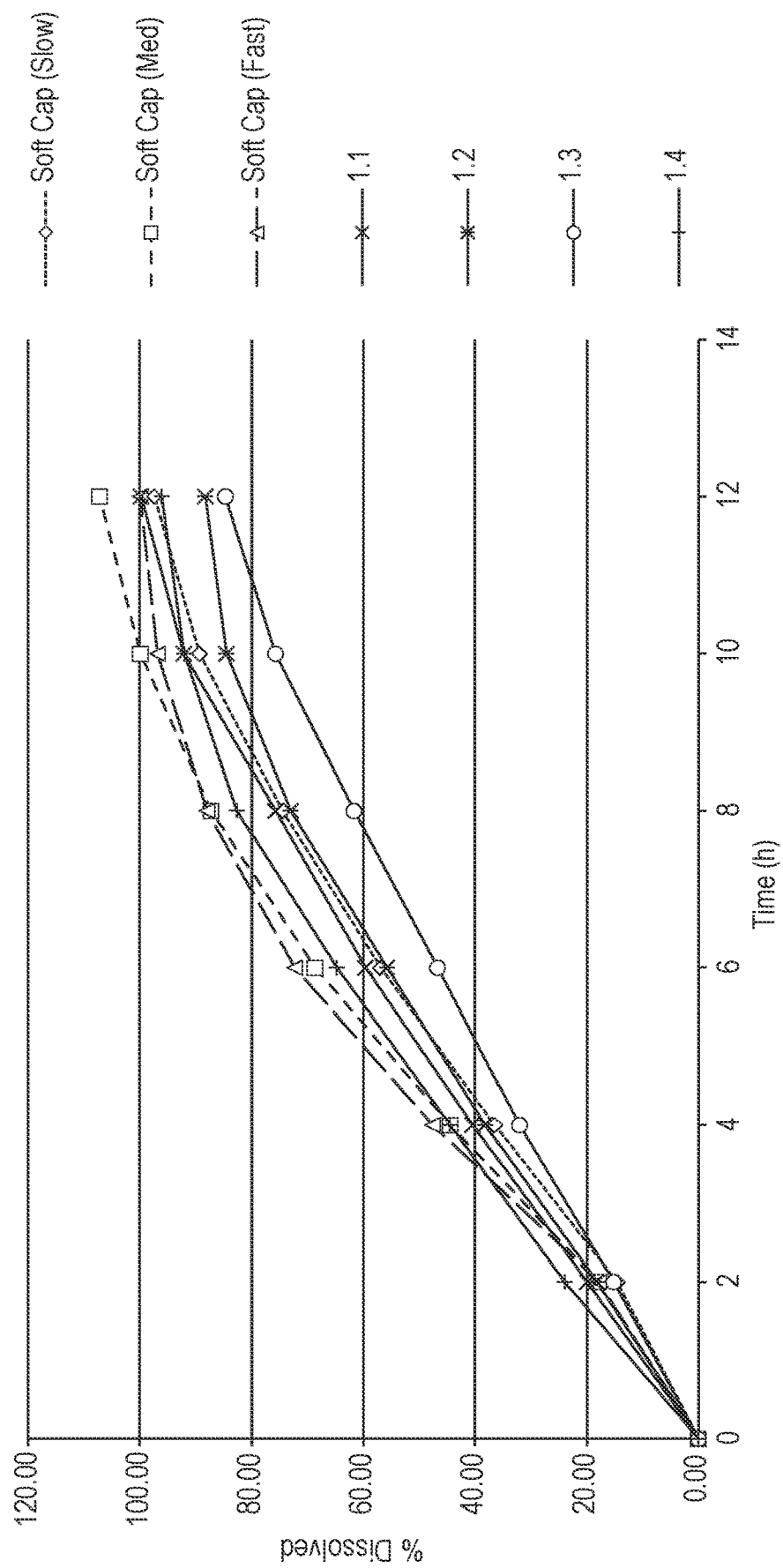
FIG. 1 shows dissolution release profiles of calcifediol-loaded, Eudragit-based pellets according to the disclosure herein compared to dissolution release profiles of a wax-matrix based soft capsule formulation.

There is a need for an improved formulation for safer delivery of vitamin D compounds, including calcifediol, including extended release formulations, and similarly improved formulations suitable for delivery to pediatric patients. Embodiments of the present invention can meet these needs and provide a range of extended release dosage forms as well as improved processes to make such formulations and dosage forms. These formulations may be made bioequivalent to a commercially approved wax based system but are also amenable to providing distinct in vitro extended release dissolution profiles and in vivo bioavailability. They can be made suitable for both pediatric patient populations as well as adult patient populations, and can be used, for example, to raise the level of serum 25-hydroxyvitamin D, and thus treat vitamin D insufficiency and other disorders including renal diseases and conditions.

The need to develop a pediatric 25-hydroxyvitamin D formulation led to a development effort that examined several different strategies to achieve a palatable, bioavailable, extended release oral dosage form that is easily swallowed. These strategies included pellets made using extrusion-spheronization technology with and without coating, coating inert seeds such as non-pareil seeds using fluid bed (Wurster) technology, nano/microparticulates technology, and lipid microparticles by spray congealing/spray chilling/spray cooling technology.

Efforts to make age-appropriate extended release oral formulations led to some surprising and unexpected results. For example, while several attempts with spray congealing of a wax-based mixture led to extended release dissolution release profiles, none sufficiently matched the target dissolution release profile of the prior wax-based matrix formulation; instead, the aqueous-based polymer pellet formulations using extrusion and spheronization technology led to improved 25-hydroxyvitamin D extended release formulations. Such formulations met all criteria necessary for pediatric use and, in addition, were suitable, based upon in vitro dissolution data, for adult use as well. In embodiments, the aqueous-based polymer pellet formulations can eliminate any need for coatings to obtain a bioequivalent product, and provide consistent and reproducible properties and consistent and reproducible in vitro release profiles on a unit dose to unit dose basis, and batch to batch basis.

Disclosed and described herein are extended release vitamin D formulations, including formulations suitable for delivery to pediatric patients in need of treatment thereof. Such formulations can also be useful in the treatment of adults in need of treatment thereof, e.g. for vitamin D insufficiency and for secondary hyperparathyroidism in CKD and other vitamin D related diseases and conditions. The formulations and formulation strategies described herein can be used to provide formulations bioequivalent to a commercially approved calcifediol extended release formulation but in a form deliverable to pediatric patients. Such forms are inclusive of conventional capsules, "easy to open" capsules or sachets that can be administered by emptying the entire contents into a small amount of liquid or onto a small amount of soft food. In addition to developing multiple suitable formulations for pediatric patients, the present invention has also led to a process for improving unit dose to unit dose and batch-to-batch dissolution profile variability and such improved formulations having more consistent in vitro and in vivo dissolution release profiles.

In one aspect, the extended release formulations comprise a vitamin D compound and an extended release component. In another aspect, such extended release formulations are in the form of spheronized pellets or multiparticulates. In one aspect, the formulations comprise spheronized pellets comprising an extended-release component selected from a polymer and/or a lipid component. The polymer is selected from a water-insoluble polymer, and can optionally include a water-soluble polymer. The active, such as calcifediol, can be embedded in a polymer network for extended release in vivo. In another aspect, the formulation can be a nano/micro particle formulations, e.g. made by emulsion followed by spray drying/freeze drying, such as an emulsion-diffusion-spray/drying freeze drying technique described herein. In another aspect, the formulations can be a powder formulation, e.g. made by spray congealing. In another aspect, the formulation can be a extended release coated seed. In another aspect, the formulation can be an active-containing granule.

A formulation and/or dosage form according to the disclosure herein can be free of waxes. In embodiments, the formulation and/or dosage form can be free of hydrocarbon waxes. In embodiments, the formulation and/or dosage form can be free of paraffin. A formulation and/or dosage form according to the disclosure herein can be free of hydrocarbon oils. In embodiments, the formulation and/or dosage form can be free of mineral oil. In another aspect, the dosage form can be free of a capsule shell. In embodiments, the dosage form can be free of a soft capsule shell. For example, a formulation and/or dosage form according to the disclosure herein can be free of hydrocarbon waxes and hydrocarbon oils.

U.S. Pat. Nos. 8,207,149 and 8,361,488 describe that prior wax-based formulations provided a solid or semi-solid, waxy pharmaceutical formulation that releasably binds and controllably release calcifediol in the gastrointestinal (GI) tract. The formulation includes a waxy controlled release carrier agent, a lipoidic agent, an oily vehicle, and a calcifediol compound which provides a formulation which is solid or semi-solid at room temperature and semi-solid or liquid at body temperature. U.S. Pat. No. 9,861,644 describes a wax based formulation that is suitable as a therapeutic and that possesses a long shelf-life. The patents describe that the lipoidic agent releases calcifediol in the GI tract of the subject and, without being intending to be bound by any particular theory of operation, that the lipoidic agent can serve one or more preferred functions such as creating a micro-emulsion of the oily vehicle in GI fluid; providing prolonged gastric retention, for example by bioadhesive properties such that the formulation interacts with the mucous layer of the stomach and/or intestine; and in enhancing the absorption of the calcifediol compound.

Hard paraffin wax acts as a control release agent producing a solid to semi-solid lipidic system at body temperature and producing a formulation that gradually releases the active ingredient through the process of erosion. This wax acts as a rate-controlling agent and is mainly responsible for the mechanical erosion mechanism. The GI medium penetrates into the wax and then facilitates slow release of calcifediol. Mineral oil is a mixture of refined liquid saturated aliphatic and cyclic hydrocarbons obtained from petroleum. Mineral oil is used as a vehicle in prior formulations, and may also influence the calcifediol absorption. Hypromellose in prior formulations acts as a release stabilizer which helps to stabilize release of calcifediol on standing/stability. The hypromellose stabilizes the release properties of the prior wax formulation over the intended shelf life of the product. Glycerol monostearate 40•55 (Type I) is an amphiphilic surfactant which forms mixed micelles with Lauroyl Macrogol-32 glycerides (Gelucire 44/14). Gelucires are formed by the esterification reaction between a polar polyethylene glycol (PEG), and an apolar vegetable oils or fatty acids. The main fatty acids of Gelucires are stearic, palmitic, and lauric acids, depending on their grades. These are non-ionic, water-soluble or water-dispersible pure surfactants which solubilize and increase the oral bioavailability of hydrophobic APIs such as vitamin D compounds (e.g. calcifediol). Gelucires possesses unique surfactant characteristics which enhance solubility and wettability of the API (e.g. calcifediol) both in vitro and in vivo. The improved in vivo drug solubility, facilitates the absorption and thereby bioavailability. Gelucires act as emulsifying/solubilising agents which facilitate the dissolution of insoluble calcifediol by emulsification and solubilisation mechanisms and thereby increase the bioavailability of calcifediol. These lipoidic agents also serve one or more functions such as creating a micro-emulsion of the oily vehicle in GI fluid; providing prolonged gastric retention, for example by bioadhesive properties such that the formulation interacts with the mucous layer of the stomach and/or intestine; and in enhancing the absorption of the calcifediol compound. The wax formulation releases gradually through mechanical erosion and/or gradual disintegration of the waxy composition. The wax, as well as emulsifiers, may help to absorb and may also provide bioadhesive property to the calcifediol. This may enhance the retention of calcifediol in the GI tract and get absorbed in a more prolonged and systematic manner enhancing the biopharmaceutical parameters.

The insoluble-polymer based formulations described herein (including pellet versions thereof) release the active via diffusion and/or erosion mechanisms. The active agent(s), such as calcifediol, can be embedded in the polymer network. The surface of the formulation (e.g. pellets) forms capillaries into which GI medium penetrates, facilitating slow release of active via diffusion through a polymer network in the pellet(s) or other dosage type. In these formulations, medium-chain triglycerides (e.g., Miglyol) acts as a solubilizer which enhances the solubility, e.g. of calcifediol. In the absence of specifically selected additional ingredients, there is no microemulsion and no bioadhesive mechanism, as in the case of the prior wax-based formulations. The degree and the dynamics of wax vs. polymer disintegration may also change in these two different formulations.

The formulations and dosage forms, and their related methods of making and are contemplated to encompass embodiments including any combination of one or more of the additional optional elements, features, and steps further described below (including those shown in the figures), unless stated otherwise.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "comprising" indicates the potential inclusion of other agents, elements, steps, or features, in addition to those specified.

As used herein, the term wt. % refers to parts by weight based on the total weight of the thing described, for example based on the total weight of the vitamin-D containing region, by default, or based on the total weight of the formulation, where applicable by context or explicitly described.

As used herein, the terms "controlled release," and "modified release" are used interchangeably and refer to the release of the vitamin D compound in a way that deviates from immediate release. As used herein, the terms "extended release," "sustained release," and "prolonged release" are used interchangeably and refer to the release of the vitamin D compound over a longer period of time than a comparable immediate release formulation.

As used herein, the term "25-hydroxyvitamin D" refers to one or more of 25-hydroxyvitamin D2, 25-hydroxyvitamin D3, 25-hydroxyvitamin D4, 25-hydroxyvitamin D5, 25-hydroxyvitamin D7, and combinations thereof. It is specifically contemplated that in any embodiment described herein, 25-hydroxyvitamin D can consist of or include 25-hydroxyvitamin D3, 25-hydroxyvitamin D2, or a combination of 25-hydroxyvitamin D3 and 25-hydroxyvitamin D2. For example, it is specifically contemplated that in any embodiment described herein, 25-hydroxyvitamin D can consist of or include 25-hydroxyvitamin D3. Serum total 25-hydroxyvitamin D refers to the total of all such 25-hydroxyvitamin D forms measured by assay, unless a particular 25-hydroxyvitamin D form is referred to.

As used herein, the term "1,25-dihydroxyvitamin D" refers to one or more of 1,25-dihydroxyvitamin D2, 1,25-dihydroxyvitamin D3, 1,25-dihydroxyvitamin D4, 1,25-dihydroxyvitamin D5, 1,25-dihydroxyvitamin D7, and combinations thereof. For example, 1,25-dihydroxyvitamin D can include 1,25-dihydroxyvitamin D2, 1,25-dihydroxyvitamin D3, or a combination of 1,25-dihydroxyvitamin D2 and 1,25-dihydroxyvitamin D3. It is specifically contemplated that in any embodiment described herein, 1,25-dihydroxyvitamin D can consist of or include 1,25-dihydroxyvitamin D3, 1,25-dihydroxyvitamin D2, or a combination of 1,25-dihydroxyvitamin D3 and 1,25-dihydroxyvitamin D2. For example, it is specifically contemplated that in any embodiment described herein, 1,25-dihydroxyvitamin D can consist of or include 1,25-hydroxyvitamin D2. Serum total 1,25-dihydroxyvitamin D will be understood to refer to the total of all such 1,25-dihydroxyvitamin D forms by assay, unless a reference is made to a particular 1,25-dihydroxyvitamin D form.

The vitamin D compound can include one or more of any desired vitamin D compound, whether natural or synthetic. In one type of embodiment, the vitamin D compound will include a 25-hydroxyvitamin D compound, e.g. one or more of 25-hydroxyvitamin D3, 25-hydroxvitamin D3, or 25-hydroxyvitamin D4. In other embodiments, the vitamin D compound can include an active vitamin D compound or analog, e.g. 1,25-dihydroxyvitamin D2, 1,25-dihydroxyvitamin D3, 1 α-hydroxyvitamin D2 (doxercalciferol), paricalcitol, 22-oxacalcitriol, dihydrotachysterol, or 26,26,26,27,27,27-hexafluorocoalcitriol (falecalcitriol).

The vitamin D compound is compounded with (e.g. via dissolution, mixing, emulsion, or any combination thereof) with one or more excipients to form a vitamin D formulation, as described below.

The concentration of vitamin D compound in a formulation according to the disclosure can be any suitable amount. For example, in an embodiment of a formulation according to the disclosure (e.g. one including a water-insoluble polymer as the extended release reservoir), the concentration of calcifediol is in a range of about 0.01 wt. % to about 1 wt. %, or about 0.01 wt. % to about 0.6 wt. %, or about 0.01 wt. % to about 0.3 wt. %, or about 0.03 wt. % to about 0.09 wt. %, for example 0.03 wt. %, or 0.06 wt. %, or about 0.09 wt. %.

In one aspect, poly(meth)acrylate polymers, including Eudragit polymers, are contemplated for the water-insoluble, swellable polymer component. These polymer function as extended release excipients which create the extended release profile. Two major mechanisms are possible for drug release through a Eudragit polymer: it is possible for drug release to occur by erosion or through diffusion. Eudragit polymers are copolymers derived from esters of acrylic and methacrylic acid, whose physicochemical properties are optionally influenced by functional groups. They are often available in different physical forms, such as aqueous dispersions, organic solutions, granules, and powders. Eudragit RL and Eudragit RS (CAS Number 33434-24-1) are cationic copolymers of ethyl acrylate, methyl methacrylate, and a low content of methacrylic acid ester with quaternary ammonium groups. The copolymers are water insoluble, but include ammonium groups present as salts to make the polymers permeable to water. Eudragit RS has relatively fewer ammonium groups and has lower permeability (poly(ethyl acrylate, methyl methacrylate, trimethylammonioethyl methacrylate chloride) 1:2:0.1), whereas Eudragit RL has relatively more ammonium groups and a higher permeability (poly(ethyl acrylate, methyl methacrylate, trimethylammonioethyl methacrylate chloride) 1:2:0.2). Eudragit RS and RL exhibit pH-independent swelling in water. The ratio of Eudragit RS and RL in the formulation can be adjusted to achieve a desired release profile. Powder forms of the Eudragit RS and RL can be used, and in the alternative granular forms, aqueous dispersions, and organic solutions (e.g. in acetone and/or alcohols) are available. Other suitable poly(meth)acrylate polymers include Eudragit NE and Eudragit NM (CAS number 9010-88-2), which are neutral ester copolymers based on ethyl acrylate and methyl methacrylate (poly(ethyl acrylate, methyl methacrylate) 2:1). Eudragit NE and Eudragit NM are also permeable to water, and exhibit pH independent swelling in water. In an extrusion-spheronization type formulation embodiment according to the disclosure, the amount of Eudragit RL PO is in a range of about 20 wt. % to about 80 wt. %, or at least 70 wt. %, for example. In one embodiment, the weight percentage is in the range of 40 wt. % to 60 wt. % Eudragit RL PO in the formulation. Such components are preferably used in an aqueous wet extrudable mass which forms a granulation which is subsequently spheronized to form pellets.

In another aspect, EC polymers are contemplated as a non-swellable, water-insoluble polymer material. These polymers also function as extended release components which slow release or facilitate the duplication of a target extended release profile or the creation of a unique extended release profile. Two major mechanisms are possible for drug release through a EC polymer:diffusion (concentration-dependent) and erosion. EC is a derivative of cellulose in which some of the hydroxyl groups on the repeating anhydroglucose units are modified into ethyl ether groups. The physical and drug-release properties of the EC can be influenced by its molecular weight (e.g. as indirectly specified by its viscosity), its degree of substitution (ethoxyl content), and particle size. For example, ECs are commercially available in three classes of ethoxyl content referred to as K, N and T type, which contain 44% to 47.9%, 48% to 49.5% and 49.6% to 51.0% ethoxyl contents, respectively. Alternatively, they are available in so-called "medium" grade having ethyoxyl content of 45.0% to 47.0%. In one type of embodiment, the EC will have an ethoxyl content in a range of about 48% to about 49.5%. The EC viscosity is measured as a 5% solution at 25° C. in a solvent consisting of 80% toluene and 20% ethanol. The viscosity of an EC for use in the composition described herein can be in a range of about 3 cP to about 50 cP, or about 3 cP to about 22 cP, or about 3 cP about 15.4 cP, or about 6 cP to about 15.4 cP, or about 6 cP to about 11 cP, or about 9 cP to about 15.4 cP, or about 9 cP to about 11 cP, for example. In other embodiments the viscosity of an EC for use in the composition described herein can be in a range of about 18 cP to about 110 cP, or 18 cP to 22 cP, or 41 cP to 49 cP, or 90 cP to 110 cP, or 18 cP to 49 cP, or 41 cP to 110 cP, for example. Generally, a smaller particle size can consolidate more efficiently and result in a slower release rate, while a porosity modifier can offset this effect. While the particle size is not particularly limited, in one type of embodiment it is contemplated to use a mean particle size of greater than 40 microns, or in a range of about 40 microns to about 500 microns, or about 250 to 500 microns, or about 100 microns to about 400 microns, or about 200 microns to about 300 microns. Optionally the particle size can include particles greater than 100 microns, or greater than 140 microns, or greater than 150 microns. For example the EC can be characterized by a viscosity in a range of 9-11 cP, ethoxyl content of about 48% to 49.5%, and a particle size in a range of about 250 to about 500 microns. A suitable EC is commercially available under the trade name Ethocel Standard 10 Premium. In other embodiments, the ethylcellulose can have a particle size characterized by a maximum of 150 microns, or 140 microns, or 100 microns; optionally the minimum particle size can be 3 microns, or 5 microns, or 30 microns. In additional embodiments, the ethylcellulose can be characterized by a mean particle size in a range of 5 to 15 microns, or 3 to 5 microns, or 30 to 60 microns. Ethylcellulose products are available from Dow Chemical under the grand name Ethocel and grades designated 4 Premium, 7 Premium, 7 FP Premium, 10 Premium, 10 FP Premium, 20 Premium, 45 Premium, 100 Premium, and 100 FP premium, for example. In an embodiment according to the disclosure, the amount of EC is in a range of about 5 wt. % to about 60 wt. %, for example. In an extrusion-spheronization type formulation embodiment according to the disclosure, the amount of EC is in a range of about 5 wt. % to about 60 wt. %, for example. Other contemplated ranges include about 1 wt. % to about 20 wt. %, or about 1 wt. % to about 10 wt. %, or about 2 wt. % to about 10 wt. %. These or other EC based formulations can include lactose monohydrate in a weight percentage of about 20 wt. % to 50 wt. %. Such components can be used in an aqueous wet extrudable mass which forms a granulation which is subsequently spheronized to form pellets.

In another aspect, low-substituted hydroxypropyl cellulose (L-HPC) polymers are contemplated for the water-insoluble polymer material. L-HPC is a low-substituted hydroxypropyl ether of cellulose with a small portion of the hydroxypropyl groups substituted for hydroxyl groups in the glucose unit. Whereas hydroxypropylcellulose (having a molar degree of substitution of about 3) is soluble in both water and alcohol, L-HPC (having a molar substitution of about 0.2-0.4) only swells in water and is insoluble. The degree of substitution can alternatively be characterized by the hydroxypropyl content in the polymer. For example, the hydroxypropyl content can be in a range of about 5% to about 15%, or about 8% to about 14%, or about 10% to 12%, or 11%. Similar to EC, the particle size is not particularly limiting, while mean particle sizes of 10 microns to 60 microns, or 10 microns to 45 microns, or 10 microns to 30 microns, or 15 microns to 25 microns, or 20 microns, are contemplated for example. In another aspect, the particle size D90 value can be in a range of about 50 microns to about 200 microns, or about 50 microns to about 135 microns, or about 50 microns to about 125 microns, or about 50 microns to about 100 microns, or about 60 microns to about 80 microns, or about 70 microns, or less than 100 microns. For example, an L-HPC can have a hydroxypropyl content of about 11%, a mean particle size of about 20 microns, and a particle size D90 of about 70 microns. A suitable L-HPC is commercially available under the trade name L-HPC LH-31.

In another aspect, a polyvinyl acetate polymer (PVA, CAS number 9003-20-7) is contemplated for the water-insoluble polymer material. This polymer is also used as an extended release component in the aqueous wet extrudable mass which forms a granulation and can be used to form spheronized pellets. In one type of embodiment, the insoluble polyvinyl acetate is blended with polyvinyl pyrrolidone (PVP, CAS number 9003-39-8), e.g. such a blend is commercially available under the trade name Kollidon SR. For example, with a water-soluble PVP, the PVP is leached out of the composition, leaving the PVA component with pores. For example, the PVP can be characterized by a 1% solution viscosity at 25° C. in a range of about 20 cP to about 40 cP, or about 25 cP to about 35 cP. In the alternative, the PVP can have a weight average molecular weight (e.g. by light scattering measurement) in a range of about 7,000 to about 100,000, or about 25,000 to about 60,000, or about 40,000 to about 55,000. The ratio of PVA to PVP can be adjusted to affect release properties. For example, the ratio of PVA to PVP can be in a range of about 10:1 to about 1:10, or about 10:1 to about 1:1, or bout 10:1 to about 2:1, or about 8:1 to about 2:1, or about 6:1 to about 2:1, or about 5:1 to about 3:1, for example about 4:1. While the particle size is not particularly limiting, a mean particle size in a range of about 50 microns to about 250 microns is contemplated for one type of embodiment. Optionally, a PVA/PVP blend can include small amounts of sodium lauryl sulfate (SLS, e.g. 0.8% by weight) and colloidal silica (e.g. 0.2% by weight) as stabilizers, e.g. in the form of KOLLIDON SR.

The drug release in from insoluble polymer based formulations is controlled by both erosion and concentration-dependent diffusion mechanisms (Fickian or non-Fickian) through channels or capillaries in the polymer formulation in the dissolution medium—(e.g., a channel/pore former (e.g. lactose with EC and hydrophilic HPMC with Eudragit polymer). There are different processes that come into play as a part of release mechanism: wetting of the polymer formulation with media; penetration of the media into the polymer formulation; phase transitions of the excipients; drug and excipient dissolution; and diffusion of drug and/or excipients out of the dosage form. In some cases, the formulations of these insoluble polymers ideally stay intact during the drug release process. However, the medium penetrates the pellets, so that the active pharmaceutical ingredient (API) molecules can diffuse out through the polymer network. The dimensions of the polymer formulation also increase with time of dissolution in the case of swellable polymers, while generally remaining same for non-swellable polymers. The dimensions of the polymer formulation form, the distribution of the drug in the polymer formulation, and the content and properties (like wettability and solubility) of the polymer formulation are key parameters affecting the processes governing drug release. Slightly and sparingly soluble active ingredients (e.g. calcifediol) cause retarded release due to their low dissolution rates.

In still another aspect, additives such as glyceryl behenate may be used as an extended release agent. Such compounds are used as thickening or gelling agents and are suitable as extended release agents and include, for example, glyceryl behenate (e.g. Compritol 888 ATO). It can be added at weight percentages of between 5 wt. % to 25 wt. % in a wet granulation aqueous blend, or 5 wt. % to 40 wt. %. For example, higher concentrations are particularly contemplated when glyceryl behenate is the major or sole extended release agent.

Polymer-based pellet formulations using extrusion and spheronization technology were shown by the present inventors to provide improved 25-hydroxyvitamin D extended release formulations. Such formulations met all criteria necessary for pediatric use but, in addition, are suitable, based upon in vitro dissolution data, for adult use as well. Embodiments of the extrusion-spheronization process can provide one or more advantages over other processes, including (1) being more cost efficient relative to manufacturing coated beads or pellets; (2) can provide a formulation bioequivalent to approved extended release calcifediol capsules without the need for a coating step; (3) provide a formulation that has consistent and reproducible properties from unit dose to unit dose; and (4) provide a formulation that has consistent and reproducible in vitro release profiles on a unit dose to unit dose basis and/or batch to batch basis (e.g. RSD among dosage forms, as measured from a six sample size analysis at 2, 4, 6, 10, and 12 hour dissolution time points, of less than about 16, or about 10 or less, or about 8 or less, or about 7 or less, or about 6 or less, or about 5 or less).

For example, the formulation can be bioequivalent to approved extended release calcifediol (e.g. Rayaldee®) by providing a mean $AUC_{0-inf}$ following oral dosing to humans in the fasted state which is 80% to 125% of the mean $AUC_{0-inf}$ following oral dosing in the fasted state of the approved extended release calcifediol product. In another embodiment, the formulation can be bioequivalent to approved extended release calcifediol by providing a mean $AUC_{0-inf}$ following oral dosing to humans in the fasted state which is 80% to 120% of the mean $AUC_{0-inf}$ following oral dosing in the fasted state of the approved extended release calcifediol product. In another aspect, the formulation can be bioequivalent to approved extended release calcifediol by providing a mean Cmax following oral dosing to humans in the fasted state which is 80% to 125% of the Cmax following oral dosing in the fasted state of the approved extended release calcifediol product. In another embodiment, the formulation can be bioequivalent to approved extended release calcifediol by providing a mean Cmax following oral dosing to humans in the fasted state which is 80% to 120% of the Cmax following oral dosing in the fasted state of the approved extended release calcifediol product. In one aspect, the fasted state can be defined by fasting for at least 10 hours.

For example, a formulation according to the disclosure herein can be formulated to provide a mean, baseline-adjusted value within 80% to 125%, or 80% to 120%, of one or more of the values described in Table 1 below, when administered at a single dose of 900 μg to a healthy human adult in the fasted state and measured over a 650 hour period.

TABLE 1

| Parameter | Value |
| --- | --- |
| Serum 25-hydroxyvitamin $D_3$ $AUC_{0-inf}$ (h * ng/mL) | 8879.83 |
| Serum 25-hydroxyvitamin $D_3$ $AUC_{0-650\ hr}$ (h * ng/mL) | 6395.80 |
| Serum 25-hydroxyvitamin $D_3$ Cmax (ng/mL) | 22.79 |

TABLE 1-continued

| Parameter | Value |
| --- | --- |
| $T_{1/2\ el}$ (h) | 325.74 |
| $T_{max}$ (h) | 24.78 |

In another aspect, a formulation according to the disclosure herein can be formulated to provide a mean, baseline-adjusted value within 80% to 125%, or 80% to 120%, of one or more of the values described in Table 2 below, when administered at a dose of 30 μg to a healthy human adult in the fasted state and measured over a 650 hour period.

TABLE 2

| Parameter | Value |
| --- | --- |
| Serum 25-hydroxyvitamin $D_3$ $AUC_{0-inf}$ (h * ng/mL) | 295.99 |
| Serum 25-hydroxyvitamin $D_3$ $AUC_{0-650\ hr}$ (h * ng/mL) | 213.19 |
| Serum 25-hydroxyvitamin $D_3$ Cmax (ng/mL) | 0.76 |
| $T_{1/2\ el}$ (h) | 325.74 |
| $T_{max}$ (h) | 24.78 |

In another aspect, a formulation according to the disclosure herein can be formulated to provide a mean, baseline-adjusted value within 80% to 125%, or 80% to 120%, of one or more of the values described in Table 3 below, when administered to a Stage 3 or Stage 4 CKD patient in fasted state according to the dosing described in the table, and measured after a six week period following initiation of dosing.

TABLE 3

| Parameter | Value w/30 μg daily dose | Value w/60 μg daily dose | Value w/90 μg daily dose |
| --- | --- | --- | --- |
| Serum 25-hydroxyvitamin $D_3$ $AUC_{0-\tau}$ (h * ng/mL) | 689.15 | 1447.80 | 2060.95 |
| Serum 25-hydroxyvitamin $D_3$ Cmax (ng/mL) | 27.75 | 60.33 | 85.69 |
| Serum 25-hydroxyvitamin $D_3$ tmax (days) | 37.75 | 41.13 | 42.50 |
| Serum 25-hydroxyvitamin $D_3$ $t_{1/2}$ (days) | 25.32 | 32.67 | 49.62 |

Such spheronized pellets produced from the aqueous-based wet granulation processes described herein can also have other components in the granulation blend including absorption enhancers, diluents and spheronizing aids, pore formers, binders, additional extended release agents, binding aids, fillers and water.

In another type of embodiment, one or more fatty acid glycerides, e.g., glyceryl behenate is contemplated for the water-insoluble material. Glyceryl behenate is a mixture of glycerides of fatty acids, mainly behenic acid (e.g. at least 50% or at least 80% behenic acid). In one type of embodiment, the content of 1-monoglycerides can be limited to range of 12.0-18.0%. In another type of embodiment, the glyceride can be characterized as a hydrophobic mixture of mono- (12 to 18% w/w), di- (45 to 54% w/w) and tri- (28 to 32% w/w) behenate of glycerol with melting point in range of 69 to 74° C. and with hydrophilic lipophilic balance (HLB) of about 2. In another embodiment, the glyceride can be characterized as a mixture of diacylglycerols (40 to 60% w/w), monoacylglycerols (13 to 21% w/w), and triacylglycerols (21 to 35% w/w). A suitable glyceryl behenate is commercially available under the trade name Compritol 888 ATO.

In another aspect, the water-insoluble formulation can be based on one or more of the water-insoluble polymer materials, and optionally include a lesser amount of a fatty acid glyceride. In another aspect, the water-insoluble formulation can be based on a fatty acid glyceride and include a lesser amount of one or more of the water-insoluble polymer materials.

In one type of embodiment, the water-insoluble polymer material is the predominant material in the formulation, e.g. present in an amount of at least 40 wt. %, or at least 50 wt. %, or in a range of 40 wt. % to 90 wt. %, or about 40 wt. % to about 80 wt. % or about 40 wt. % to about 70 wt. %, or about 40 wt. % to about 60 wt. %, or about 40 wt. % to about 50 wt. %. For example, one kind of polymer formulation can include about 50 wt. % to about 60 wt. %, or about 55 wt. %, of poly(ethyl acrylate, methyl methacrylate, trimethylammonioethyl methacrylate chloride) 1:2:0.2 (e.g., Eudragit RL). As another example, the a formulation can include a blend including about 40 wt. % to about 50 wt. % of Eudragit RL polymer in combination with a small amount (e.g. 1 wt. % to about 10 wt. %) of one or more other water-insoluble polymer materials, e.g. a L-HPC as described herein, or an EC as described herein, or a combination thereof.

In another type of embodiment, the water-insoluble polymer material is not the predominant material in the composition, e.g. when the water-insoluble polymer is relatively less permeable. For example, the water-insoluble polymer material can be included in an amount of 1 wt. % to about 40 wt. %, or about 1 wt. % to about 30 wt. %, or 1 wt. % to about 20 wt. %, or about 1 wt. % to about 10 wt. %, or about 2 wt. % to about 10 wt. %, or about 3 wt. % to about 8 wt. %, or about 5 wt. %. The composition can further include a release modifier, e.g. a pore former.

The formulation can optionally include one or more additional functional additives, including but not limited to release modifiers (including pore formers), absorption enhancers, fillers (also referred to as diluents), binders (including dry binders), spheronizing aids, flavorants, and lubricants.

For example, excipients useful in spheronized pellets as described herein include absorption enhancers, such as Miglyol 812N; diluents and spheronization aids, such as MCC (Avicel PH 101); diluents and pore formers, such as lactose monohydrate or HPMC; compacting/gelling/extended release agents, such as glyceryl behenate (Compritol 888 ATO, having melting range of 65° C. to 77° C. and an HLB of 2); extended release matrix formers/extrusion and spheronization aids, such as low-substituted hydoxypropylcellulose L-HPC LH-31); binding aids, such as Methocel K3 Premium LV; lubricants, such as talc powder or glyceryl behenate; flavoring agents, such as caramel; and purified water as a process diluent (e.g. to dissolve binder). Diluents and/or spheronization aids can be present in a concentration of about 30 wt. % to about 90 wt. %. The absorption enhancer can be present in a concentration of about 3 wt. % to about 10 wt. %. Binding aids such as Methocel K3 can be present in a concentration of about 5 wt. % to about 10 wt. %. Lubricants such as talc can be present in a weight concentration of about 1 wt. % to about 2 wt. %. The concentration of extended release matrix formers/extrusion and spheronization aids, such as L-HPC LH-31, can range from about 5 wt. % to 25 wt. %.

Release modifiers can include hydrocolloids, pore formers, and disintegrants. Pore formers include sugars (e.g. lactose, sucrose), sugar alcohols (e.g. mannitol), water-soluble salts (sodium chloride), and water-soluble polymers (polyethylene glycol, PVP, hypromellose, methyl cellulose) for example. In one type of embodiment, EC can be used as the water-insoluble polymer (e.g. 1 to 10 wt. %, or 5 wt. %) and a pore former can be used in a relatively higher amount (e.g., 20 wt. % to 40 wt. %), for example lactose monohydrate. Other examples include about 25 wt %, about 30 wt %, and about 35 wt %.

The composition can optionally include an absorption enhancer. Examples of suitable absorption enhancers include, but are not limited to, caprylocaproyl macrogolglycerides such as polyethylene glycosylated glycerides, also known as polyglycolized glycerides or PEGylated glycerides. PEGylated glycerides which may be employed in the composition include, but are not limited to, mixtures of monoglycerides, diglycerides, and triglycerides and monoesters and diesters of polyethylene glycol, polyethylene glycosylated almond glycerides, polyethylene glycosylated corn glycerides, and polyethylene glycosylated caprylic/capric triglyceride. The absorption enhancer can have an HLB value from 11 to 18, or 13 to 18, or from 13 to 16, or from 13 to 15, or 11-12.

One preferred absorption enhancer is known under the trade name GELUCIRE (Gattefossé Corporation, Paramus, New Jersey, USA). GELUCIRE is a well known excipient which belongs to a family of fatty acid esters of glycerol and PEG esters, also known as polyglycolized glycerides. GELUCIRE is used in various applications including preparing extended release pharmaceutical compositions. GELUCIRE compounds are inert, semi-solid waxy materials which are amphiphilic and are available with varying physical characteristics such as melting point, HLB, and solubilities in various solvents. They are surface active in nature and disperse or solubilize in aqueous media forming micelles, microscopic globules or vesicles. They are identified by their melting point/HLB value. The melting point is expressed in degrees Celsius. One or a mixture of different grades of GELUCIRE excipient may be chosen to achieve the desired characteristics of melting point and/or HLB value. One GELUCIRE composition is GELUCIRE 44/14, a mixture of lauroyl macrogolglycerides and lauroyl polyoxylglycerides that has a melting point of 44° C. and a HLB of 11. Another GELUCIRE composition is GELUCIRE 48/16, a.k.a. PEG-32-stearate, a.k.a. PEG 32 mono and diesters of stearic and palmitic acid, with a nominal melting point of 48° C. (range of 46° C. to 50° C.) and a HLB of 12. Another polyglycolyzed glyceride absorption enhancer is caprylocaproyl macrogol-8-glyceride (CAS No. 85536-07-8 and 84963-88-2). This is a mixture of mono-, di- and triesters of glycerol and of PEG 400 with medium-chain fatty acids (C8-C10) which is marketed, for example, by Gattefossé Corporation, Paramus, New Jersey, USA under the trade name LABRASOL. LABRASOL has a HLB value of 14 and has the following composition by weight: C8-C10 monoglycerides approximately 4%; C8-C10 diglycerides approximately 17%; C8-C10 triglycerides approximately 6%; C8-C10 monoesters of PEG 400 approximately 14%; C8-C10 diesters of PEG 400 approximately 36%; free PEG 400 approximately 20%; free glycerol approximately 3%. Another type of absorption enhancer is triglycerides, e.g. medium chain triglycerides. For example, a mixture of C8-C10 triglycerides can be used. In one type of embodiment, the C8-C10 triglycerides can include about 50 to 65 wt. % caprylic acid triglyceride and about 30 to 45 wt. % capric acid triglyceride. A suitable triglyceride is commercially available under the trade name Miglyol 812N. The absorption enhancer can be present in any suitable amount, for example about 1 wt % to about 20 wt %, or about 1 wt % to about 15 wt %, or about 1 wt. % to about 10 wt. %, or about 3 wt. % to about 10 wt. %, or about 5 wt. % to about 10 wt. %, or about 3 wt. % to about 5 wt. %. Other examples include about 3 wt %, about 5 wt %, and about 10 wt %. Optionally, when the formulation includes a hydrophilic excipient, e.g. a release aid, having a HLB of greater than 10, e.g. in a range of 11 to 18, or 13 to 18, then it also includes a lipophilic excipient, e.g. one having an HLB less than 10, e.g. 1 to 6, or 1 to 3, or 3 to 6.

The formulation can also include one or more fillers, also referred to as diluents. Fillers include, but are not limited to, lactose, saccharose, glucose, starch, microcrystalline cellulose (MCC), microfine cellulose, mannitol, sorbitol, calcium hydrogen phosphate, aluminum silicate, amorphous silica, sodium chloride, starch, and dibasic calcium phosphate dihydrate, for example. In one type of embodiment, the filler is not water soluble, although it may absorb water. As described above, when mixed with the other components (e.g. a water-insoluble polymer) a filler can function as a pore former. In one type of embodiment, the filler is a spheronization aid. Spheronization aids can include one or more of crospovidone, carrageenan, chitosan, pectinic acid, glycerides, β-CD, cellulose derivatives, MCC, powdered cellulose, polyplasdone crospovidone, and polyethylene oxide, for example. In one embodiment, the filler or spheronization aid includes MCC. A MCC can have any suitable particle size, e.g. a mean particle size in a range of about 10 microns to about 200 microns, or about 20 microns to about 100 microns, or about 20 microns, or about 50 microns, or about 100 microns, for example. A MCC can be characterized by a crystallinity in a range of about 60% to about 80%, for example. Suitable commercially-available MCCs are available under the brand name AVICEL, under the PH grades 101, 102, 104, 105, 112, 113, 200, 200 LM, 301, and 302, for example. In one embodiment the MCC is AVICEL PH 101; in another embodiment the MCC is AVICEL PH 201.

The amount of filler is not particularly limited, and for example can be in an amount of at least about 1 wt. %, or 5 wt. %, or 10 wt. %, or 20 wt. %, or 30 wt. %, or 40 wt. %, or 50 wt. %, or 60 wt. %, or 70 wt. %, or 80 wt. %, and up to about 95% wt. %, or about 90 wt. %, or about 80 wt. %, or about 70 wt. %, or about 60 wt. %, or about 50 wt. %, or about 40 wt. %, or about 30 wt. %, or ranges formed from any of the foregoing values. For example, the filler can be in a range of about 1 wt. % to about 95 wt. %, or about 30 wt. % to about 85 wt. %, or about 70 wt. % to about 90 wt. %, for example. A spheronizing aid can be included in such ranges, or in an amount of about 35 wt. % to about 60 wt. %, or about 35 wt. % to about 40 wt. %, or about 40 wt. % to about 60 wt. %, for example.

The formulation can include one or more binders, including dry binders. Binders include relatively low-viscosity, hydrophilic cellulose ethers, and PVP, for example. In other embodiments, binders can include carboxymethyl cellulose, starch, pregelatinized starch, acacia, tragacanth, gelatin, sodium alginate, low-substituted hydroxypropyl cellulose, and lowest viscosity grade of hydroxypropyl methylcellulose (HPMC). For example, the binder can be selected from low viscosity hypromellose, e.g. one having a 2% aqueous viscosity at 20° C. in a range of about 2 to about 6 cP, or about 2 to about 4 cP, or about 2.4 to about 3.6 cP. A suitable low viscosity hydroxypropyl methylcellulose is commercially available under the trade name Methocel K3 Premium LV. For example, the hypromellose can have a methoxyl % in a range of about 19 to about 30, or about 19 to about 24, or about 25 to about 35, or about 28 to 30. For example, the hypromellose can have a hydroxypropyl % of about 5 to about 15, or about 7 to about 12.

Pharmaceutically acceptable lubricants are known in the art and can include, but are not limited to, stearic acid, magnesium stearate, calcium stearate, aluminum stearate, talc, and siliconized talc. In one type of embodiment, the lubricant is talc. A small amount of lubricants can often be used, e.g. in a range of about 0.1 wt. % to about 5 wt. %, or about 0.5 wt. % to about 3 wt. %, for example 0.5 wt. %, 0.7 wt. %, 1 wt. %, 1.5 wt. %, or 2 wt. %.

The formulation can optionally include a top coating or over coating, to adjust the release profile. For example, a top coating can be used to delay or slow down release in initial hours after administration, e.g. to counteract an initial burst release, or otherwise slow an initial release that is more rapid than desired. Suitable top coating materials include film-forming polymers, for example. A top coating material can be water soluble, e.g. a water-soluble polymer described herein (e.g., hypromellose, PVP) or a water-swellable polymer that further includes a pore former (e.g. an EC as described herein together with a pore former, e.g. hypromellose). The top coat can optionally include a lubricant, e.g. talc. A suitable EC top coat material is commercially available under the trade name SURELEASE, sold as an aqueous, emulsified dispersion of plasticized EC. A suitable hypromellose pore former can have a 2% solution viscosity at 20° C. of about 3 cP, a methoxyl % in a range of about 19 to about 30, or about 19 to about 24, or about 25 to about 35, or about 28 to 30, and a hydroxypropyl % of about 5 to about 15, or about 7 to about 12. For example, the hypromellose can be one commercially available as PHARMACOAT 603. The ratio of top coat material, e.g. EC, to pore former, e.g. hypromellose, can be adjusted to give a desired release profile, and for example can be in a range of 80:20 to 20:80, for example, or 70:30 to 30:70, or 60:40 to 40:60, for example 65:45, or 60:40, or 55:45, or 50:50. Likewise, the amount of top coat can be adjusted to give a desired release profile. The amount of top coat material applied can be measured as weight gain of formulation particles, for example when the top coat is sprayed on the particles. For example, the amount of top coat on the formulation particles can be in a range of about 1 wt. % to about 40 wt. %, or 1 wt. % to about 30 wt. %, or about 5 wt. % to about 25 wt. %, for example 10 wt. %, or 15 wt. %, 20 wt. %, or 25 wt. %. Alternative coating materials to effect a delayed release include enteric coating materials, e.g. to effect release based on the GI medium pH. Examples of such materials include shellac (esters of aleurtic acid), cellulose acetate phthalate, poly(methacrylic acid-co-methyl methacrylate), cellulose acetate trimellitate (CAT), poly(vinyl acetate phthalate) (PVAP), and hydroxypropyl methylcellulose phthalate (HPMCP).

An alternative process to make pediatric formulations according to the invention include the preparation and use of nano/microparticles. Nano/microparticles are colloidal carriers which shown to offer a great potential in per-oral drug administration. In this type of embodiment, a vitamin D compound (e.g. calcifediol) can be encapsulated in a liquid oily core surrounded by a solid shell material of extended release polymer.

Extended-release nano/microparticles can be prepared using a emulsion-diffusion-spray drying/freeze-drying technique. With a poorly water-soluble API (e.g., calcifediol) a single-emulsion technique is more desirable.

A freeze-drying or spray-drying technique can be used to convert an emulsion into a powder formulation. Solvent blends for the homogenization to create an emulsion can include non-continuous phase solvents such as ethyl acetate and continuous solvents such as water. The final formulation of the extended release particles can be as an aqueous suspension, a non-aqueous suspension (e.g. with triglycerides, such as fatty acid triglycerides), or can be presented as a sprinkle form in a sachet.

Eudragit RL PO can be used as an extended release polymer, and poly(vinyl alcohol) as an emulsion stabilizer, for example. For example, the amount of Eudragit to stabilizer can be in a weight ratio range of about 80:1 to about 5:1, or about 50:1 to about 5:1, or about 40:1 to 10:1, or about 30:1 to 20:1, or 25:1, for example. The percentage by weight of the extended release polymer can broadly range from 0.5 wt. % to 98 wt. %, and in some embodiments can range from 75 wt. % to about 98 wt. % for example. The amount of polymers (e.g. Eudragit and poly(vinyl alcohol)) to API can be in a weight ratio range of about 80:1 to about 5:1, or about 50:1 to about 5:1, or about 40:1 to 10:1, or about 30:1 to 20:1, or 25:1, for example. In the alternative, EC or other extended release polymers described herein can be used as the solid shell material. The release profile can be modified by varying the extended release polymer type and the polymer to ratio, for example to create a slow release profile comparable to a target profile, e.g. the prior wax based calcifediol system. Various example formulation approaches are shown in Table 4 below.

TABLE 5

| Step | Description |
|---|---|
| 1 | API Stock Solution Preparation: Carefully prepare stock solution of calcifediol in solvent, e.g. ethanol. |
| 2 | Preparation of Polymeric Solution: Place 1000 ml glass beaker under homogenizer and add 150 ml of ethyl acetate. Slowly add weighed quantity of extended release polymer (e.g. Eudragit RL PO) into this beaker and homogenize at 10,000 rpm for 30 minutes under cooling conditions. |
| 3 | Preparation of Polymeric API Solution (Pre-emulsion): Weigh required quantity of API from the Step 1 stock solution and add this to 5 ml of solvent/vehicle (e.g. ethyl acetate) and stir gently under magnetic stirring. Add this API solution carefully to Step 2 polymeric solution and homogenize for another 30 min at 10,000 rpm. |
| 4 | Preparation of Aqueous Stabilizer: Dissolve a specified quantity of stabilizer (e.g. poly(vinyl alcohol)) in 25 mL of purified water. |
| 5 | Emulsification: Add the Step 3 Pre-emulsion to Step 4 aqueous stabilizer solution and subsequently homogenize at 15,000 rpm for 20 min. This forms the oil in water (o/w) emulsion. |
| 6 | Spray-Drying Stage: Spray dry the Step 5 emulsion using a spray drier (e.g. Buchi Mini Spray-Dryer B-191) using appropriate process parameters, e.g.: inlet temp 55 to 65° C., outlet temp 45 to 50° C., aspirator 90 to 100° C., pump (%) 5 to 15 RPM, flow rate 200 to 600 liters/hour. |
| 7 | Capsule Filling: Fill the Step 6 spray dried powder into Size 4 capsules (e.g. HPMC or gelatin capsules) calculating the amount of API using its theoretical weight. |

Processing and product parameters can be varied and include inlet temperature, percent aspiration, column air flow, cyclone sizes, homogenization speeds and conditions, polymeric solvent concentration, non-continuous to continuous phase ratios to provide an acceptable product yield.

TABLE 4

| Component | Embodiment | Type A | Type B | Type C | Type D | Type E | Type F |
|---|---|---|---|---|---|---|---|
| API | Calcifediol | 1 | 1 | 1 | | | |
| ER Polymer | Eudragit RL PO | 25 to 75 | | | | | |
| | Ethyl Cellulose | | 5 to 25 | | | | |
| | Chitosan | | | 5 to 25 | | | |
| | Poly Lactic-co-Glycolic Acid (PLGA) | | | | 0.5 to 5 | | |
| | Poly (epsilon-caprolactone) (PCL) | | | | | 0.5 to 10 | |
| | Methyl vinyl ether-maleic (Gantrez ®) | | | | | | 5 to 50 |
| Stabilizer | Poly (vinyl alcohol) Poloxamer 188 or 407 Pluronic F-68 or F127 Tween 20 or Tween 80 Sodium Cholate | | | | 1 to 5 | | |
| Cryoprotectant/ freeze-drying aid | Sucrose Fructose Dextrose Mannitol Trehalose | | | | 1 to 10 | | |
| Solvents/ Vehicles | Acetone Ethyl Acetate Methanol Water Dichloromethane Ethyl methyl ketone | | | | Q. S. | | |

A sequential method of making approach is described in Table 5 below. It would be understood by the skilled artisan that this sequence is representative and not limiting.

In addition to wet granulation/pellet formation and spray-dried emulsions, spray congealing is an alternative processing approach to produce formulations according to the disclosure herein, including extended release formulations, of vitamin D compounds, such as calcifediol. The process can be solvent-free, if desired. The hot melt processing can include spray cooling/congealing, for example, to yield small particle sizes. Spray cooling, also known as spray congealing or spray chilling, is a process that transforms a melt into well-defined, e.g. spherical, particles. This process uses spray drying technology with a rapid chilling process. It is capable of producing free-flowing lipid microparticles in a size range of about 10 microns to 1000 microns, for example. For example, cold nitrogen gas can be circulated through a column or other vessel while a hot melt mixture of lipid, API (e.g. calcifediol), and optional surfactant is sprayed into the column to create a fine mist of particles. The particles can optionally be coated with a top coat of extended release polymer and pore former.

A lipid which is solid or semi-solid at room temperature can be used as an extended release aid, and a surfactant can be used to aid solubility and complete release of the API. Such lipids include, but are not limited to, one or more of paraffin, glycerol monostearate (Geleol 40-55), Gelucire (e.g. grades 44/14, 43/01 (CAS No. 157710-38-8)), glyceryl distearate/palmitostearate (e.g. Precirol ATO 5, having a melting range of 50° C. to 60° C. and HLB of 2), and glyceryl dibehenate (e.g. Compritol 888 ATO). Gelucire 43/01 is a hydrophobic lipid with an HLB value of 1 and melting point of 43° C. It is a blend of saturated triglycerides of different fatty acids: C8-3%, C10-2%, C12-29%, C14-2%, C16-17%, and C18-36%. Gelucire 43/01 can also be used in combination with other grades of Gelucire to modify drug release for oral delivery. Other lipids can be selected from mixtures of mono-, di-, and tri-acylglycerols of fatty acids selected from palmitic acid, tallow acid, stearic acid, oleic acid, linoleic acid, linolenic acid, arachidic acid, behenic acid, erucic acid, and combinations thereof, e.g. palmitic and stearic acid. Surfactants include, but are not limited to one or more of PEGs (e.g. PEG 6000) and Tweens (e.g. Tween 80).

Spray congeals can be manufactured using a suitable spray-congealing unit in a closed loop set-up (e.g., as supplied by Büchi, Flawil, Switzerland, GEA Group, Düsseldorf, Germany, or ProCepT N.V., Zelzate, Belgium). A chiller can be used to cool down the gas in the column. Nitrogen gas can be used through the system in order to obtain temperatures in the system below 0° C. The temperature of the melt can be kept as low as possible. The melt can be sprayed by using a heated bi-fluid nozzle. Product can be dosed by a pressure vessel. Example process parameters are described in Table 6 below.

TABLE 6

| | |
|---|---|
| Heating bath nozzle (° C.) | 70 to 90 |
| Product Temp (° C.) | 60 to 90 |
| Chiller Temp (° C.) | −30 |
| Temp In (° C.) | −20 |
| Temp Chamber Out (° C.) | 0 to −2.5 |
| Temp Before Cyclone (° C.) | 0 to −2.5 |
| Pressure Drop cyclone (mbar) | 10 to 13 |
| Airflow in (m³/min) | 0.7 |
| Bi-fluid nozzle (mm) | 1 |
| Nozzle air (l/min) | 4 |
| Pressure on barrel (bar) | 0.4 to 1 |
| Dosing speed (g/min) | 20 to 70 |
| Cyclone Size Used | Large |

The active-containing formulation can be prepared in any suitable form. The drug-containing formulation can make up the entire dosage form, or it can be a region of the dosage form, e.g. as a core or as a coating (for example on an inert seed core, such as a nonpareil). In one type of embodiment, the formulation is in particle form, and optionally top coated. The particles can take any size or shape, e.g. pellets or mini tablets. In another type of embodiment, active-containing particles are made and then compressed, e.g. into the form of a pill, tablet or dragee. In another type of embodiment, active-containing particles (optionally coated), are filled into a capsule shell, pouch, or sachet, yielding a multiparticulate dosage form. Multiparticulates (dosage forms made of multiple particulate units, e.g. pellets or mini tablets) provide increased surface area as opposed to monolithic matrix tablets, allowing better release profiles and bioavailability. Unlike monolithic matrix tablets, multiparticulates spread uniformly throughout the GI tract. The multiparticulates are less susceptible to dose-dumping and their therapeutic effect is more predictive and reproducible than monolithic reservoir-type (matrix) formulations. The pellets reduce the likelihood of a burst effect as compared to matrix tablets and minimize inter- and intra-individual variability in the GI tract. The multiparticulates also provide a lower risk of local irritation due to the minute amount of drug they carry as compared to single unit matrix tablets. In case of monolithic matrix tablets, the GI transit rate is heavily dependent on stomach emptying rates and GI movement, but multiparticulates (e.g. pellets) because of their relatively smaller size produce highly reproducible GI transit rates and thus inter- and intra-subject variability is minimal compared to single unit formulations. Other advantages of the multiparticulates such as pellets over monolithic matrix tablets include: providing excellent flow properties, high packing ratios, low friability, flexibility to provide different drug substances that require different release patterns can be combined in a single dosage unit, and flexibility in the modulation of doses by using a greater or lesser amount of pellets, unlike monolithic matrix tablets.

The capsule shall can optionally be a HMPC shell or a hard gelatin shell. In another type of embodiment, the granules prepared from an aqueous based wet granulation can be directly compressed into a tablet or micro or mini-tablets which can be coated or uncoated.

In one type of particle form, the particle sizes (diameters) are in a range of about 0.2 mm to about 2.8 mm, or about 0.2 mm to about 2.5 mm, or about 0.2 mm to about 2.0 mm, or about 0.7 mm to about 2.5 mm, or about 0.7 mm to about 2.8 mm, or about 0.5 mm to about 2.8 mm, or about 0.8 mm to about 1.7 mm, or about 0.5 mm to about 1.2 mm, or about 0.5 mm to about 1.0 mm. For example, the target particle size can be up to 2.5 mm with no more than 10 percent variation over this size, to a maximum size of 2.8 mm. Particles can be sorted to the desired size ranges by sieving according to known methods. The formulation can also be characterized by a mean particle size in any of the foregoing ranges or amounts. As the particle size becomes too large, the particles are too large for use in drug products that are labeled to be administered via sprinkling on a substrate (e.g., on applesauce or other soft foods, such as jellies) and swallowed without chewing, or administered via an enteral feeding tube. In another type of dosage form and related administration method, multiparticulates according to the disclosure herein can be dispersed in a suspension base and administered as a powder for oral suspension. The suspension base can include purified water, for example, and optionally with one or more excipients. The suspension base can include at least 50 wt. % water, more than about 50 wt. % water, at least about 80 wt. % water, at least about 90 wt. % water, at least about 95 wt. % water, at least about 99 wt.

% water, or 100 wt. % water, for example. The suspension base can be a sugar-based syrup, for example. The suspension base can optionally include a suspending or thickening agent. Suitable suspending and thickening agents include, for example, methylcellulose, starch, xanthan gum, and glycerin. In another embodiment, the suspension base is non-aqueous, e.g. containing or consisting of triglycerides.

In the case of sprinkle-type dosage forms, a narrow distribution of particle sizes with size less than 1.0 mm, optionally smaller than 0.5 mm is desirable to avoid grittiness and unpleasant mouthfeel in babies. Sugar spheres are preferred over MCC spheres, as the sweet taste of the sugar can also act as a taste masking aid.

As another alternative, a layered formulation is contemplated. This type of formulation includes a starter seed (e.g. non-pareil seed) having a layer of vitamin D compound, which further has a seal coating (e.g. low-viscosity hypromellose) to make the surface of the seeds smooth after API layering/coating and also to achieve uniform coating(s) at subsequent stages. Over the seal coating is an extended-release polymer coating (e.g., a water-insoluble polymer, such as one described herein, with a pore former). This embodiment can further include an optional taste-masking coating, and a further optional seal coating over the extended-release polymer coating and under the taste-masking coating, if desired.

In one type of approach, for example, seeds (a.k.a. pellets or spheroids) can be prepared with one or more processes including extrusion with spheronization, rotary fluid-bed processing, and spray-congealing. The seeds can optionally have API within the seeds themselves, in a range of 0.01% to 10% by weight of the seed, for example. These seeds are coated with one or more coating layers, for example using fluid bed processing using Wurster coating technology. For example, the seeds can have a first seal coating in a range of 1 wt. % to 5 wt. %, based on the weight of the seeds, and a functional release coating in a range of 3 wt. % to 50 wt. %, based on the weight of the seeds. There can be an optional second seal coating, for example in a range of 1 wt. % to 5 wt. % based on the weight of the seeds, and second functional release coating, for example in a range of 3 wt. % to 50 wt. % based on the weight of the seeds. Following the optional second functional release coating, there can be a third optional seal coating, for example in a range of 1 wt. % to 5 wt. % based on the weight of the seeds. The formulation can also include an aesthetic (non-functional) coating, for example in a range of 1 wt. % to 5 wt. %, based on the weight of the seeds.

In another type of approach, inert non-pareil seeds can be used and coated with different layers to achieve a desired release profile, e.g. using fluid bed processing using Wurster coating technology. In this approach, inert non-pareil seeds can be selected with a particular size mean or range, e.g. in a range of 150 μm to 1000 μm. A drug loading layer is made over the seeds, e.g. with a loading of 0.01% to 10% by weight of the seeds. These seeds are coated with one or more coating layers, for example using fluid bed processing using Wurster coating technology. For example, the drug-coated seeds can have a first seal coating in a range of 1 wt. % to 5 wt. %, based on the weight of the seeds, and a functional release coating in a range of 3 wt. % to 50 wt. %, based on the weight of the seeds. There can be an optional second seal coating, for example in a range of 1 wt. % to 5 wt. % based on the weight of the seeds, and second functional release coating, for example in a range of 3 wt. % to 50 wt. % based on the weight of the seeds. Following the optional second functional release coating, there can be a third optional seal coating, for example in a range of 1 wt. % to 5 wt. % based on the weight of the seeds. The formulation can also include an aesthetic (non-functional) coating, for example in a range of 1 wt. % to 5 wt. %, based on the weight of the seeds.

The excipients for the seed and coating materials can be selected from those known in the art, including those described herein. For example, non-pareil seed materials can be selected from microcrystalline cellulose, silicon dioxide, mannitol, other sugars, and combinations thereof. Functional coating excipients can be selected from cellulosics, HPMC, ethylcellulose, waxes, glyceryl monostearate, acrylic polymers (including Eudragits), and combinations thereof. Seal coating excipients can be selected from cellulosics, e.g. HMPC. Pore formers can be selected from cellulosics, HMPC, and lactose. Plasticizers can be used in the seal, functional, and aesthetic coatings, and can be selected from dibutyl sebacate, triethyl citrate, and PEGs, for example. Aesthetic coating materials can be selected from hypromellose, polyvinyl alcohol, and commercial coating products such as Opadry® coating. The coatings can be applied as aqueous or non-aqueous solutions.

The final dosage form can have any desired amount vitamin D compound in a unit dose. For example, a capsule shell can be filled with sufficient formulation material, such as granule, particle, or pellet, to yield a dosage form having an amount of calcifediol in a range of about 1 μg to about 1 g, or about 10 μg to about 600 μg, or about 10 μg to about 300 μg, or about 10 μg to about 100 μg, or about 30 μg to about 90 μg, for example 30 μg or about 60 μg or about 90 μg. Dosage forms other than capsules, e.g. sachets, pills, or tablets, can have the same or similar strengths. Dosage forms, including granules, pellets, sachets, capsules, etc. can be stored with a desiccant.

As described below in connection with the Examples, various example dosage forms (e.g. EC-based formulations) have exhibited in vivo exposure characteristics that differ from the currently-approved Rayaldee® extended release calcifediol capsules product. It is contemplated that dosing of such products can be scaled based on their in vivo exposure characteristics (e.g. based on AUC(0-inf) compared to Rayaldee® extended release capsules, or based on AUC(0-t) compared to Rayaldee® extended release capsules). For example, the pellets of Example 9 can have a dose of 60 mcg calcifediol in place of 30 mcg Rayaldee® extended release capsules.

In principle, the formulations described herein can be characterized by any extended release profile.

In one type of embodiment, the target dissolution profile of a formulation according to the present disclosure can be within the specification limits of in vitro dissolution profile(s) of an extended release 25-hydroxyvitamin D capsule (30 mg) in a lipophilic wax matrix formulation (Table 7), e.g. Rayaldee®. The specification limits can be applied based on the dissolution of each individual unit. For example, ≤30% label claim is dissolved at 2 hours; 53-78% of label claim is dissolved in 6 hours and ≥80% of label claim is dissolved at 12 hours. The dissolution can be measured using following method of dissolution, for example.

| USP Apparatus | II (Paddle with Sinker) |
|---|---|
| RPM | 75 |
| Medium | 0.5% SDS in 5 mM Sodium Dihydrogenphosphate Monohydrate, pH 6.8, 37 ± 0.5° C. |
| Volume (mL) | 500 |

FIG. 1 shows comparative in vitro dissolution release profiles of such 30 ug dosage forms, representative of 52 commercial batches. The results are grouped into relatively "slow" "medium" and "fast" release profiles. The Relative Standard Deviation was assessed across all dissolution release profiles.

TABLE 7

| Dissolution Time Point (hours) | A ("slow") | RSD (%) | B ("medium") | RSD (%) | C ("fast") | RSD (%) |
|---|---|---|---|---|---|---|
| 2 | 14.58 | 17.31 | 18.00 | 17.92 | 17.90 | 24.56 |
| 4 | 36.53 | 7.00 | 44.44 | 13.21 | 47.61 | 18.69 |
| 6 | 56.90 | 5.69 | 68.67 | 11.34 | 72.26 | 11.99 |
| 8 | 74.48 | 3.61 | 87.17 | 9.30 | 87.90 | 7.52 |
| 10 | 89.26 | 2.13 | 99.84 | 5.51 | 96.79 | 3.56 |
| 12 | 97.34 | 1.33 | 107.14 | 2.60 | 99.91 | 2.39 |

The delta (Δ) between A and C at the given time points was approximately 3% at the 2 hour point; 11% at the 4 hour time point; 15% at the 6 hour time point; 13% at the 8 hour time point; 8% at the 10 hour time point and 3% at the 12 hour time point. The formulations of the invention can be designed to essentially match any one of the formulations A, B or C, or combinations thereof (e.g. average of any two, or average of all three A, B, and C). For example, the formulation can be characterized by in vitro dissolution release values of: about 14% to about 18% at 2 hours; or about 36% to about 48% at 4 hours; or about 56% to about 73% at 6 hours; or about 74% to about 88% at 8 hours; or about 89% to about 100% at 10 hours; or about 97% to at least 100% at 12 hours, or any combination thereof, e.g. a dissolution release profile characterized by the combination of all such time points. In another embodiment, the formulation is characterized by an in vitro dissolution release profile of less than 20% release of active at 2 hours; 35% to 45% at four hours; 55% to 80% at six hours; 65% to 85% at eight hours; 85% to at least 100% at ten hours and 90% or more (e.g. 90% to 110%) at 12 hours. In another embodiment, the formulation is characterized by an in vitro dissolution release profile of 14 to 18% release at two hours; 36% to 45% at four hours; 55% to 69% at six hours; 74% to 88% at eight hours; 89% to at least 100% at 10 hours; and 97% or more (e.g. 97% to 110%) at 12 hours.

In the alternative, a formulation according to the disclosure herein can be made to create a unique or customized extended release dissolution profile. A formulation according to the disclosure herein can also be made to have consistent unit dose to unit dose in vitro dissolution profiles with limited intra batch variability, or batch-to-batch variability. For example, the dissolution profile can be measured using USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL. In one embodiment, the variability can be expressed as RSD (%) at any dissolution time point 2 hours or more, as measured from six dosage forms. For example, the RSD can be at dissolution points of 2, 4, 6, 8, 10 and 12 hours. In another embodiment, RSD can be at dissolution points of 4, 6, 8, 10 and 12 hours. In another embodiment, RSD can be at dissolution points of 2, 6, and 12 hours. For example, as demonstrated in the Examples below, such RSD values can be less than 16%, or 10% or less, or 8% or less, or 6% or less, or 5% or less.

Also contemplated are methods for the preparation of a formulation and a final dosage form according to the disclosure herein. The formulation including the vitamin D compound can be made by any suitable process, including but not limited to direct compression, granulation, extrusion, fluid bed coating, or any combination thereof.

Such processes include aqueous-based extrusion/spheronization to produce granules/pellets suitable for extended-release formulations containing a vitamin D compound (e.g. 25-hydroxyvitamin D or calcifediol), coating processes to coat seeds or active-containing granules, and processes to make vitamin D extended release formulations from nano- or microparticles. One embodiment of a process to make suitable pediatric vitamin D formulations wherein the active is 25-hydroxyvitamin D or calcifediol includes aqueous-based extrusion/spheronization to form multiparticulate granules/pellets which can be uncoated or coated. The controlled-release polymers suitable for use in preparing such granules can be selected from, for example, Eudragit RL PO, Eudragit RS PO, EC, L-HPC, LH-31, Compritol 888 ATO and Kollidon SR. In an embodiment, other excipients including binders and/or absorption enhancers, lipidic agents, diluents, spheronizing aids, flavoring agents and pore formers may be utilized in the aqueous-based extruded granule formulation. In one kind of embodiment, pellets are readily made from the extrudable aqueous-based formulation without the need for additional coating(s) to achieve a target extended release in vitro and in vivo profile. Such a process can include (1) forming an aqueous-based extrudable mass including active and inactive excipients; (2) extruding such mass to form active-containing granules; (3) spheronizing the granules to form pellets and (4) drying the pellets. The dried pellets can optionally be coated with a lubricant and/or flavorant, e.g. talc and flavorant. More specifically, the process can include moistening a powder mixture of API and excipients, forming extrudates through extrusion, breaking and rounding the extrudates to round pellets through spheronization, and drying the finished pellets. The pellets can have sizes in a range of 200 um to 2 mm in diameter, for example. The aqueous-based formulation used to form the wet-extrudable mass can include a considerable percentage of water (wt/wt). The percentage of water can be in a range of 10 wt. % to 90 wt. %, or at least 50 wt. %. Granules produced by this process (aqueous versus non-aqueous) have the requisite strength and integrity to provide workable, extrudable and functional spheronized pellets. The pellets can also be referred to as beads or spheroids. Enhanced properties can include one or more properties including optimal flow characteristics; reproducible provision into capsules or other drug delivery vehicles; optimal density/hardness properties for handling and, if desired, coating; improved hardness and friability (e.g. not more than 1.0 percent); and more consistent batch-to-batch in vitro and in vivo drug delivery and release profiles. The pellets can provide one or more benefits including: dispersing freely in the GI tract, thus improving drug absorption, minimizing dose dumping, reducing peak plasma fluctuations, and minimizing side effects; avoiding high local concentrations of API in the GI tract; reducing processing steps, e.g. by avoiding the use of a coating; improving flow properties, e.g. for capsule or sachet filling; providing a narrow particle size distribution; and providing uniform packing characteristics.

In one embodiment, the formulation is formed by granulating a mixture of the vitamin D compound with a material (e.g. water-insoluble polymer) and one or more other optional excipients, and optionally tailoring the formulation process to a desired particle size range, e.g. via extrusion parameters, and/or optionally in combination with one or more steps including sieving, fractional sieving, and milling. In another embodiment, the formulation can be formed by extrusion and spheronization of a mixture of the vitamin D compound with a material as described herein (e.g. water-insoluble polymer) and one or more other optional excipients. For example, the extruder can be fitted with an extrusion screen of a desired size, e.g. 0.1 mm to 5 mm, or 0.5 mm to 2 mm. In addition or in the alternative, the spheronizer can be fitted with a plate of desired dimensions and configuration, e.g. a 0.1 to 5 mm cross hatch plate, or 0.5 to 2 mm cross hatch plate. Granulating processes can include fluid bed granulation, wet granulation, hot melt granulation, and spray congealing, for example. Other processes include slugging and roller compaction. As it is generally known in the art, mixtures which are to be granulated can first be dry-blended. The dry-blended dry ingredients can be mixed with water, prior to extrusion.

For example, in one embodiment of a method to produce spheronized pellets, the dry ingredients are combined, blended and mixed with about 50 wt. % to 80 wt. % water and wet granulated to form a wet-extrudable mass. The extrudable mass of the combined ingredients in selected weight ratios depending upon the extended release polymer(s) and excipients is blended, extruded, spheronized and dried to form the desired pellets used in the pediatric or adult formulation(s). For example, a mixture of calcifediol and triglycerides can be added to a pre-mixed blend of dry excipients, and then a binder solution can be added to prepare a wet mass for extrusion. The drying can be done by tray drying, vacuum drying, or fluid bed drying, for example.

A sequential method of making approach is described in Table 8 below. It would be understood by the skilled artisan that this sequence is representative and not limiting.

TABLE 8

| Step | Description |
|---|---|
| 1 | Binder Solution Preparation: Dispense purified water in a vessel. Place this vessel on a magnetic stirrer and stir under vortex with the help of magnetic bead at a temperature of 80° C. Slowly add a dispensed quantity of binder (e.g. Methocel K3 Premium LV) at the outermost edge of the vortex of warm purified water. After ensuring complete solubility of the binder, set aside this vessel to settle down the foam generated during vortex. |
| 2 | API Stock Solution Preparation: Prepare stock solution of API (e.g. calcifediol) in solvent (e.g. ethanol). Dispense required amount of API from prepared stock solution into a glass container. |
| 3 | Preparation of API and Miglyol Mixture: Dispense absorption enhancer (e.g. Miglyol 812N) separately and add this to Step 2 glass container containing the API, e.g. using Pasteur pipette. Place this on a magnetic stirrer and stir at a gentle speed for 15 minutes. |
| 4 | Dry-Mixing: Pass diluent, spheronizer (e.g. Avicel PH 101) and extended release polymer (e.g. Eudragit RL PO, and/or Ethocel Standard 10 Premium) through 1000-micron sieve (by sandwich method) and transfer this sieved material into a granulator (e.g. GMX high shear granulator) and mix for 15 minutes at 200 rpm impeller speed. |

TABLE 8-continued

| Step | Description |
|---|---|
| 5 | API and Miglyol Mixture Addition to Dry-Mix: Slowly add mixture of Step 3 to a dry mix of Step 4 and mix for 30 minutes at 200 rpm impeller speed. |
| 6 | Preparation of Wet Mass for Extrusion: Set granulator (e.g. GMX high shear granulator) for 200 RPM impeller speed for 5 minutes and manually add the Step 1 binder solution to the above Step 5 mixture (ensure chopper is off). If required, an additional amount of purified water and mixing may be utilized to achieve suitable extrudable wet mass. |
| 7 | Extrusion Process: Gradually feed the wet mass of Step 6 to an extrusion chamber (e.g. Caleva Screen Extruder fitted with 1.0 mm screen). Adjust the extruder speed, (e.g. to maximum or approx. 30-35 RPM using Caleva Screen Extruder) to get uniform extrudates. |
| 8 | Spheronization Process: Immediately transfer the Step 7 extrudates to a spheronizer chamber fitted with 1.0 mm cross-hatch plate and carry out spheronization at 1500 rpm until desired spheroids are formed. Discharge the pellets through the discharge port of the spheronizer by reducing the speed to 750 rpm. (Approximate end point of spheronization is when fines are observed to start sticking at spheronization wall or formation of doublets/triplets on the spheronization plate). |
| 9 | Drying of Pellets: Dry the Step 8 spheroids/pellets at 60° C. to 65° C. until loss on drying (LOD) between 4-6% is achieved. |
| 10 | Fractionation of Pellets: Screen the pellets through series of sieves (1.40 mm, 1.00 mm, 850 μm, 500 μm and 250 μm and base plate). Arrange and place these sieves on a sieve shaker (e.g. Electropharma Electromagnetic sieve shaker). Add the Step 9 dried pellets on the top sieve, i.e. 1.4 mm and run the sieve shaker for 10 minutes with low (e.g. 5%) power and in continuous mode. Select the desired size of retained pellets for lubrication. |
| 11 | Flavor Addition and Lubrication with Talc: Weigh the desired size of retained pellets of Step 10. Based on this yield, calculate the flavor and talc quantities and dispense. Separately pass caramel flavor and talc through 250 μm sieve and mix pellets using these two for 5 min. |
| 12 | Capsule Filling: Fill the Step 11 pellets into Size 4 capsules (e.g. HPMC or gelatin) with 50 mg as their fill weights. |

It has been found that extrusion and spheronization of a mixture of the vitamin D compound with an extended release component as described herein (e.g. water-insoluble polymer) can provide desirable vitamin D-containing polymer particles (e.g. containing calcifediol) with dissolution release properties similar to or equivalent to a commercially-available extended release wax matrix formulation of calcifediol, e.g. Rayaldee®. It is contemplated to use calcifediol as a vitamin D compound in an extrusion-spheronization type formulation. The Rayaldee®-type formulation can have the following composition filled into soft OptiShell® plant polysaccharide shells: calcifediol 0.02% of capsule fill by weight, paraffin 20.0% of capsule fill by weight, mineral oil 35.34% of capsule fill by weight, Hypromellose 10.0% of capsule fill by weight, mono- and di-glycerides 22.56% of capsule fill by weight, lauroyl polyoxylglycerides 9.75% of capsule fill by weight, dehydrated alcohol 2.32% of capsule fill by weight, and BHT 0.02% of capsule fill by weight.

The formulation described herein can be directly processed as a finished dosage form, or it can be further processed to make a finished dosage form. For example, the formulation can be top coated. The coating can be done by fluid bed coating, for example, with a top-, tangential-, or bottom-spray configuration. As another example, the formulation can be compressed, e.g. into the form of a pill or tablet. In another type of embodiment, particles of the formulation described herein (optionally coated), are filled into a capsule shell or can be presented in a sachet form or can be provided along with a suspension as a vehicle to suspend these pellets before they are administered.

Extruded/spheronized calcifediol pellet batches described in the Examples below and employing Compritol 888 ATO showed a decline in dissolution profiles with accelerated storage stability testing. A lipid-containing formulation described herein (e.g. one containing a Gelucire or Compritol component) can be heat cured to stabilize the formulation against structural change upon long-term storage. In the absence of heat curing, a lipid component can migrate over time upon storage, blocking hydrophilic sites or pores, and thus changing the dissolution release characteristics as compared to formulations at time zero. Further optionally, a formulation described herein having a higher-melting lipid can be compounded with a lower-melting lipid, such that the formulation can be heat-cured at a lower temperature. For example, a formulation containing glyceryl behenate (e.g. Compritol 888 ATO) having a melting range of 65° C. to 77° C. and HLB of 2) can be compounded with, or partially substituted with glyceryl distearate/palmitostearate (e.g. Precirol ATO 5) having melting range of 50° C. to 60° C., e.g. 54° C. and HLB 2, such that the heat curing can be done around 60° C. and below 65° C. (relative to glyceryl behenate), thus avoiding degradation of calcifediol. Optionally, the heat curing can be done over a time period ranging from minutes to weeks, e.g. 1 hour to one week, or 1 to 24 hours, e.g. 2 hours, 3, hours, 4 hours, 6 hours, 12 hours, or 24 hours, or 48 hours, or 72 hours, or 96 hours, or one week, for example.

Administration of a dosage form according to the disclosure can be based on the weight of active ingredient in the formulation. For example, administration of a calcifediol-containing formulation can be in an amount of 1 µg calcifediol to about 1 g calcifediol. The dosage form can be orally administered to a patient suffering from a condition for which a vitamin D compound is indicated, including, but not limited to, vitamin D deficiency, vitamin D insufficiency, secondary hyperparathyroidism associated with CKD (e.g., any of Stage 1 to 5 CKD, including Stage 3, Stage 4, Stage 5, or Stages 3-5, or Stages 3-3). In any method or use described herein, the treatment of humans is contemplated. In any method or use described herein, the treatment of mammals is contemplated. In any formulation, dosage form, use, and method described herein, oral formulations and oral administration is contemplated. The compositions of the disclosure can be used in combination with other therapies useful for the indicated diseases and disorders.

In addition or in the alternative, a formulation described herein can be used in the preparation of a medicament for use in treating a vitamin D-responsive condition or disease.

The compositions and methods described herein are useful for prophylactic or therapeutic treatment of vitamin D-responsive diseases, i.e., diseases where 25-hydroxyvitamin D or active vitamin D (e.g., 1,25-dihydroxyvitamin D) prevents onset or progression of disease, or reduces signs or symptoms of disease. Such vitamin D-responsive diseases include hyperparathyroidism, hyperparathyroidism secondary to CKD (e.g., individually or in a range of any of Stage 1, 2, 3, 4, or 5), hyperparathyroidism secondary to CKD in patients undergoing hemodialysis, or tertiary hyperparathyroidism. Such vitamin D-responsive diseases include cancer (e.g., breast, lung, skin, melanoma, colon, colorectal, rectal, prostate and bone cancer). Active vitamin D (e.g. calcitriol) has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, autism (or autism spectrum disorder), chronic obstructive pulmonary disease, Parkinson's disease, polycystic kidney disease (PKD), polycystic ovary syndrome, pancreatitis, nephritis, hepatitis, and/or infection. Vitamin D-responsive diseases have also been reported to include hypertension and cardiovascular diseases. Thus, the methods contemplate prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis. It is contemplated to use any formulation described herein, including Rayaldee® extended release capsules, for treatment or prevention of such diseases, e.g. preventing onset or progression of a disease, or reducing signs or symptoms of a disease.

Patients in need of vitamin D supplementation include healthy subjects and subjects at risk for vitamin D insufficiency or deficiency, for example, subjects with stage 1, 2, 3, 4 or 5 CKD; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D in skin during exposure to sunlight and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with an Sun Protection Factor (SPF) of 8 reduces production of vitamin D by 95%, and higher SPFs may further reduce cutaneous vitamin D production); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal and/or bypass of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenytoin, fosphenytoin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis and/or post-menopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D. Optionally excluded from the methods are therapeutic treatment of subjects suffering from renal osteodystrophy (including osteomalacia and osteitis fibrosa cystica). It is contemplated to administer any formulation described herein, including Rayaldee® extended release capsules, to such subjects.

A formulation described herein an having a particle size limit of 2.8 mm or less, or 2.5 mm or less, or 2.0 mm or less, can be administered via sprinkling (e.g., on applesauce or other soft foods, such as jellies), such that they can be swallowed without chewing. In the alternative, such formulations can be administered via an enteral feeding tube. In these embodiments, the sprinkling can be preceded by opening a capsule containing the particles, or opening a packet or sachet containing the particles. For example, an easy-opening, hard gelatin capsule is available under the trade name CONISNAP from Capsugel.

The formulation can be administered to an adult patient, or a pediatric patient. In embodiments, the pediatric patient can be 8 to 17 years of age, 12 to 17 years of age, 8 to 11 years of age, 1 month to 7 years of age, 6 months to 8 years of age, or 6 years of age or younger, or 4 years of age or younger, or 2 years of age or younger, for example.

A formulation having a particle size limit of 2.8 mm or less can be packaged with instructions for sprinkling the particles on soft foods (e.g. applesauce), and optionally also swallowing the particles and food without chewing.

A formulation having a particle size limit of 2.8 mm or less can be packaged with instructions for enteral feeding tube administration.

The formulation can be used with a dosing regimen that includes a dose reduction aspect. For example the dosing can be reduced by one unit dose (e.g. one 30 mcg unit dose) per week, as necessary, and no more frequently than at biweekly intervals, in the event that any one of the following four criteria are met: plasma iPTH is confirmed to be <35 pg/mL (for subjects with stage 3 CKD) or <70 pg/mL (for subjects with stage 4 CKD), serum calcium (corrected) is confirmed to be >10.3 mg/dL, serum total 25-hydroxyvitamin D is confirmed to be >100 ng/mL, or serum phosphorus is confirmed to be >5.5 mg/dL (ages 12 to <18 years) or >6.0 mg/dL (ages 8 to <12 years), provided that the elevated serum phosphorus is related calcifediol administration and appropriate and persistent actions have been taken to control serum phosphorus by initiating or adjusting any phosphate binder therapy.

Dose reductions can be accomplished by consistently omitting doses on a specific day of the week, for example as follows:

First dose reduction: dosing is omitted on one day of the week, e.g. all Mondays (M);
Second dose reduction: dosing is omitted two nonconsecutive days of the week, e.g. on all M and Wednesdays (W);
Third dose reduction: dosing is omitted on three nonconsecutive days of the week, e.g. all M, W and Fridays (F);
Fourth dose reduction: dosing is omitted on four days of the week, at least two or 3 of which are nonconsecutive, e.g. all M, W, F and Sundays (S);
Any subject who requires a further dose reduction terminates dosing.

As described above, the nonconsecutive days of the week can consist of or include alternating days of the week, e.g. M, W, F.

EXAMPLES

The following examples are provided for illustration and are not intended to limit the scope of the invention.

Example 1—Eudragit Polymer Formulation

Examples 1.1 to 1.4 comprising Eudragit-based polymer pellets were made by extrusion-spheronization using the excipients identified in Table 9 below. Calcifediol was dissolved in ethanol. A wet extrudable mass was prepared, extruded, and spheronized. The extrusion/spheronization process followed the general sequence described in Table 8 above. The extruder was a Caleva bench-top screen Extruder 20 having a screen size of 1 mm and operated at a speed of about 30-35 RPM. The spheronizer was a Caleva MultiBowl Spheronizer/mbs 250, operating at about 1000-2500 RPM. The sieves used for fractionation were 1.4 mm, 1.0 mm, 850 µm, 500 µm and 250 µm. Final selected pellets in different batches are: 500 µm, 850 µm and 1.0 mm). The pellets of formulation 1.2 had a mean diameter of about 500 µm, and the pellets of formulations 1.1, 1.3, and 1.4 had a mean diameter of about 1.0 mm. All pellets assayed to at least 94% of the expected API and showed satisfactory flow-properties, friability and acceptable levels of related substances impurities. The pellets contained about 4 to 6 wt. % or less water by Karl Fischer titration.

TABLE 9

| Composition | Function | 1.1 | 1.2 | 1.3 | 1.4 |
|---|---|---|---|---|---|
| Calcifediol | API | 0.03 | 0.03 | 0.03 | 0.03 |
| Miglyol 812N | Absorption Enhancer | 3.00 | 3.00 | 3.00 | 3.00 |
| MCC (Avicel PH 101) | Diluent & Spheronizing Aid | 35.47 | 40.47 | 40.47 | 40.47 |
| Eudragit RL PO | ER Polymer | 55.00 | 45.00 | 45.00 | 45.00 |
| Ethocel Standard 10 Premium | ER Polymer | x | 5.00 | 5.00 | x |
| L-HPC LH-31 | Dry Binder/Matrix Former | x | x | x | 5.00 |
| Methocel K3 Premium LV | Binding Aid | 5.00 | 5.00 | 5.00 | 5.00 |
| Caramel flavor | Flavoring Agent | 0.50 | 0.50 | 0.50 | 0.50 |
| Talc | Lubricant | 1.00 | 1.00 | 1.00 | 1.00 |
| Purified Water | Diluent for Binder | Q.S. | Q.S. | Q.S. | Q.S. |

Dissolution release properties of the pellets were measured and compared to dissolution release of a representative batch of calcifediol extended release wax-matrix extended release soft capsules. 50 mg of pellets were filled into hard capsule shells and tested for dissolution release using USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL. The dissolution results are shown in FIG. 1 and are tabulated in Table 10 below for Examples 1.1 to 1.4. The average dissolution times and Relative Standard Deviation (RSD) values were derived from dissolution testing on six capsules.

TABLE 10

| Time (h) | 1.1 Mean % released | RSD (%) | 1.2 Mean % released | RSD (%) | 1.3 Mean % released | RSD (%) | 1.4 Mean % released | RSD (%) |
|---|---|---|---|---|---|---|---|---|
| 1 | 10.33 | 6.85 | 8.62 | 9.7 | 7.35 | 9.56 | 11.45 | 9.35 |
| 2 | 19.97 | 4.45 | 18.22 | 6.23 | 15.22 | 6.03 | 24.02 | 8.43 |
| 3 | 29.70 | 5.85 | 29.17 | 5.66 | 24.46 | 4.35 | 34.66 | 8.05 |
| 4 | 40.42 | 3.92 | 38.20 | 4.94 | 32.12 | 2.92 | 44.49 | 7.48 |
| 5 | 49.39 | 4.22 | 47.00 | 6.99 | 39.51 | 2.69 | 54.50 | 8.51 |
| 6 | 59.61 | 3.6 | 55.76 | 7.47 | 46.67 | 3.51 | 64.73 | 7.38 |
| 8 | 75.72 | 4.18 | 73.01 | 6.48 | 61.64 | 3.23 | 82.58 | 7.33 |
| 10 | 92.09 | 4.53 | 84.41 | 5.74 | 75.74 | 2.18 | 91.98 | 7.01 |
| 12 | 99.72 | 2.4 | 88.20 | 5.46 | 84.63 | 2.07 | 96.06 | 6.74 |

Example 2—EC Polymer Formulation

Examples 2.1 to 2.4 comprising EC-based polymer pellets were made by extrusion-spheronization using the excipients identified in Table 11 below. A wet extrudable mass was prepared, extruded, and spheronized. The extrusion/spheronization process followed the general sequence described in Table 8 above. The extruder was a Caleva bench-top screen Extruder 20 having a screen size of 1 mm and operated at a speed of about 30-35 RPM. The spheronizer was a Caleva MultiBowl Spheronizer/mbs 250, operating at about 1000-2500 RPM. The pellets of formulations 2.1 and 2.2 had a mean diameter of about 500 μm. The pellets of formulation 2.3 had a mean diameter of about 850 μm. The pellets of formulation 2.4 had a mean diameter of about 850 μm prior to coating. Example 2.4 included a top coat comprising a 60:40 weight ratio mixture of Surelease extended release polymer and Pharmacoat 603 pore former, applied in an amount of 25% weight gain using purified water as a dispersion vehicle which was subsequently dried off. All pellets assayed to at least 93% of the expected API and showed satisfactory flow-properties, friability, and acceptable levels of related substances impurities. The pellets contained about 5.5 wt. % or less water by Karl Fischer titration.

TABLE 11

| Composition | Function | 2.1 | 2.2 | 2.3 | 2.4 |
|---|---|---|---|---|---|
| Calcifediol | API | 0.03 | 0.03 | 0.03 | 0.03 |
| Miglyol 812N | Absorption Enhancer | 3.00 | 10.00 | 5.00 | 5.00 |
| MCC (Avicel PH 101) | Diluent & Spheronizing Aid | 59.68 | 52.68 | 43.47 | 43.47 |
| Lactose, Monohydrate | Diluent & Pore Former | 25.79 | 25.79 | 35.00 | 35.00 |
| Ethocel Standard 10 Premium | ER Polymer | 5.00 | 5.00 | 5.00 | 5.00 |
| Methocel K3 Premium LV | Dry Binder | x | x | 5.00 | 5.00 |
| Methocel K3 Premium LV | Binding Aid | 5.00 | 5.00 | 5.00 | 5.00 |
| Caramel flavor | Flavoring Agent | 0.50 | 0.50 | 0.50 | 0.50 |
| Talc | Lubricant | 1.00 | 1.00 | 1.00 | 1.00 |
| Purified Water | Diluent for Binder | Q.S. | Q.S. | Q.S. | Q.S. |

Figure 2:
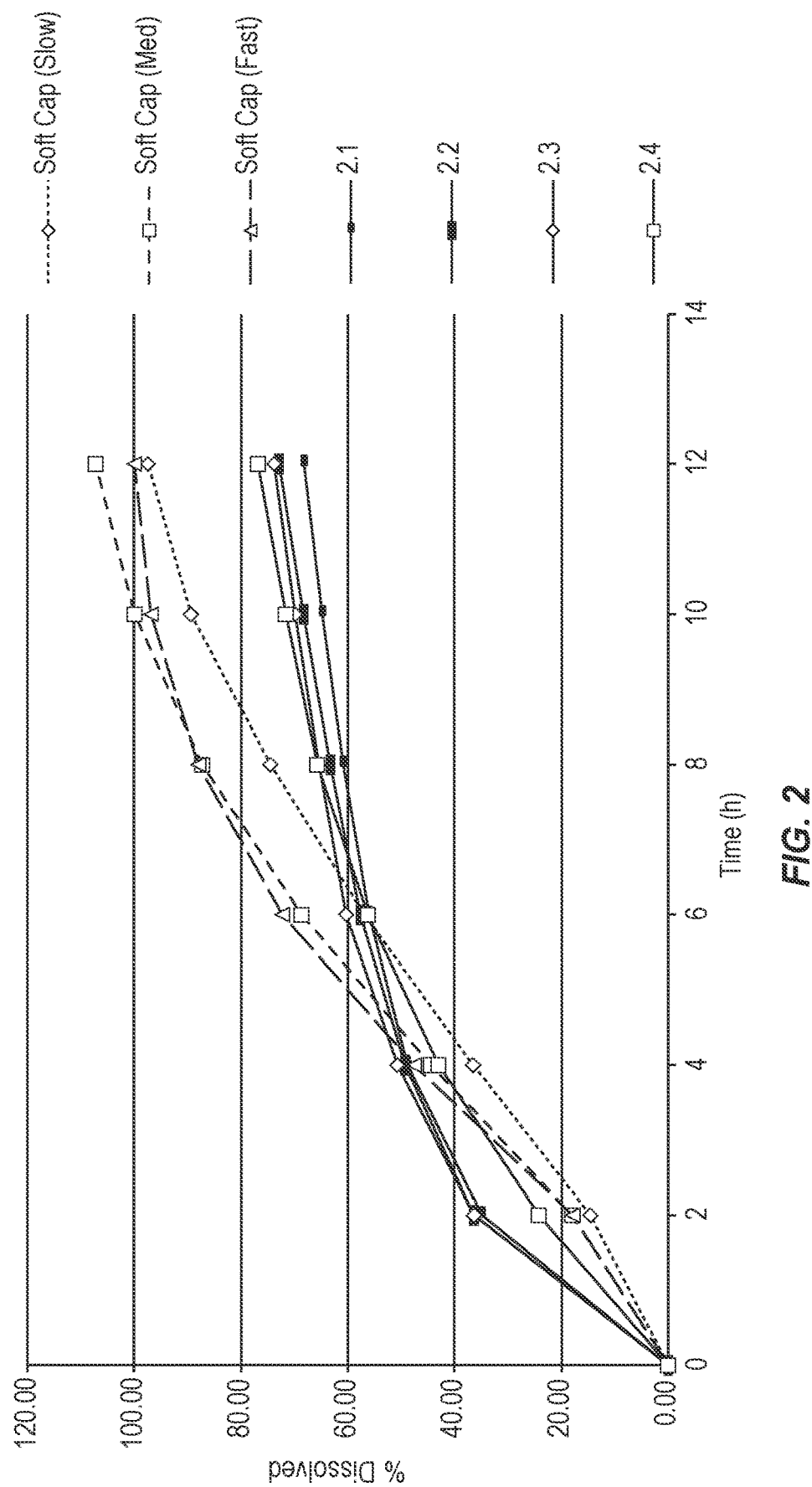
FIG. 2 shows dissolution release profiles of calcifediol-loaded, ethylcellulose (EC)-based pellets according to the disclosure herein compared to dissolution release profiles of a wax-matrix based soft capsule formulation.

Dissolution release properties of the pellets were measured and compared to dissolution release of a representative batch of calcifediol extended release wax-matrix extended release soft capsules. 50 mg of pellets were filled into hard capsule shells and tested for dissolution release using USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL. The dissolution results are shown in FIG. 2 and are tabulated in Table 12 below for Examples 2.1 to 2.4. The average dissolution times and Relative Standard Deviation (RSD) values were derived from dissolution testing on six capsules.

TABLE 12

| Time (h) | 2.1 Mean % released | RSD (%) | 2.2 Mean % released | RSD (%) | 2.3 Mean % released | RSD (%) | 2.4 Mean % released | RSD (%) |
|---|---|---|---|---|---|---|---|---|
| 1 | 24.54 | 4.4 | 24.05 | 4.85 | 21.49 | 12.39 | 9.69 | 22.99 |
| 2 | 34.89 | 2.35 | 36.38 | 7.6 | 36.35 | 8.56 | 24.25 | 15.75 |
| 3 | 43.52 | 3.36 | 43.67 | 8.08 | 44.98 | 7.49 | 34.62 | 13.26 |
| 4 | 48.81 | 1.79 | 49.24 | 8.01 | 50.68 | 7.81 | 42.97 | 9.97 |
| 5 | 52.59 | 2.46 | 53.31 | 7.74 | 55.72 | 7.30 | 49.96 | 9.19 |
| 6 | 55.96 | 1.93 | 57.62 | 7.36 | 60.28 | 6.27 | 56.21 | 8.5 |
| 8 | 60.81 | 1.64 | 63.24 | 7.75 | 65.40 | 6.27 | 65.68 | 7.47 |
| 10 | 64.75 | 1.53 | 68.27 | 7.33 | 69.85 | 5.82 | 71.57 | 6.79 |
| 12 | 68.19 | 1.42 | 72.87 | 7.73 | 73.78 | 5.55 | 76.82 | 5.81 |

Example 3—Nano/Microparticulates

A nano/microparticle formulation having 1 part by weight calcifediol, 25 parts by weight Eudragit RL PO, and 1 part by weight poly(vinyl alcohol) was prepared by an emulsion-diffusion-spray drying technique. An emulsion was formed with the API and excipients using ethyl acetate as the non-continuous phase solvent and water as the continuous phase solvent. The emulsion was homogenized and spray dried via cyclone using a Buchi Mini Spray Dryer B-191 and the general procedure and parameters described in Table 5 above. The product powder was produced in satisfactory yield had particle sizes in the range of about 900 nm to about 10 microns, including spherical to doughnut-shaped particles.

Table 13 below describes a formulation that was analyzed for dissolution.

TABLE 13

| Composition | Ratio (w.r.t. API) |
| --- | --- |
| Calcifediol | 1.00 |
| Eudragit RL PO | 25.00 |
| Poly vinyl alcohol | 1.00 |

Figure 3:
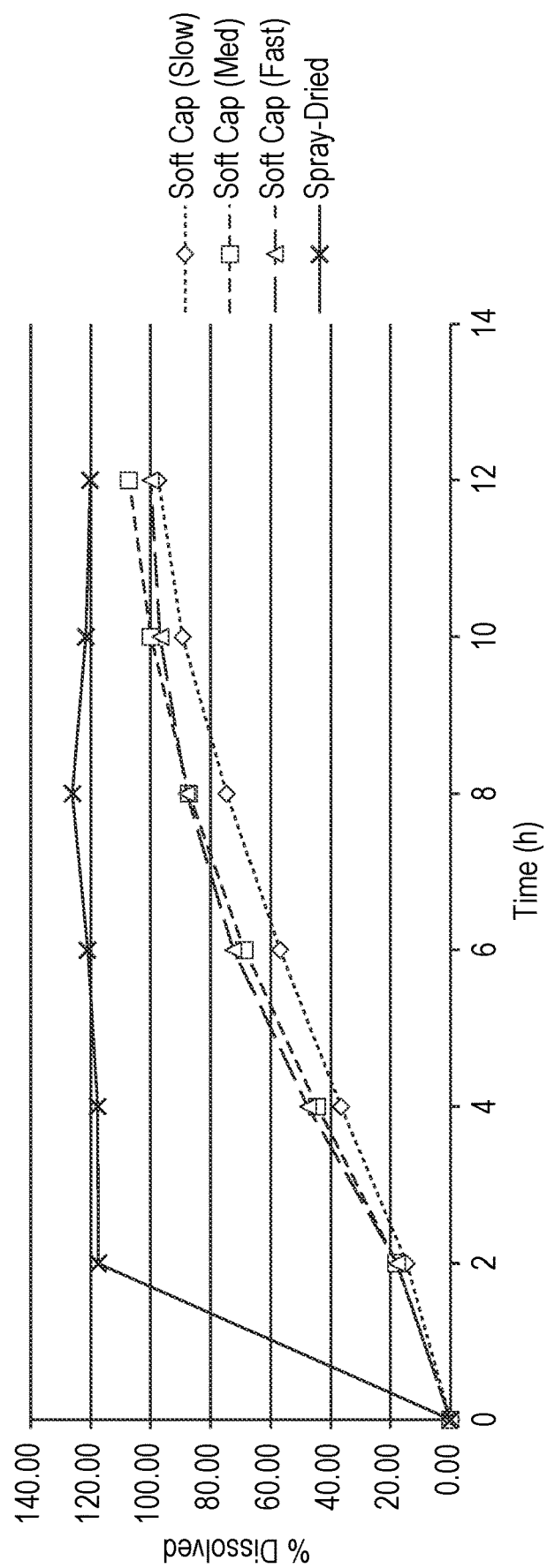
FIG. 3 shows the dissolution release profile of a spray-dried nano/microparticle formulation comprising calcifediol according to the disclosure herein compared to dissolution release profiles of a wax-matrix based soft capsule formulation.

The batch produced from the above composition produced a finely spray-dried powder with a product yield of 53%. FIG. 3 provides an initial comparison of the spray dried formulation in Table 13 compared to various slow, medium and fast batches of wax based, extended release 25-hydroxyvitamin $D_3$ capsules.

Figure 5:
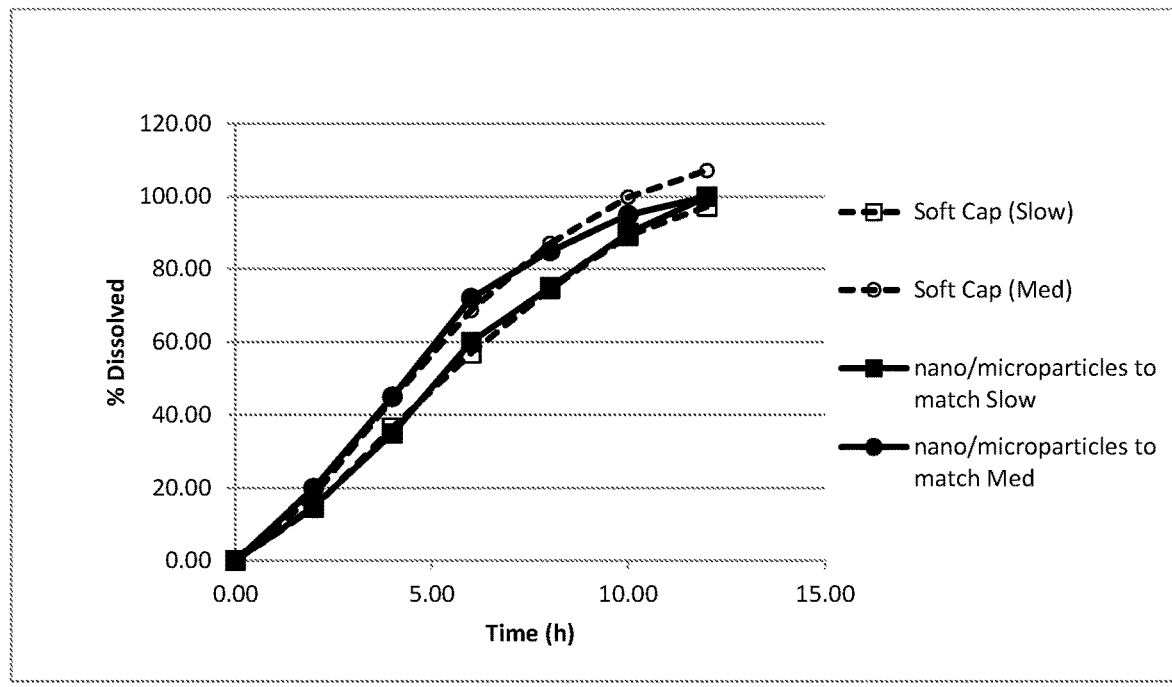
FIG. 5 shows dissolution release profiles of soft capsule wax based calcifediol formulations and nano/microparticle formulations as described in Example 3.

Additional batches of nano/microparticle formulations are made by the same process, with the formulation differences according to Table 14 below, to target the release profile of slow and medium soft capsule wax-based formulations as described above. The release profiles will be as shown in FIG. 5.

TABLE 14

| | Ratio (w.r.t. API) | |
| --- | --- | --- |
| Composition | Nano/microparticles to match Slow | Nano/microparticles to match Med |
| Calcifediol | 1.00 | 1.00 |
| Ethylcellulose | 25.00 | 15.00 |
| Poly vinyl alcohol | 1.00 | 1.00 |

Example 4—Spray-Congealing

Batches 4.1-4.13 of lipid particles comprising calcifediol with one or more lipids and optional surfactants as shown in Tables 15 and 16 below were made by spray congealing. Spray congeals were manufactured using a ProCepT spray-congealing unit in a closed loop set-up. A chiller was used to cool down the gas in the column. Nitrogen gas was used through the system in order to obtain temperatures in the system below 0° C. The temperature of the melt was kept as low as possible. The melt was sprayed by using a heated bi-fluid nozzle. Product was dosed by a pressure vessel. The process parameters used are described in Table 6 above.

Product obtained was free-flowing and in the size range ($d_{50}$) of 100 to 700 μm. Examples 4.1 to 4.9 were assayed for calcifediol content and related substances, resulting in at least 86% of the expected amount of calcifediol. Examples 4.1 to 4.9 were also assayed for water content by Karl Fischer titration, and showed about 0.3 wt. % or less water.

TABLE 15

| Composition | Function | 4.1 | 4.2 | 4.3 | 4.4 | 4.5 | 4.6 | 4.7 |
| --- | --- | --- | --- | --- | --- | --- | --- | --- |
| Calcifediol | API | 0.0150 | 0.0150 | 0.0150 | 0.0150 | 0.0150 | 0.0150 | 0.0150 |
| Paraffin | ER Agent | 41.67 | 40.65 | x | x | x | x | 21.10 |
| Glycerol monostearate 40-55 (Geleol) | ER Agent | 17.13 | 16.59 | x | x | x | x | x |
| Gelucire 44/14 | ER Agent | x | 4.26 | x | x | x | x | x |
| Gelucire 43/01 | ER Agent | x | x | 43.35 | 42.37 | x | x | x |
| Precirol ATO 5 | ER Agent | x | x | 43.35 | x | 42.37 | 21.12 | x |
| Compritol 888 ATO | ER Agent | 25.18 | 23.31 | x | 42.37 | 42.37 | 63.20 | 63.20 |
| PEG 6000 | Surfactant | x | x | x | x | x | x | x |
| Tween 80 | Surfactant | x | x | x | x | x | x | x |

TABLE 16

| Composition | Function | 4.8 | 4.9 | 4.10 | 4.11 | 4.12 | 4.13 |
| --- | --- | --- | --- | --- | --- | --- | --- |
| Calcifediol | API | 0.0150 | 0.0150 | 0.0150 | 0.0150 | 0.0150 | 0.0150 |
| Paraffin | ER Agent | x | x | x | x | x | x |
| Glycerol monostearate 40-55 (Geleol) | ER Agent | x | x | x | x | x | x |
| Gelucire 44/14 | ER Agent | x | x | x | x | x | x |
| Gelucire 43/01 | ER Agent | x | x | x | x | x | x |
| Precirol ATO 5 | ER Agent | x | 83.13 | 8.33 | 4.21 | x | 12.50 |
| Compritol 888 ATO | ER Agent | 87.24 | 83.02 | 66.65 | 75.83 | 74.98 | 66.65 |
| PEG 6000 | Surfactant | x | x | 8.33 | 4.21 | 8.33 | x |
| Tween 80 | Surfactant | x | x | x | x | x | 4.17 |

Figure 4:
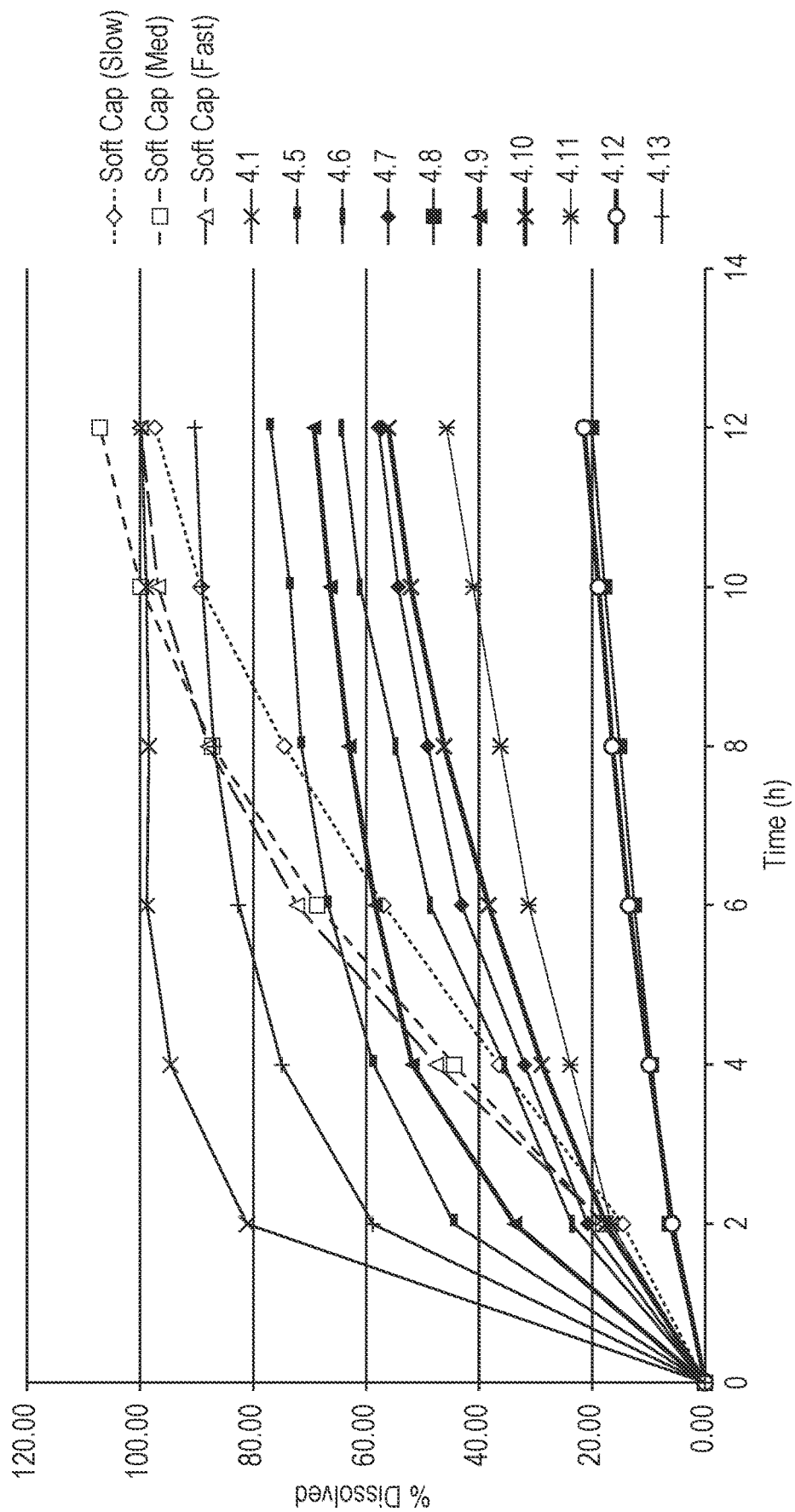
FIG. 4 shows dissolution release profiles of spray-congealed, lipid-based formulations comprising calcifediol according to the disclosure herein compared to dissolution release profiles of a wax-matrix based soft capsule formulation.

FIG. 4 shows the release profiles of multiple test formulations relative to slow, medium, and fast Soft Cap 25-hydroxyvitamin $D_3$ batches. These embodiments provided a range of release characteristics having different in vitro dissolution profiles as shown in FIG. 4, illustrating that the particular formulations used in the process can be varied to provide a desired dissolution release profile.

Example 5—Batch-to-Batch Reproducibility

Figure 6:
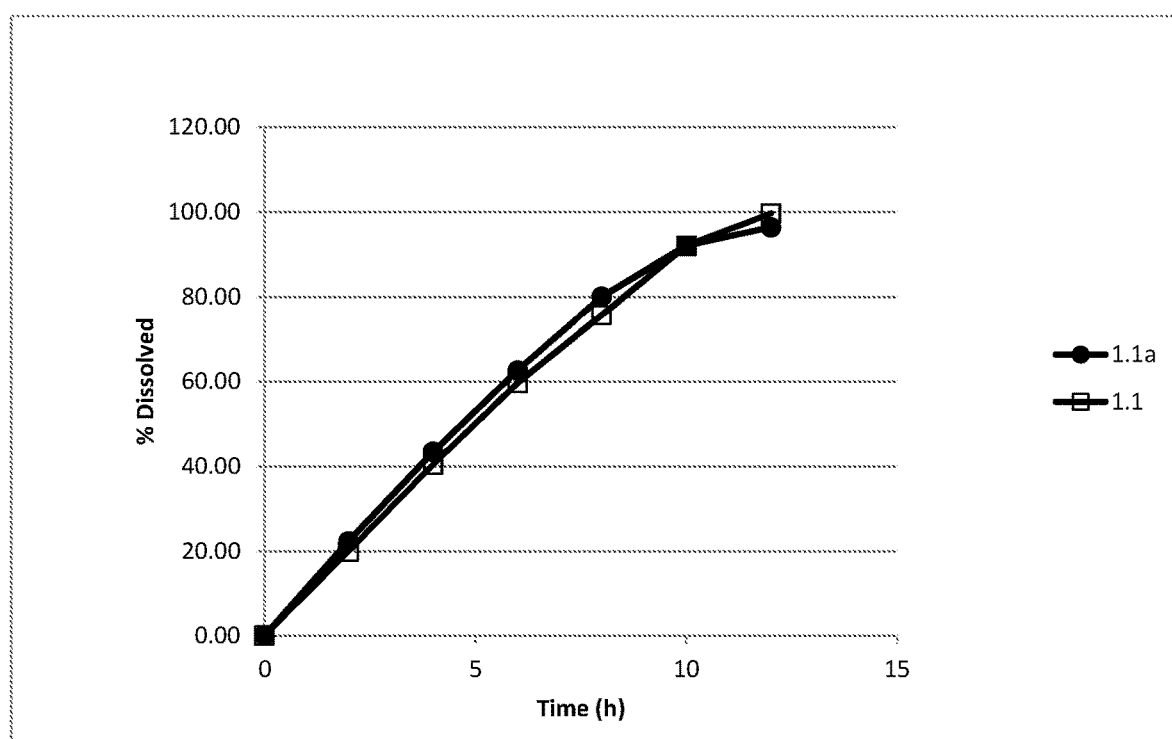
FIGS. 6-8 each show dissolution release profiles of comparable batches of Eudragit-based pellet formulations according to the disclosure herein, demonstrating batch-to-batch consistency.
Figure 7:
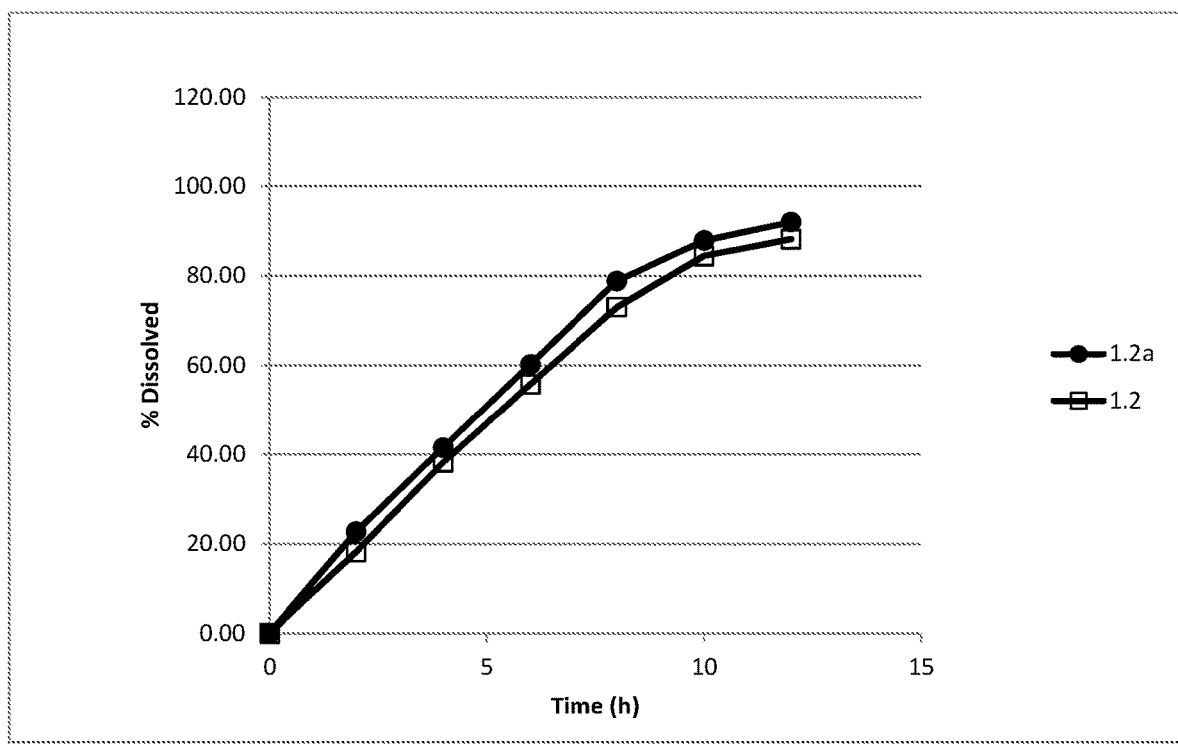
Figure 8:
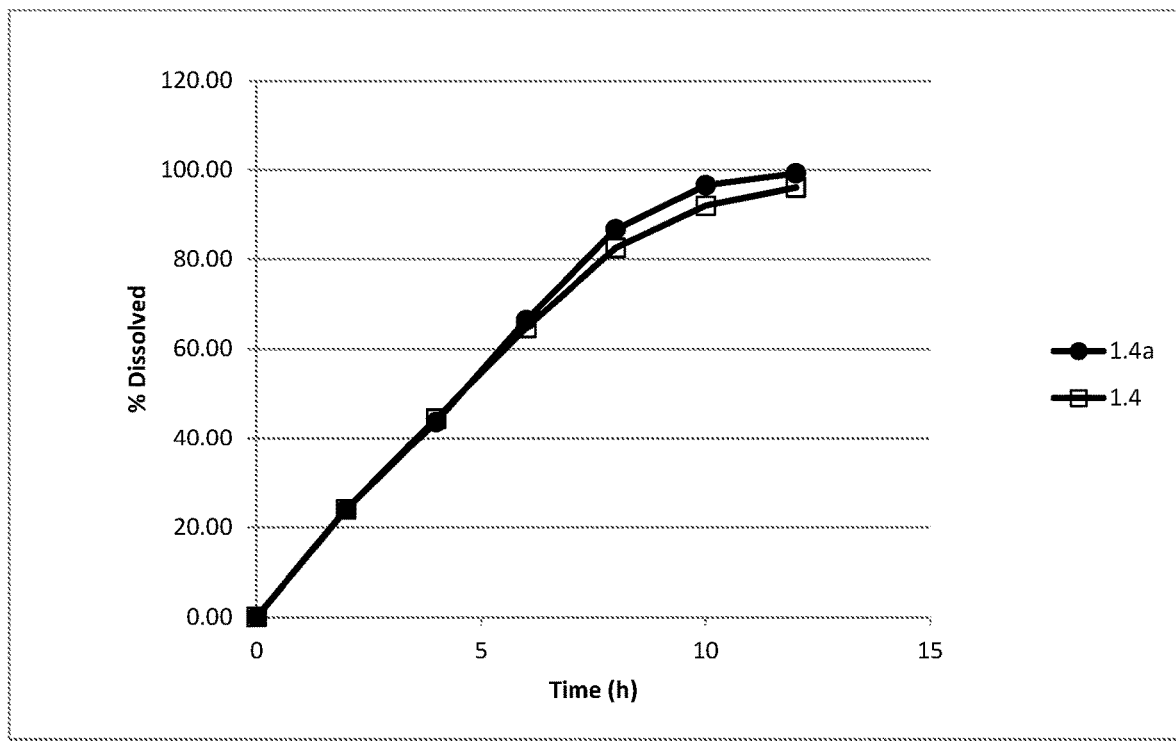

The two batches relating to the formulations of Examples 1.1, 1.2, and 1.4, above were prepared. The batches were identical except that each comparative batch omitted the flavorant (0.5 wt. %) and offset it by including an equivalent increase in the content of MCC. The dissolution properties were measured using USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL. The comparative dissolution release profiles are shown in FIGS. 6 to 8, wherein the batches without flavorant are designated 1.1a, 1.2a, and 1.4a. The results show that the formulations demonstrated good batch-to-batch consistency.

Example 6—Friability Test 10 grams of dust free pellets from each of Examples 1.1 and 2.1 were weighed out and recorded as the Before test weight ($B_{wt}$). These pellets together with 200 solid glass beads of 3 mm were placed in a Friabilator. The pellets and beads were rotated for 10 min at 25 RPM. The pellets were collected from the friabilator and dusted off by gently sieving through 250 µm sieve. The weight of pellet fractions retained on 250 µm sieve was recorded as the After test weight ($A_{wt}$). The % friability was calculated by the formula $((B_{wt}-A_{wt})/B_{wt})*100$. The results are shown in Table 17 below (three replicates), demonstrating good friability for formulations according to the disclosure herein.

TABLE 17

| Pellets Batch (Example Number) | Run | Friability (%) |
|---|---|---|
| 1.1 | 1 | 0.451 |
|  | 2 | 0.400 |
|  | 3 | 0.212 |
|  |  | Average = 0.354 |
| 2.1 | 1 | 0.384 |
|  | 2 | 0.365 |
|  | 3 | 0.527 |
|  |  | Average = 0.426 |

Example 7—In Vivo Pharmacokinetics in Minipigs

The formulations of Examples 1.1 to 1.4 and 2.1 to 2.4 were used in a single oral dose pharmacokinetic study which was performed in Naïve Male Yucatan Minipigs weighing approximately between 8 to 12 kg on Day 1. Two control arms of wax matrix-based soft-capsules (Rayaldee® type formulation) and an immediate release oral product were administered as control arms. The animals were acclimatized for at least 21 days with a 12 hours light/12 hours dark cycle to stabilize their baseline calcifediol blood levels. All animals were maintained on standardized diet from initiation of acclimation through study termination. A sample size of 5 animals per formulation was judged adequate to achieve the study objectives. Animals were food-fasted overnight for at least 10 hours and are not fed prior to dosing and for at least 4 hours after dosing. The animals were also water-fasted for an hour post-dose. Multiple baseline and post-dose administration blood samples were collected up to 120 hours after test articles administration. 25-hydroxyvitamin $D_3$ (calcifediol) concentrations in serum are assayed using a qualified method. The following pharmacokinetic parameters of calcifediol are calculated by standard noncompartmental methods: $AUC_{0-t}$: area under the concentration-time curve from time zero to the last non-zero concentration measured; $C_{max}$: maximum observed concentration; Tmax: time of observed $C_{max}$.

The study was conducted to evaluate the absorption phase of pharmacokinetic (PK) profiles of the various modified release calcifediol multiparticulate capsule formulations following a single oral dose of 270 µg in comparison to wax matrix-based, modified release soft-capsules and immediate release calcifediol products administered at 270 µg and 266 µg oral dose, respectively.

Figure 9:
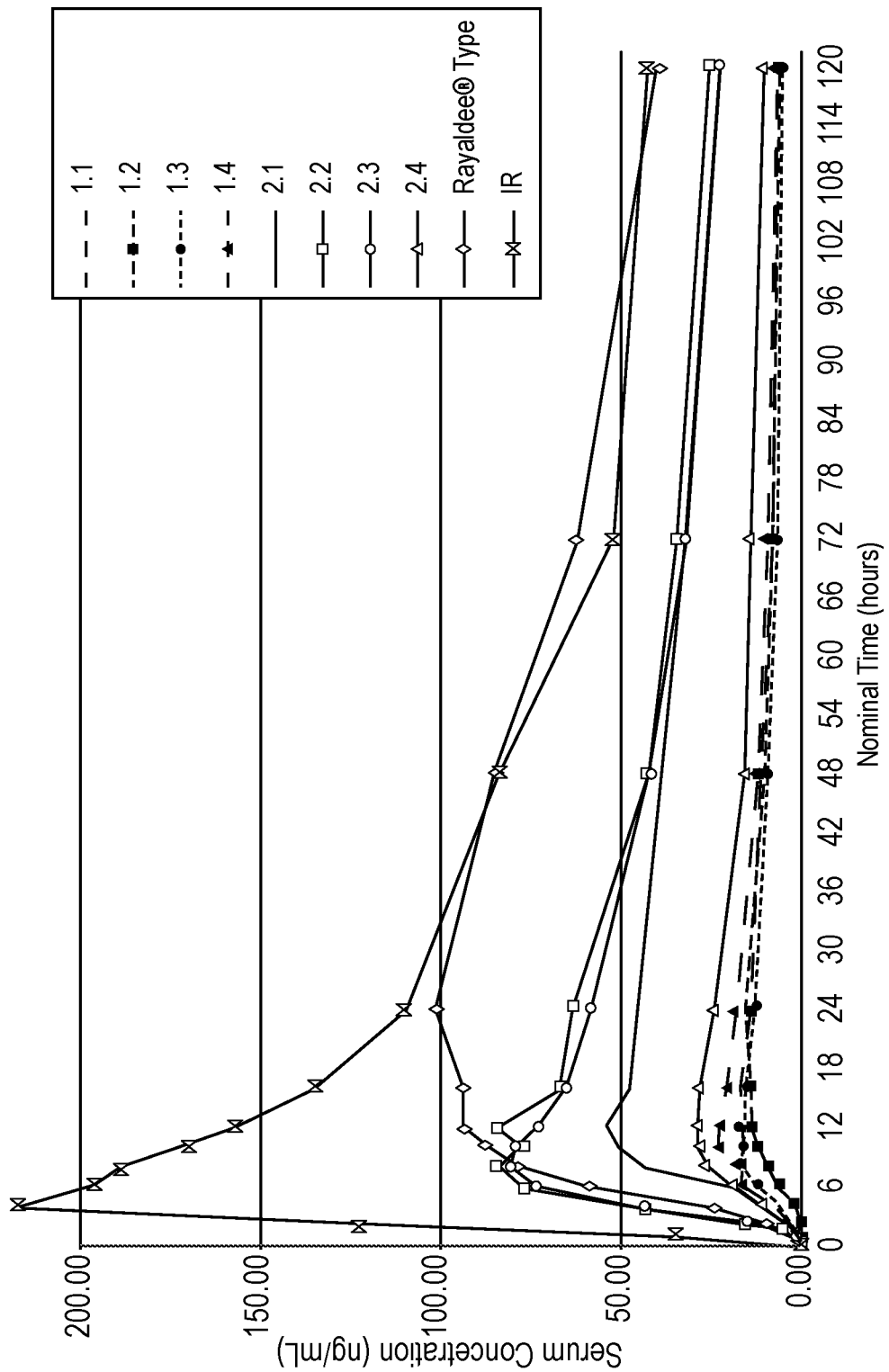
FIG. 9 shows baseline and dose corrected mean serum calcifediol concentration-time profiles for extended release formulations tested in minipigs according to Examples 1, 2, and 7.

The PK study demonstrated the promise of the pellet formulation concept in extending the release of calcifediol in vivo. The extent of absorption (AUC0-t) observed for ethylcellulose (EC)-containing formulations, especially 2.1, 2.2, and 2.3 were greater compared to the Eudragit-containing formulations (1.1 to 1.4). The median time to reach the maximum concentration (Tmax) ranged between 8 and 16 hours post-dose for all the multiparticulate formulations while the median observed Tmax was around 24 hours and 4 hours for the wax matrix-based, modified release soft-capsules 270 µg and immediate release calcifediol 266 µg, respectively. See FIG. 9 and Table 18.

TABLE 18

PK parameters of baseline corrected (BC) serum calcifediol in naïve male Yucatan minipigs

| Analyte | Parameters | 1.1 (MR 270 µg) | | | 1.2 (MR 270 µg) | | | 1.3 (MR 270 µg) | | |
|---|---|---|---|---|---|---|---|---|---|---|
| | | Mean | SD | CV | Mean | SD | CV | Mean | SD | CV |
| Calcifediol | $AUC_{0-t}$ (hr * ng/mL) | 2464.24 | 485.22 | 19.69 | 2481.85 | 153.86 | 6.20 | 2463.68 | 74.61 | 3.03 |
| | $C_{max}$ (ng/mL) | 28.80 | 7.18 | 24.94 | 26.36 | 2.22 | 8.44 | 29.82 | 1.16 | 3.88 |
| | $T_{max}$ (hr) | 12.01 | 6.00 | 15.96 | 12.05 | 9.92 | 24.48 | 12.14 | 8.07 | 16.07 |

| Analyte | Parameters | 1.4 (MR 270 µg) | | | 2.1 (MR 270 µg) | | | 2.2 (MR 270 µg) | | |
|---|---|---|---|---|---|---|---|---|---|---|
| | | Mean | SD | CV | Mean | SD | CV | Mean | SD | CV |
| Calcifediol | $AUC_{0-t}$ (hr * ng/mL) | 2684.83 | 435.41 | 16.22 | 5437.46 | 821.61 | 15.11 | 6191.60 | 1133.96 | 18.31 |
| | $C_{max}$ (ng/mL) | 34.88 | 5.65 | 16.19 | 68.01 | 12.90 | 18.97 | 99.79 | 35.73 | 35.80 |
| | $T_{max}$ (hr) | 12.03 | 8.20 | 16.08 | 12.01 | 8.24 | 24.42 | 11.98 | 8.18 | 24.40 |

TABLE 18-continued

PK parameters of baseline corrected (BC) serum calcifediol in naïve male Yucatan minipigs

| | | 2.3 (MR 270 μg) | | | 2.4 (MR 270 μg) | | | Rayaldee ®Type Soft Capsule (MR 270 μg) | | |
|---|---|---|---|---|---|---|---|---|---|---|
| Analyte | Parameters | Mean | SD | CV | Mean | SD | CV | Mean | SD | CV |
| Calcifediol | $AUC_{0-t}$ (hr * ng/mL) | 6082.46 | 621.67 | 10.22 | 3409.08 | 622.19 | 18.25 | 9388.81 | 1898.42 | 20.22 |
| | $C_{max}$ (ng/mL) | 96.96 | 24.01 | 24.76 | 43.41 | 12.64 | 29.13 | 136.89 | 40.72 | 29.75 |
| | $T_{max}$ (hr) | 8.13 | 5.96 | 24.55 | 15.98 | 7.92 | 47.99 | 24.07 | 7.91 | 48.06 |

| | | Immediate Release (IR 266 μg) | | |
|---|---|---|---|---|
| Analyte | Parameters | Mean | SD | CV |
| Calcifediol | $AUC_{0-t}$ (hr * ng/mL) | 11072.18 | 2704.85 | 24.43 |
| | $C_{max}$ (ng/mL) | 230.95 | 46.75 | 20.24 |
| | $T_{max}$ (hr) | 4.01 | 4.00 | 5.98 |

IR = Immediate-release
MR = Modified-release

The Eudragit-containing formulations extended calcifediol release in vivo (Tmax), although these particular formulations exhibited relatively lower rate and extent of absorption compared to the non-Eudragit formulation. Formulations 2.2 and 2.3 exhibited overall higher absorption profiles, out of which 2.2 had longer Tmax than 2.3. Without intending to be bound by any particular theory, it is believed that the enhanced absorption profiles of the 2.1 to 2.4 ethylcellulose formulations compared to the 1.1 to 1.4 Eudragit-containing formulations can be attributed to absorption enhancing excipients like Miglyol and soluble excipients like lactose and HPMC.

These formulations demonstrated a pellet/multiparticulate dosage form for extending the release of calcifediol in vivo.

Example 8—Additional EC Polymer Formulations

Following the studies of Example 7, another phase of formulation development work was conducted to explore the dissolution and human pharmacokinetic characteristics of polymer-based pellets produced by extrusion-spheronization. In this effort, formulation 2.2 was selected as a lead formulation and developmental trials were based around this composition.

Learning from the pig PK data in Example 7, Eudragit formulations exhibited a relatively lower rate and extent of absorption. Without intending to be bound by any particular theory, this was believed to be likely due to the lower concentration of Miglyol as well as a higher concentration of hydrophobic Eudragit polymer. As a result of the Eudragit matrix formed being hydrophobic, this might have prevented the release of hydrophobic calcifediol. However, the hydrophobic matrix was assisting in extending the release of calcifediol and thus Tmax in vivo.

On the contrary, the EC formulations displayed higher rate and extent of absorption. Without intending to be bound by any particular theory, it is believed that higher rate and extent of absorption in the EC-based formulations is attributable to the presence of a higher concentration of solubilizing excipients like Miglyol, lactose and HPMC, the presence of such soluble excipients helping the matrix to be more hydrophilic and due to this calcifediol might be absorbed better in the vicinity of this matrix.

Considering these results, the development was focused on incorporating soluble type excipients into the matrix, to facilitate solubility/absorption/bioavailability of calcifediol, and at the same time preventing this solubilized calcifediol getting too quickly released by use of extended release matrix forming agents. In addition, it was also envisaged that since calcifediol is a BCS Class-IV compound and therefore this formulation system can benefit an appropriate hydrophile-lipophile balance (HLB) and therefore, an effort was made to incorporate suitable lipid agents that satisfy this hypothesis.

To balance HLB and to prevent the matrix from being hydrophobic, Gelucire was used as a hydrophilic agent with HLB 11 to 12 and glyceryl behenate (Compritol 888 ATO) was used as a lipophilic agent with HLB 2. Other hydrophilic extended release agents such as Methocel E50 Premium LV and Methocel K4M Premium CR were also evaluated in view of achieving hydrophilic extended release matrix containing calcifediol. Gelucire was also used as a bioavailability enhancer. Gelucire 48/16 grade (PEG-32-stearate, a.k.a. PEG 32 mono and diesters of stearic and palmitic acid, with an HLB of 12 and CMC of 153±31 mg/L, which helps to increase solubility of hydrophobic and lipophobic molecules, being solid at ambient temperature with melting point of 48° C.) was adopted based on its physical properties and suitability to extrusion and spheronization process. Compritol 888 ATO was used as lipidic extended release matrix agent with a dual purpose, one was to balance lipophilicity part of HLB, i.e. it has HLB 2, and another was to provide extended-release with a non-hydrophobic matrix, as Compritol itself is an extended release agent.

Examples 8.1 to 8.28 were made by extrusion-spheronization using the excipients identified in Table 19 below. A wet extrudable mass was prepared, extruded, and spheronized. The extrusion/spheronization process followed the general sequence described in Table 8 above, by suitable modification to incorporate Comprtol 888 ATO in the dr mix and the Gelucire in the binder solution. The extruder was a Caleva bench-top screen Extruder 20 having a screen size of 1 mm and operated at a speed of about 30-35 RPM. The spheronizer was a Caleva MultiBowl Spheronizer/mbs 250, operating at about 1000-2500 RPM. The pellets had a mean diameter of about 500 μm. All pellets showed satisfactory flow-properties, friability, and acceptable levels of related substances impurities. The pellets contained about 5.5 wt. % or less water by Karl Fischer titration. Table 19 below also includes the initial assay results for calcifediol content, when obtained.

TABLE 19

| Composition | Function | 8.1 | 8.2 | 8.3 | 8.4 | 8.5 | 8.6 | 8.7 | 8.8 |
|---|---|---|---|---|---|---|---|---|---|
| Calcifediol | API | 0.03 | 0.03 | 0.03 | 0.03 | 0.03 | 0.03 | 0.03 | 0.03 |
| Miglyol 812N | Absorption Enhancer | 10.00 | 10.00 | 10.00 | 10.00 | 10.00 | 8.00 | 10.00 | 10.00 |
| BHT | Antioxidant | 0.03 | 0.03 | 0.03 | 0.03 | 0.03 | 0.03 | 0.03 | 0.03 |
| MCC (Avicel PH 101) | Diluent & Spheronizing Aid | 42.65 | 47.65 | 42.65 | 42.65 | 42.65 | 30.44 | 37.65 | 42.65 |
| Lactose, Monohydrate | Diluent & Pore Former | 25.79 | 25.79 | 25.79 | 25.79 | 25.79 | x | 25.79 | 25.79 |
| Eudragit RL PO | ER Polymer | x | x | x | x | x | 45.00 | x | x |
| Ethocel Standard 10 Premium | ER Polymer | 5.00 | 5.00 | 5.00 | 5.00 | 5.00 | x | x | 5.00 |
| L-HPC LH-31 | Dry Binder/Spheronizing Aid | x | x | x | x | x | x | x | x |
| Methocel E50 Premium LV | ER Polymer | 5.00 | x | x | x | x | x | x | 10.00 |
| Methocel K4M Premium CR | ER Polymer | x | x | 5.00 | x | x | x | x | x |
| Compritol 888 ATO | ER Agent | x | x | x | 5.00 | x | 5.00 | 15.00 | x |
| Kollidon SR | ER Agent/BA Enhancer | x | x | x | x | 5.00 | x | x | x |
| Gelucire 50/13 | ER Agent | 5.00 | 5.00 | 5.00 | x | x | x | x | x |
| Gelucire 48/16 | BA Enhancer/ER Agent | x | x | x | 5.00 | 5.00 | 5.00 | 5.00 | 5.00 |
| Methocel K3 Premium LV | Binding Aid | 5.00 | 5.00 | 5.00 | 5.00 | 5.00 | 5.00 | 5.00 | x |
| Caramel flavor | Flavoring Agent | 0.50 | 0.50 | 0.50 | 0.50 | 0.50 | 0.50 | 0.50 | 0.50 |
| Talc | Lubricant | 1.00 | 1.00 | 1.00 | 1.00 | 1.00 | 1.00 | 1.00 | 1.00 |
| Purified Water | Diluent for Binder | Q.S. | Q.S. | Q.S. | Q.S. | Q.S. | Q.S. | Q.S. | Q.S. |
| Assay | | | 106.08 | | 97.07 | 104.14 | 105.18 | 103.49 | 102.33 |

| Composition | 8.9 | 8.10 | 8.11 | 8.12 | 8.13 | 8.14 | 8.15 | 8.16 | 8.17 | 8.18 |
|---|---|---|---|---|---|---|---|---|---|---|
| Calcifediol | 0.03 | 0.03 | 0.03 | 0.03 | 0.03 | 0.03 | 0.03 | 0.06 | 0.03 | 0.03 |
| Miglyol 812N | 10.00 | 10.00 | 8.00 | 10.00 | 5.00 | 10.00 | 10.00 | 10.00 | 10.00 | 10.00 |
| BHT | 0.03 | 0.03 | 0.03 | 0.03 | 0.03 | 0.03 | x | x | 0.03 | 0.03 |
| MCC (Avicel PH 101) | 37.65 | 42.65 | 35.44 | 58.440 | 35.94 | 37.65 | 52.68 | 52.65 | 37.65 | 37.65 |
| Lactose, Monohydrate | 25.79 | 25.79 | x | 5.00 | x | 25.79 | 25.79 | 25.79 | 10.79 | 15.79 |
| Eudragit RL PO | x | x | 30.00 | x | 45.00 | x | 5.00 | x | x | x |
| Ethocel Standard 10 | 10.00 | 5.00 | 15.00 | 10.00 | x | 15.00 | 5.00 | 5.00 | 15.00 | 20.00 |

TABLE 19-continued

| Composition | 8.19 | 8.20 | 8.21 | 8.22 | 8.23 | 8.24 | 8.25 | 8.26 | 8.27 | 8.28 |
|---|---|---|---|---|---|---|---|---|---|---|
| Premium L-HPC LH-31 | x | x | x | x | x | x | x | x | x | x |
| Methocel E50 Premium LV | x | x | x | x | 5.00 | x | x | x | x | x |
| Methocel K4M Premium CR | x | 5.00 | x | x | x | x | x | x | x | x |
| Compritol 888 ATO | 5.00 | x | x | 5.00 | x | 2.50 | x | x | 15.00 | 5.00 |
| Kollidon SR | x | x | x | x | x | x | x | x | x | x |
| Gelucire 50/13 | 5.00 | 5.00 | 5.00 | 5.00 | x | x | x | x | 5.00 | 5.00 |
| Gelucire 48/16 | 5.00 | 5.00 | 5.00 | 5.00 | 2.50 | 2.50 | x | x | 5.00 | 5.00 |
| Methocel K3 Premium LV | 0.50 | 0.50 | 0.50 | 0.50 | 5.00 | 5.00 | 5.00 | 5.00 | 0.50 | 0.50 |
| Caramel flavor | 1.00 | 1.00 | 1.00 | 1.00 | 0.50 | 0.50 | 0.50 | 0.50 | 1.00 | 1.00 |
| Talc | Q.S. | Q.S. | Q.S. | Q.S. | 1.00 | 1.00 | 1.00 | 1.00 | Q.S. | Q.S. |
| Purified Water | 105.70 | 99.49 | 107.51 | 107.15 | Q.S. | Q.S. | Q.S. | Q.S. | | 106.34 |
| Calcifediol assay | | | | | 99.53 | 101.92 | 92.13 | 104.23 | | |

| Composition | 8.19 | 8.20 | 8.21 | 8.22 | 8.23 | 8.24 | 8.25 | 8.26 | 8.27 | 8.28 |
|---|---|---|---|---|---|---|---|---|---|---|
| Calcifediol | 0.03 | 0.03 | 0.03 | 0.03 | 0.030 | 0.030 | 0.030 | 0.03 | 0.03 | 0.03 |
| Miglyol 812N | 10.00 | 10.00 | 10.00 | 10.00 | 10.00 | 10.00 | 10.00 | 10.00 | 10.00 | 10.00 |
| BHT | 0.03 | 0.03 | 0.03 | x | 0.030 | 0.030 | 0.030 | 0.03 | x | 0.03 |
| MCC (Avicel PH 101) | 37.65 | 37.65 | 38.44 | 52.68 | 38.44 | 38.44 | 38.44 | 38.44 | 52.68 | 38.44 |
| Lactose, Monohydrate | 5.79 | 10.79 | 0.00 | 25.79 | 15.00 | 15.00 | 15.00 | x | 25.79 | x |
| Eudragit RL PO | x | x | x | x | x | x | x | x | x | x |
| Ethocel Standard 10 Premium | 20.00 | 15.00 | 20.00 | 5.00 | 5.00 | 5.00 | 5.00 | 20.00 | 5.00 | 20.00 |
| L-HPC LH-31 | 15.00 | 5.00 | 20.00 | x | 20.00 | 20.00 | 20.00 | 20.00 | x | x |
| Methocel E50 Premium LV | x | 10.00 | x | x | x | x | x | x | x | x |
| Methocel K4M Premium CR | x | x | x | x | x | x | x | x | x | x |
| Compritol 888 ATO | x | x | x | x | x | x | x | 5.00 | x | 20.00 |
| Kollidon SR | x | x | x | x | x | x | x | x | x | x |
| Gelucire 50/13 | 5.00 | 5.00 | 5.00 | x | 5.00 | 5.00 | 5.00 | 5.00 | x | 5.00 |
| Gelucire 48/16 | 5.00 | 5.00 | 5.00 | 5.00 | 5.00 | 5.00 | 5.00 | 5.00 | 5.00 | 5.00 |
| Methocel K3 Premium LV | 0.50 | 0.50 | 0.50 | 0.50 | 0.50 | 0.50 | 0.50 | 0.50 | 0.50 | 0.50 |
| Caramel flavor | 1.00 | 1.00 | 1.00 | 1.00 | 1.00 | 1.00 | 1.00 | 1.00 | 1.00 | 1.00 |
| Talc | Q.S. | Q.S. | Q.S. | Q.S. | Q.S. | Q.S. | Q.S. | Q.S. | Q.S. | Q.S. |
| Purified Water | | | | | | | | | | |

TABLE 19-continued

| Calcifediol assay | 107.43 | 100.25 | 95.54 | 95.44 | 53.38 | 106.78 | 102.89* | 92.04 | 98.1 | 102.5 |

*following storage at room temperature for five months

Generally, 100 mg of pellets were filled into hard capsule shells and tested for dissolution release using USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL. Example 8.16 had a higher concentration of calcifediol and a fill weight of 50 mg. The dissolution results are tabulated in Table 20 below, when available. The average dissolution time values were derived from dissolution testing on six capsules; a comparison with Rayaldee® soft capsules is provided.

TABLE 20

| Time (hr) | Rayaldee® Mean % released | 8.2 Mean % released | 8.4 Mean % released | 8.5 Mean % released | 8.6 Mean % released | 8.7 Mean % released | 8.8 Mean % released | 8.9 Mean % released |
|---|---|---|---|---|---|---|---|---|
| 0 | 0.00 | 0.00 | 0.00 | 0.00 | 0.00 | 0.00 | 0.00 | 0.00 |
| 1 | 1.85 | 46.43 | 42.83 | 44.25 | 39.67 | 59.38 | 64.17 | 55.14 |
| 2 | 10.06 | 60.48 | 56.77 | 57.26 | 84.50 | 77.69 | 85.65 | 72.28 |
| 3 | 21.98 | 67.88 | 64.53 | 64.72 | 103.62 | 86.38 | 93.59 | 81.79 |
| 4 | 34.39 | 72.91 | 69.63 | 70.44 | 107.45 | 92.90 | 98.42 | 87.41 |
| 5 | 45.99 | 77.57 | 74.17 | 74.91 | 107.98 | 96.21 | 100.40 | 92.49 |
| 6 | 55.34 | 80.34 | 77.43 | 78.58 | 108.94 | 99.67 | 102.12 | 95.60 |
| 8 | 69.28 | 86.65 | 82.80 | 84.36 | 109.15 | 102.46 | 104.16 | 101.03 |
| 10 | 78.11 | 90.09 | 86.84 | 88.56 | 109.57 | 104.13 | 104.13 | 105.05 |
| 12 | 82.3 | 92.88 | 90.34 | 92.18 | 110.48 | 105.17 | 105.02 | 106.65 |

| Time (hr) | 8.10 Mean % released | 8.11 Mean % released | 8.12 Mean % released | 8.13 Mean % released | 8.14 Mean % released | 8.15 Mean % released | 8.16 Mean % released | 8.18 Mean % released | 8.19 Mean % released |
|---|---|---|---|---|---|---|---|---|---|
| 0 | 0.00 | 0.00 | 0.00 | 0.00 | 0.00 | 0.00 | 0.00 | 0.00 | 0.00 |
| 1 | 63.94 | 35.17 | 39.17 | 20.09 | 28.05 | 23.65 | 27.89 | 35.46 | 29.32 |
| 2 | 86.20 | 71.52 | 52.90 | 35.41 | 38.83 | 33.65 | 39.44 | 48.88 | 40.93 |
| 3 | 97.14 | 92.99 | 60.76 | 49.36 | 44.74 | 40.09 | 46.96 | 57.33 | 47.66 |
| 4 | 100.23 | 101.25 | 65.95 | 64.21 | 50.02 | 45.27 | 52.72 | 63.02 | 53.28 |
| 5 | 101.76 | 104.23 | 71.48 | 79.83 | 54.26 | 48.77 | 57.58 | 68.18 | 58.04 |
| 6 | 102.88 | 105.92 | 75.47 | 91.93 | 58.07 | 51.95 | 61.77 | 72.73 | 61.54 |
| 8 | 103.76 | 108.13 | 82.26 | 102.10 | 63.78 | 57.33 | 68.68 | 79.03 | 68.19 |
| 10 | 104.69 | 109.56 | 86.42 | 104.77 | 68.91 | 62.05 | 73.71 | 83.88 | 73.98 |
| 12 | 104.44 | 110.79 | 91.50 | 106.35 | 72.27 | 65.74 | 77.75 | 88.26 | 78.96 |

| Time (hr) | 8.20 Mean % released | 8.21 Mean % released | 8.22 Mean % released | 8.23 Mean % released | 8.24 Mean % released | 8.25* Mean % released | 8.26 Mean % released | 8.27 Mean % released | 8.28 Mean % released |
|---|---|---|---|---|---|---|---|---|---|
| 0 | 0.00 | 0.00 | 0.00 | 0.00 | 0.00 | 0.00 | 0.00 | 0.00 | 0.00 |
| 1 | 30.66 | 25.84 | 21.90 | 19.31 | 41.97 | 40.50 | 23.12 | 27.20 | 26.70 |
| 2 | 42.52 | 35.59 | 31.00 | 28.02 | 57.47 | 52.50 | 32.35 | 37.90 | 36.20 |
| 3 | 49.68 | 41.83 | 37.20 | 32.66 | 66.27 | 60.90 | 38.10 | 44.70 | 43.00 |
| 4 | 55.32 | 47.06 | 41.60 | 35.55 | 72.94 | 66.80 | 42.72 | 50.60 | 48.00 |
| 5 | 60.53 | 50.16 | 45.80 | 38.05 | 77.87 | 71.20 | 46.18 | 56.30 | 52.40 |
| 6 | 63.96 | 53.50 | 48.90 | 39.57 | 82.21 | 75.10 | 49.25 | 60.60 | 56.00 |
| 8 | 71.12 | 58.80 | 54.20 | 42.75 | 88.03 | 80.50 | 54.43 | 66.90 | 62.20 |
| 10 | 76.13 | 63.67 | 58.60 | 45.30 | 92.99 | 74.50 | 58.28 | 72.20 | 67.40 |
| 12 | 80.44 | 67.55 | 61.80 | 46.69 | 96.72 | 87.70 | 61.41 | 76.10 | 71.80 |

*following storage at room temperature for five months

Initially, compared to the formulations of Examples 1 and 2, the Gelucire 48/16 was added into the binder solution and Methocel K3 Premium LV from the binder solution was replaced and added to the dry mix as a dry binder (Examples 8.1 to 8.12). Development pertaining to this process resulted in more of a burst effect, releasing 53%-86% calcifediol in 2 hours. Those trials with Gelucire 48/16 showed high solubility and rapid release of calcifediol despite failing to completely control the release profile as desired. These results favored the use of Gelucire as a bioavailability enhancer. It was observed that these pellets were relatively soft pellets and, without intending to be bound by any particular theory, it was believed that the softness of the pellets could be a reason behind burst release.

In view of the foregoing results, in subsequent trials (Examples 8.13 to 8.28) Methocel K3 Premium LV was added into the binder solution, removing it from the dry-mix. Further development with Gelucire 48/16 and Methocel K3 together in binder solution was suited well to the process and were also effective in bringing back burst release to <40% in 2 hours. It was also observed that the pellets were harder than those pellets in which the HMPC was added to the dry mix.

To compensate the enhanced solubility provided by the Gelucire, further trials were conducted with the use of Compritol and EC as an extended release agent to effectively control the release profile and to provide extended-release property to calcifediol. Some of the trials were also ranged with a lower level of lactose, and without lactose which provided slower release. As a general trend for these matrix formulations tested, it was observed that decreasing the initial release decreased the overall release as well. Therefore, a formulation was mainly optimized with 20% EC and 20% Compritol as an extended release agent and Gelucire 48/16 in 5% concentrations as a bioavailability enhancer.

Alongside this development for release characteristics was also addition of BHT antioxidant to formulations, to provide API stability to the formulation, resulting in a significant decline in related substances as shown in Table 21).

To conclude $2^{nd}$ phase development work, formulation 8.21 was selected as a second prototype formulation for a human clinical study (Example 9, below). The PK study involved total two formulation prototypes, one formulation based on conservative approach—i.e. Pig data (Formulation same as Example 2.2; new Example 8.27) and another one was a modified formulation of Example 2.2, the batches which are Examples 8.21 and 8.28.

TABLE 21

Effect of BHT on Ethylcellulose formulations

| RRT (relative-retention time) or named impurity | BHT? Example No.: | No 2.2 | Yes 8.2 | Yes 8.4 | No 8.27* |
|---|---|---|---|---|---|
| trans-CAL | | 0.354 | 0.160 | 0.120 | x |
| 0.35 | | x | <RT | x | x |
| 0.40 | | x | 0.070 | 0.050 | x |
| 0.42 | | 0.080 | x | x | x |
| 0.47 | | 0.233 | x | <RT | x |
| 0.48 | | 0.096 | x | x | 0.10 |
| 1.14 | | 0.100 | <RT | <RT | x |
| Single Largest Unknown Impurity | | 0.233 | 0.070 | 0.050 | — |
| Σ Impurity | | 0.863 | 0.230 | 0.170 | 0.32 |

*Examples 2.2, 8.2, and 8.4 were made and analyzed under similar conditions and at the same scale and thus the results are comparable. Example 8.27 was made and analyzed under different conditions, and thus the related substances results are not believed to be comparable to examples 2.2, 8.2, and 8.4.

Example 9: Single-Dose Oral Pharmacokinetic Study of Two Calcifediol 30 Mcg Pellet Formulations in Healthy Adult Human Subjects Under Fasting Conditions The objective of this study was to evaluate the pharmacokinetics of two calcifediol 30 mcg pellet formulations after a single oral dose administration to humans under fasting conditions. This single-dose study was designed in accordance with EMA and FDA regulatory guidelines, with the aim of characterizing the bioavailability and PK of calcifediol in two novel formulations in healthy subjects. The primary study endpoints evaluated the baseline-adjusted PK parameters Cmax and $AUC_{0-T}$ of calcifediol. The purpose of this study was to quantify the rate and extent of absorption from the formulations.

Figure 10:
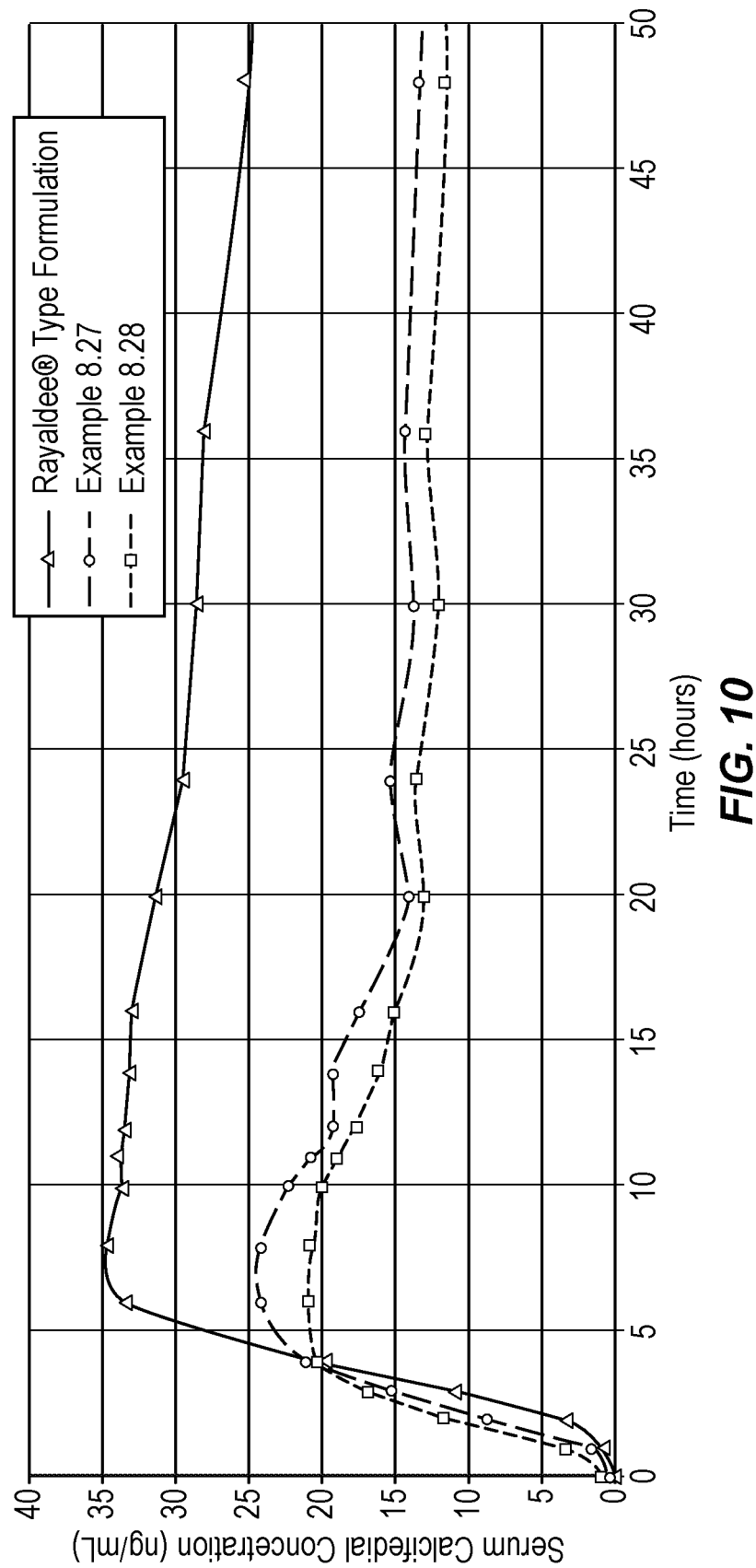
FIG. 10 shows baseline-corrected serum cacifediol concentration-time profiles for extended release formulations tested in humans according to Example 9.

Following a single oral dose administration under fasting conditions, baseline-adjusted calcifediol mean peak concentration and extent of exposure was slightly higher for the formulation of Example 8.27 compared to Example 8.28. For the formulations of Example 8.27 and Example 8.28, the mean Cmax were 25.65 ng/mL and 22.01 ng/mL, respectively, and the extent of absorption ($AUC_{0-T}$) was 2390.05 ng·h/mL and 2059.61 ng·h/mL, respectively. Time to reach peak concentrations (Tmax) was similar between both formulations, with a median Tmax of 6.00 and 6.05 hours for the formulations of Example 8.27 and Example 8.28, respectively. For unadjusted calcifediol, the same trends were observed for mean peak concentration and extent of exposure, however, the magnitude of the difference is less compared to the results of baseline-adjusted calcifediol. Overall, the formulations tested were generally safe and well-tolerated by the subjects included in this study (Refer to FIG. 10 and Table 22).

TABLE 22

Summary of baseline-adjusted pharmacokinetic parameters

| Parameter (Units) | Example 8.27 (n = 16)[b] | | Example 8.28 (n = 15)[c, d] | | Reference Rayaldee ®-type formulation | |
|---|---|---|---|---|---|---|
| | Mean | (C.V. %) | Mean | (C.V. %) | Mean | (C.V. %) |
| $C_{max}$ (ng/mL) | 25.65 | (58.2) | 22.01 | (37.0) | 42.29 | (63.2) |
| $T_{max}$ (hours)[a] | 6.00 | (3.00-10.00) | 6.05 | (3.00-11.00) | 9.51 | (4-96) |
| $AUC_{0-T}$ (ng · h/mL) | 2390.05 | (57.0) | 2059.61 | (36.4) | 4534.25 | (55.0) |
| $AUC_{0-\infty\_FDA}$ (ng · h/mL) | 6165.71 | (63.0) | 4136.67 | (56.5) | 9334.46 | (61.1) |
| $AUC_{0-T/\infty}$ (%) | 54.94 | (17.8) | 63.06 | (30.8) | 53.17 | (10.3) |
| $AUC_{0-\infty\_EMA}$ (ng · h/mL) | 6158.19 | (63.4) | 4062.91 | (55.9) | 9243.68 | (60.5) |
| Residual Area (%) | 45.16 | (21.1) | 36.37 | (51.2) | 46.37 | (11.9) |

[a]Median (range)

[b]n = 8 for $AUC_{0-\infty\_FDA}$, $AUC_{0-T/\infty}$, $AUC_{0-\infty\_EMA}$ and residual area

[c]n = 14 for $AUC_{0-T}$

[d]n = 7 for $AUC_{0-\infty\_FDA}$, $AUC_{0-T/\infty}$, $AUC_{0-\infty\_EMA}$ and residual area Example 10: Heat-Cured Formulations for Storage Stability Previous batches from Example 8 with Compritol as a matrix agent showed a decline in dissolution profiles following accelerated stability testing at 40° C. and 75% RH for 3 months period. Without intending to be bound by any particular theory, variation of drug release (decrease) observed following storage at accelerated conditions could be as a result of an altered distribution of the lipid component within the matrix structure; the lipid may migrate within the matrix structure and increase the hydrophobicity of the pellet matrix in the absence of its proper stabilization. The hydrophobicity of the matrix, in turn, reduces the rate of water diffusion into the matrix and drug diffusion out from the matrix. This can lead to slower release kinetics on stability. To reduce the decline of dissolution under these conditions, a curing/sintering step can be utilized. This additional step will stabilize the lipid in the matrix at the initial stage of formulation manufacture.

However, high-melting lipids (e.g. glyceryl behenate, Compritol 888 ATO, having a melting range of 65-77° C.) require curing at higher temperatures, and therefore curing above this temperature may degrade API (e.g. calcifediol). Therefore, relatively lower melting components with similar functionalities can be used in addition to or partially or completely in place of the relatively higher melting components. For example, glyceryl distearate/palmitostearate (e.g. Precirol ATO 5) is a lipid functionally similar to glyceryl behenate, while it has a lower melting point 54° C. Carrying out curing at 60° C. can melt Precirol in the matrix and may provide a cement-like network that will help to strengthen and stabilize the Compritol network against further changes during storage, e.g. during accelerated stability testing.

The formulation of Example 8.28 described above was varied by addition of glyceryl distearate/palmitostearate and compensating changes to other formulation ingredients, to prepare formulation Examples 10.1 to 10.5, as described in Table 23 below. Pellets were prepared as generally described above in Example 8. The Precirol component was added to the dry mix for processing.

TABLE 23

| Composition | Function | 8.28 | 10.1 | 10.2 | 10.3 | 10.4 | 10.5 |
|---|---|---|---|---|---|---|---|
| Calcifediol | API | 0.03 | 0.03 | 0.03 | 0.03 | 0.03 | 0.03 |
| Miglyol 812N | Absorption Enhancer | 10.00 | 10.00 | 10.00 | 10.00 | 10.00 | 10.00 |
| BHT | Antioxidant | 0.03 | 0.03 | 0.03 | 0.03 | 0.03 | 0.03 |
| MCC (Avicel PH 101) | Diluent & Spheronizing Aid | 38.44 | 38.44 | 38.44 | 38.44 | 33.44 | 38.44 |
| Ethocel Standard 10 Premium | ER Polymer | 20.00 | 10.00 | 12.50 | x | 17.50 | 20.00 |
| Ethocel Standard 100 Premium | ER Polymer | x | x | x | 12.50 | x | x |
| Compritol 888 ATO | ER agent | 20.00 | 20.00 | 22.50 | 22.50 | 22.50 | 15.00 |
| Precirol ATO 5 | ER Aid/Matrix Reinforcer | X | 10.00 | 5.00 | 5.00 | 5.00 | 5.00 |
| Gelucire 48/16 | BA Enhancer/ER Agent | 5.00 | 5.00 | 5.00 | 5.00 | 5.00 | 5.00 |
| Methocel K3 Premium LV | Binding Aid | 5.00 | 5.00 | 5.00 | 5.00 | 5.00 | 5.00 |
| Caramel flavor | Flavoring Agent | 0.50 | 0.50 | 0.50 | 0.50 | 0.50 | 0.50 |
| Talc | Lubricant | 1.00 | 1.00 | 1.00 | 1.00 | 1.00 | 1.00 |
| Purified Water | Diluent for Binder | Q.S. | Q.S. | Q.S. | Q.S. | Q.S. | Q.S. |

The resulting pellets of Examples 10.1 and 10.2 were tested for dissolution profiles as described in Example 8 above, either in their uncured state or following curing at 60° C. for defined times, as tabulated in Table 24 below with the initial dissolution results.

TABLE 24

| Time (hr) | 8.28 (uncured) Mean % released | 10.1 (uncured) Mean % released | 10.1 (cured 1 hr) Mean % released | 10.2 (uncured) Mean % released | 10.2 (cured 1 hr) Mean % released | 10.2 (cured 2 hr) Mean % released | 10.2 (cured 3 hr) Mean % released |
|---|---|---|---|---|---|---|---|
| 0 | 0.00 | 0.00 | 0.00 | 0.00 | 0.00 | 0.00 | 0.00 |
| 1 | 26.70 | 50.20 | 49.10 | 34.80 | 34.30 | 28.80 | 23.80 |
| 2 | 36.20 | 64.20 | 63.20 | 46.80 | 47.90 | 48.20 | 45.30 |
| 3 | 43.00 | 73.10 | 72.10 | 55.30 | 56.90 | 57.10 | 54.30 |
| 4 | 48.00 | 79.40 | 78.00 | 61.70 | 63.30 | 63.40 | 60.30 |
| 5 | 52.40 | 83.50 | 82.30 | 66.70 | 68.30 | 68.30 | 65.00 |
| 6 | 56.00 | 86.90 | 85.40 | 70.70 | 72.30 | 72.30 | 68.80 |
| 8 | 62.20 | 90.70 | 89.20 | 76.70 | 78.40 | 78.10 | 74.40 |
| 10 | 67.40 | 93.30 | 91.80 | 81.70 | 83.10 | 82.80 | 79.00 |
| 12 | 71.8 | 95.00 | 93.50 | 85.50 | 86.80 | 86.20 | 82.60 |

As shown in Table 24, although curing showed some decrease in the release, however the curing did not substantially alter the initial release profiles of the formulations.

Following storage at accelerated stability conditions, i.e. 40° C. and 75% RH, the cured formulations will show release profiles which are more similar to the initial release profiles, whereas the uncured formulations will tend to show decreased release profiles due to unstabilized lipids present in the formulations.

Example 11: Pediatric Study

A phase 3, multi-center, randomized, double-blind, placebo-controlled study is conducted primarily or entirely within the United States (US). The study involves approximately 108 eligible subjects, balanced for gender and CKD stage, having ages of 8 to <18 years, secondary hyperparathyroidism (SHPT), stage 3 or 4 CKD, and vitamin D insufficiency (VDI). Approximately 72 subjects having ages of 12 to <18 years are enrolled initially (Cohort 1) and another approximately 36 subjects having ages of 8 to <12 years are enrolled (Cohort 2). Subjects in both cohorts are randomized in a 2:1 ratio into two treatment groups to receive a daily bedtime dosage of (a) a calcifediol extended release formulation described herein, or (b) matching placebo for 26-weeks. Subjects in Cohort 1 who are assigned to treatment with the calcifediol formulation start dosing at 30 mcg/day and, at the end of 12-weeks of treatment, undergo upward dose titration to 60 mcg per day provided that (a) plasma iPTH has not decreased by at least 30% from pretreatment baseline, (b) serum calcium (corrected for albumin) is <9.8 mg/dL, (c) serum phosphorus is ≤5.5 mg/dL and (d) serum total 25-hydroxyvitamin D is ≤65 ng/mL. The initial dosage in Cohort 2 is determined based on an interim analysis of data obtained from Cohort 1, as described below. The efficacy of the calcifediol formulation in treating SHPT is assessed from multiple plasma iPTH and serum 25-hydroxyvitamin D levels obtained in the efficacy assessment period (EAP), defined as the last 6 weeks of the 26-week treatment period.\

An Interactive Response System (IRS) provides study treatment group assignments (using a computer-generated randomization code provided by the IRS vendor) and dosing adjustments. An independent, unblinded Data Safety Monitoring Board (DSMB) is established to oversee the IRS and verify the appropriateness of all dosing adjustments, and to monitor subject safety and the effectiveness of the calcifediol formulation at regular intervals.

Members of the DSMB also conduct periodic reviews of study conduct to verify that all required data are captured to a sufficiently high degree (>95%) and within specified time frames (usually within 5 days), and to promptly recommend appropriate corrective actions to address any noted deficiencies, in an effort to minimize missing data. Specific responsibilities and activities of the DSMB are defined in the charter ratified at the pre-study organizational meeting. These responsibilities include the completion of an interim analysis of the data obtained from Cohort 1 to justify a starting dose for Cohort 2, and an interim analysis of the data obtained from Cohort 2 to justify a starting dose for a separate phase 2 study in subjects having ages of 1 month to <8 years.

Subjects receiving treatment prior to study enrollment with calcitriol or another 1α-hydroxylated vitamin D analog, or calcimimetics prior to study enrollment forgo further dosing with these agents for the duration of the study and complete an 8-week washout period prior to baseline assessments.

Subjects receiving vitamin D supplementation at a rate above 1,700 IU/day or 50,000 IU (1,250 mcg) per month prior to study enrollment reduce the dose to ≤1,700 IU/day for the duration of the study and undergo an 8-week washout period prior to baseline assessments if serum total 25-hydroxyvitamin D is ≥30 ng/mL. The washout period is unnecessary if serum total 25-hydroxyvitamin D is <30 ng/mL. Subjects complete a 6-week follow-up (FU) period after completing the 26-week treatment period or after early termination (ET).

Blood samples are collected at weekly, biweekly or monthly intervals during the 10-week pre-treatment screening/baseline period, the 26-week treatment period and the 6-week posttreatment FU period. Sparse PK samples are collected from all subjects on Day 83 at 0 (pre-dose), 6, 12, 24 hours (Day 84 pre-dose) and 48 hours (Day 85 pre-dose). Additional PK blood samples are collected in both Cohort 1 and Cohort 2 in subsets of 10 subjects treated with the calcifediol formulation and 5 subjects treated with placebo during the last 3 days of the 12th week of treatment (prior to dose titration). The additional PK samples are collected as follows: Day 83: −2, 2, 4 and 8 hours. End of study PK blood samples are collected in other subsets of approximately 20 subjects (20 subjects from each cohort) during the posttreatment FU period. In each cohort, an attempt is made to collect PK samples from 10 subjects on each ending daily dose level (30 or 60 mcg) of the calcifediol formulation, in order to establish the terminal elimination half-lives (t½) of 25-hydroxyvitamin $D_3$ at each of these dose levels.

All subjects, study personnel and the sponsor are blinded to the administered treatments and to plasma iPTH, serum total 25-hydroxyvitamin D and serum 25-hydroxyvitamin $D_3$ data until the last subject completes 26 weeks of treatment. Unblinded data are provided to all study sites in the final clinical study report.

An interim analysis of data obtained from the 15 subjects in Cohort 1 who provide intensive PK samples during the last three days of treatment week 12 is undertaken by the DSMB to determine the appropriate starting dose for Cohort 2. A second interim analysis of data obtained from 15 subjects in Cohort 2 who provide intensive PK samples during the last three days of treatment week 12 is undertaken by the DSMB to determine the appropriate starting dose for a separate phase 2 study in subjects of ages 1 month to <8 years.

Each subject participates in the study for up to approximately 42 weeks (2-weeks screening/baseline, 8-weeks washout, if required, 26-weeks of treatment with the calcifediol formulation or matching placebo, and 6-weeks of FU evaluation).

Key parameters monitored at regular intervals during the study include: plasma iPTH, serum calcium (corrected for serum albumin), serum phosphorus, serum CaxP product, serum total 25-hydroxyvitamin D, serum 25-hydroxyvitamin $D_3$, and urine calcium:creatinine ratio. Vital signs (VS) and adverse events (AEs) are monitored at each study visit. Other parameters monitored less frequently include brief physical examinations (PEs), clinical laboratory tests (hematology and clinical and urine chemistries) and patient-reported palatability and acceptability. Twelve-lead electrocardiograms (ECGs) are obtained at baseline and at the end of treatment or ET. Additional exploratory parameters, including serum 1,25-dihydroxyvitamin $D_3$, serum 24,25-dihydroxyvitamin $D_3$, plasma FGF23 and serum bone markers (Bone-specific alkaline phosphatase (BAP), C-terminal telopeptide of type 1 collagen (CTx), Procollagen type 1 N-terminal propeptide (P1NP), and Tartrate-resistant acid phosphatase 5b (TRAP 5b)), are monitored at specified intervals.

Subjects in Cohort 1 receive two unit doses (e.g. capsules) and/or matching placebo unit doses every day at bedtime to achieve the targeted initial daily dose of 30 mcg of calcifediol (one calcifediol formulation plus one placebo formulation) or 0 mcg of calcifediol (two placebo unit doses). Any food intake within 60 minutes of medication administration is recorded. At the end of 12 weeks of treatment, subjects assigned to active treatment undergo upward dose titration to 60 mcg per day (two calcifediol unit doses) provided that (a) plasma iPTH has not decreased by at least 30% from pretreatment baseline, (b) corrected serum calcium is <9.8 mg/dL, (c) serum phosphorus is ≤5.5 mg/dL and (d) serum total 25-hydroxyvitamin D is ≤65 ng/mL. Subjects in Cohort 2 receive a starting daily bedtime dose determined on the basis of the interim analysis of data obtained in Cohort 1, and undergo upward dose titration to a new daily dose that is two times higher than the starting dose at the end of 12 weeks of treatment, provided that (a) plasma iPTH has not decreased by at least 30% from pretreatment baseline, (b) corrected serum calcium is <9.8 mg/dL, (c) serum phosphorus is >6.0 mg/dL and (d) serum total 25-hydroxyvitamin D is ≤65 ng/mL.

Subjects in both Cohorts reduce the dose by one capsule per week, as necessary, and no more frequently than at biweekly intervals, in the event that any one of the following four criteria are met: plasma iPTH is confirmed to be <35 pg/mL (for subjects with stage 3 CKD) or <70 pg/mL (for subjects with stage 4 CKD), serum calcium (corrected) is confirmed to be >10.3 mg/dL, serum total 25-hydroxyvitamin D is confirmed to be >100 ng/mL, or serum phosphorus is confirmed to be >5.5 mg/dL (ages 12 to <18 years) or >6.0 mg/dL (ages 8 to <12 years), provided that the investigator has deemed the elevated serum phosphorus to be related to study drug administration and has taken appropriate and persistent actions to control serum phosphorus by initiating or adjusting any phosphate binder therapy.

Dose reductions are accomplished by consistently omitting doses on a specific day of the week, as follows:
  First dose reduction: dosing is omitted on all Mondays (M).
  Second dose reduction: dosing is omitted on all M and Wednesdays (W)
  Third dose reduction: dosing is omitted on all M, W and Fridays (F)
  Fourth dose reduction: dosing is omitted on all M, W, F and Sundays (S)

Any subject who requires a further dose reduction terminates dosing with study drugs and immediately commences the 6-week FU period.

Subjects on dose reduction are allowed an unscheduled safety visit if deemed appropriate by the investigator to have FU blood sampling within 48 hours of any dose reduction.

A summary of the initial and reduced weekly dose levels, in mcg units, after each of the four possible dose reductions appears in Table 23 below:

TABLE 23

| Daily (mcg) | Weekly (mcg) | Weekly Dose (mcg) | | | |
|---|---|---|---|---|---|
| | | 1st Reduction | 2nd Reduction | 3rd Reduction | 4th Reduction |
| 60 | 420 | 360 | 300 | 240 | 180 |
| 30 | 210 | 180 | 150 | 120 | 90 |
| 0 | 0 | 0 | 00 | 0 | 0 |

Subjects suspend dosing if plasma iPTH is persistently <30 pg/mL (three consecutive visits) or serum calcium (corrected) is confirmed to be >11.0 mg/dL, and resume when iPTH is ≥35 pg/mL and serum calcium is <9.8 mg/dL at the next lower dose level.

The primary estimand is the reduction of mean plasma iPTH by at least 30% from pretreatment baseline. The primary efficacy endpoint is the proportion of subjects in the intent-to-treat (ITT) population (age 8 to <18 years) attaining a mean decrease in plasma iPTH of at least 30% from pre-treatment baseline compared to placebo during the EAP.

Safety and tolerability are evaluated in the safety population by AEs, PEs, VS, hematology and clinical chemistries, and ECGs.

For the interim analysis, repeated-dose (steady-state) PK determinations are performed in subsets of subjects in both Cohort 1 and Cohort 2 by analyzing serum 25-hydroxyvitamin $D_3$ concentrations versus time recorded during dosing with the calcifediol formulation (n=10) or placebo (n=5) in the last three days of the $12_{th}$ week of treatment.

For the final analysis, repeated-dose (steady-state) PK determinations are performed in both Cohort 1 and Cohort 2 by analyzing serum 25-hydroxyvitamin $D_3$ concentrations versus time recorded (a) during dosing with calcifediol or placebo in the last three days of the $12_{th}$ week of treatment and (b) after the last administered dose in each active treatment group.

The following PK parameters are calculated using observed and baseline-adjusted 25-hydroxyvitamin $D_3$ concentrations: (a) area under the concentration curve (AUC), maximum concentration, ($C_{max}$), time to maximum concentration ($t_{max}$), and steady-state concentration ($C_{ss}$); and (b) $t_{1/2}$, clearance (CL/F) and volume of distribution (Vd/F), as feasible. Relative exposure and dose proportionality are examined.

Secondary efficacy endpoints include the proportion of subjects in the per-protocol (PP) population attaining a mean decrease in plasma iPTH of at least 30% from pre-treatment baseline during the EAP and the proportions of subjects in the ITT and PP populations attaining a mean serum total 25-hydroxyvitamin D of at least 30 ng/mL, in aggregate and by mean weekly study dose in the EAP. Additional secondary endpoints include the time courses of mean absolute changes from pre-treatment baseline in serum total 25-hydroxyvitamin D and plasma iPTH; PD effects on mean serum calcium (corrected), serum phosphorus, serum CaxP product, and the urine calcium:creatinine ratio; the proportion of subjects in each treatment group with hypercalciuria (>200 mg calcium/g creatinine), hypercalcemia (2 consecutive visits with serum calcium >10.3 mg/dL) or hyperphosphatemia (2 consecutive visits with serum phosphorus >5.5 mg/dL (ages 12 to <18 years) or >6.0 mg/dL (ages 8 to <12 years), deemed to be study drug related); and the proportion of subjects who attain 2 consecutive plasma iPTH values ≤70 pg/mL.

Exploratory endpoints include treatment-related changes in serum FGF23, serum BAP, serum CTx, serum P1NP, serum 1,25-dihydroxyvitamin $D_3$, serum 24,25-dihydroxyvitamin D and serum TRAP 5b.

Aspects of the description include the following numbered paragraphs A1 to A100:

A1. An extended release vitamin D formulation, comprising a vitamin D compound, optionally 25-hydroxyvitamin D or calcifediol, dispersed in a polymer composition.

A2. The formulation of aspect A1, wherein the polymer composition comprises a polymer which is water-insoluble and water permeable.

A3. The formulation of aspect A2, wherein the polymer comprises a methacrylic acid polymer.

A4. The formulation of aspect A3, wherein the polymer comprises poly(ethyl acrylate, methyl methacrylate).

A5. The formulation of aspect A2, wherein the polymer comprises an ethylcellulose.

A6. The formulation of aspect A2, wherein the polymer comprises a low-substituted hydroxypropyl cellulose polymer.

A7. The formulation of aspect A2, wherein the polymer comprises a polyvinyl acetate polymer.

A8. The formulation of aspect A1, wherein the vitamin D compound-containing composition is disposed with a release-controlling membrane.

A9. The formulation of aspect A8, wherein the release-controlling membrane comprises a water-soluble polymer.

A10. The formulation of aspect A8, wherein the release-controlling membrane comprises a mixture of a water-insoluble polymer and a pore-former.

A11. The formulation of aspect A10, wherein the water-insoluble polymer is present in an amount exceeding the amount of pore former.

A12. The formulation of any one of the preceding aspects, wherein the composition is in the form of a spheronized pellet.

A13. The formulation of any one of the preceding aspects, wherein the vitamin D compound is 25-hydroxyvitamin D and/or 25-hydroxyvitamin $D_3$.

A14. The formulation of aspect A13, wherein the vitamin D compound is 25-hydroxyvitamin $D_3$.

A15. A spheronized pellet formulation comprising 25-hydroxyvitamin D and a pharmaceutically acceptable excipient.

A16. The formulation according to aspect A15, wherein the pharmaceutically acceptable excipient comprises an extended release polymer.

A17. The formulation according to aspect A16, wherein the extended release polymer is one or more selected from the group of Eudragit RL PO, Eudragit RS PO, ethylcellulose, and Kollidon SR.

A18. The formulation according to any one of aspects A16 to A17, further comprising at least one pharmaceutically acceptable excipient selected from one or more in the group of a diluent, an absorption enhancer, and a binder.

A19. The formulation according to aspect A18, wherein the diluent is selected from one or more in the group of lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dehydrate.

A20. The formulation according to aspect A19, wherein the diluent is a pore former.

A21. The formulation according to aspect A18 or A19, wherein the absorption enhancer is selected from one or more in the group of triglycerides, medium chain triglycerides, caprylocaproyl macrogolglycerides, and polyglycolized glycerides.

A22. The formulation according to any one of aspects A18 to A21, wherein the binder is selected from one or more in the group of low-viscosity, hydrophilic cellulose ethers, PVP, carboxymethyl cellulose, starch, pregelatinized starch, acacia, tragacanth, gelatin, sodium alginate, and low-substituted hydroxypropyl cellulose.

A23. The formulation according to any one of aspects A18 to A22, wherein the diluent is a spheronizing aid, optionally MCC.

A24. The formulation according to any one of aspects A18 to 22, wherein the binder is a spheronizing aid, optionally low-substituted hydroxypropyl cellulose.

A25. The formulation of any one of the preceding aspects, wherein a particle, granule, or spheronized pellet is characterized by a friability which is not more than 1.0%, or less than 1.0%.

A26. The formulation of any one of the preceding aspects, wherein the 25-hydroxyvitamin D is 25-hydroxyvitamin $D_3$.

A27. An extended release vitamin D formulation, comprising a vitamin D compound dispersed in a fatty acid glyceride mixture.

A28. The formulation of aspect A27, wherein the fatty acid glyceride mixture comprises glyceryl behenate.

A29. A nano/microparticle formulation comprising 25-hydroxyvitamin D and a pharmaceutically acceptable excipient.

A30. The nano/microparticle formulation according to aspect A29, wherein the pharmaceutically acceptable excipient is an extended release polymer.

A31. The nano/microparticle formulation according to aspect A29, wherein the excipient comprises an insoluble polymer and a stabilizer.

A32. The nano/microparticle formulation according to aspect A31, wherein the insoluble polymer is selected from a methacrylate polymer.

A33. The nano/microparticle formulation according to aspect A31 or A32, wherein the stabilizer comprises polyvinyl alcohol.

A34. The nano/microparticle formulation according to any one of aspects A29 to A33, characterized by a mean particle size in a range of 100 nm to 10 microns, or 900 nm to 10 microns.

A35. The formulation of any one of the preceding aspects, wherein the vitamin D compound is 25-hydroxyvitamin D and/or 25-hydroxyvitamin $D_3$.

A36. The formulation of aspect A35, wherein the vitamin D compound is 25-hydroxyvitamin $D_3$.

A37. A lipid microparticle formulation comprising 25-hydroxyvitamin D, optionally calcifediol, and a pharmaceutically acceptable lipid.

A38. The lipid microparticle formulation according to aspect A37 wherein the pharmaceutically acceptable excipient is lipid which is solid or semi-solid at room temperature.

A39. A non-pareil seed formulation comprising 25-hydroxyvitamin D and a pharmaceutically acceptable excipient.

A40. The formulation of aspect A39, wherein the pharmaceutically acceptable excipient comprises an extended release polymer coating.

A41. An extended release dosage form comprising an uncoated granule, particle or pellet, said uncoated granule, particle or pellet comprising a vitamin D compound and an extended release agent.

A42. The extended release dosage form according to aspect A41, wherein the vitamin D compound is selected from 25-hydroxyvitamin D.

A43. The extended release dosage form according to aspect A41 or A42, wherein the extended release agent is selected from the group consisting of a water insoluble polymeric component.

A44. The extended release dosage form according to aspect A43, wherein the water insoluble polymeric component comprises a pH-independent swelling property and is permeable and/or dispersible.

A45. The extended release dosage form according to aspect A43, wherein the polymeric component is selected from an ammonioalkyl methacrylate copolymer.

A46. The extended release dosage form according to any one of aspects A43 to A45, wherein the polymeric component comprises ethyl cellulose.

A47. The extended release dosage form according to any one of aspects A43 to A46, wherein the polymeric component comprises a blend of PVA and PVP.

A48. The extended release dosage form according to any one of aspects A43 to A47, further including a lipophilic compound.

A49. The extended release dosage form according to any one of aspects A41 to A48, in the form of a spheronized pellet.

A50. The extended release dosage form according to any one of aspects A42 to A49, wherein the 25-hydroxyvitamin D is 25-hydroxyvitamin $D_3$.

A51. A pharmaceutical composition comprising 25-hydroxyvitamin D, optionally calcifediol, and a pharmaceutically acceptable excipient selected from one or more excipients in the group of an absorption enhancer, a spheronizing aid, a water insoluble polymer, and a binder.

A52. The pharmaceutical composition according to aspect A51, wherein the absorption enhancer is selected from one or more in the group of triglycerides, medium chain triglycerides, caprylocaproyl macrogolglycerides, and polyglycolized glycerides.

A53. The pharmaceutical composition according to aspect A51 or A52, wherein the spheronizing aid is selected from one or more in the group of crospovidone, carrageenan, chitosan, pectinic acid, glycerides, β-CD, cellulose derivatives, microcrystalline cellulose, powdered cellulose, polyplasdone crospovidone, and polyethylene oxide.

A54. The pharmaceutical composition according to any one of aspects A51 to A53, wherein the water insoluble polymer is selected from one or more in the group of methacrylate polymers, poly(ethyl acrylate, methyl methacrylate, trimethylammonioethyl methacrylate chloride), poly(ethyl acrylate, methyl methacrylate), cellulosic polymers, ethyl cellulose, low-substituted hydroxypropyl cellulose, polyvinyl acetate, polyvinyl pyrrolidone, and polyvinyl acetate blended with polyvinyl pyrrolidone.

A55. The pharmaceutical composition according to any one of aspects A51 to A54, further comprising a lipid release modifier, optionally one or more mono-, di-, and tri-acylglycerols of fatty acids selected from one or more of palmitic acid, tallow acid, stearic acid, oleic acid, linoleic acid, linolenic acid, arachidic acid, behenic acid, and combinations thereof.

A56. The pharmaceutical composition according to aspect A55, wherein the lipid release modifier is selected from one or more mono-, di-, and tri-acylglycerols of fatty acids selected from one or more of palmitic acid, stearic acid, and behenic acid.

A57. The pharmaceutical composition according to aspect A55 or A56, wherein the lipid release modifier has an HLB in a range of 2 to 6.

A58. A spray-congealed lipid vitamin D formulation comprising 25-hydroxyvitamin D, an extended release agent, and a surfactant.

A59. The formulation according to aspect A58, wherein the extended release agent is selected from one or more in the group of paraffin, glycerol monostearate, fatty acid esters of glycerol, fatty acid esters of PEG, blends of fatty acid esters of glycerol and fatty acid esters of PEG, lauroyl macrogolglycerides, lauroyl polyoxylglycerides, blends of lauroyl macrogolglycerides and lauroyl polyoxylglycerides, Gelucire, caprylocaproyl macrogol-8-glyceride, glyceryl distearate, Precirol, glyceryl dibehenate, and Compritol 888.

A60. The formulation according to aspect A58 or A59, wherein the surfactant is selected from one or more in the group of PEG, PEG 4000, Tween and Tween 80.

A61. The formulation according to any one of aspects A58 to A60, having a water content (KF) of less than 0.30 wt. %.

A62. An extruded, spheronized extended release vitamin D formulation, comprising a mixture of about 0.01 to about 0.1 wt. % calcifediol, about 40 wt. % to about 60 wt. % poly(ethyl acrylate, methyl methacrylate, trimethylammonioethyl methacrylate chloride) 1:2:0.2 extended release polymer, about 1 wt. % to about 5 wt. % triglycerides, about 30 wt. % to about 50 wt. % microcrystalline cellulose spheronizing aid, further optionally comprising about 1 wt. % to about 20 wt. % ethylcellulose, and further optionally comprising about 1 wt. % to about 10 wt. % additional binder, optionally low-substituted hydroxypropyl cellulose or methylcellulose, wherein the formulation is free of hydrocarbon waxes and hydrocarbon oils.

A63. An extruded, spheronized extended release vitamin D formulation, comprising a mixture of about 0.01 to about 0.1 wt. % calcifediol, about 1 wt. % to about 10 wt. % ethylcellulose extended release polymer, about 20 wt. % to about 40 wt. % filler, optionally lactose, about 40 wt. % to about 60 wt. % microcrystalline cellulose spheronizing aid, about 1 wt. % to about 15 wt. % triglycerides, further optionally comprising about 1 wt. % to about 10 wt. % ethylcellulose, and further optionally comprising about 1 wt. % to about 15 wt. % additional binder, optionally methylcellulose or low-substituted hydroxypropyl cellulose, wherein the formulation is free of hydrocarbon waxes and hydrocarbon oils.

A64. The formulation of any one of the preceding aspects, having a particle size in a range of about 500 nm to about 2.8 mm.

A65. The formulation of aspect A64, having a particle size in a range of about 250 microns to about 2.8 mm.

A66. The formulation of aspect A65, having a particle size in a range of about 250 microns to about 2 mm.

A67. The formulation of any one of the preceding aspects, characterized by an in vitro dissolution release profile (USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL) of:

less than 20% at 2 hours;
35% to 45% at 4 hours;
55% to 80% at 6 hours;
65% to 85% at 8 hours;
85% to at least 100% at 10 hours; and
90% to at least 100% at 12 hours.

A68. The formulation of any one of the preceding aspects, characterized by an in vitro dissolution release profile (USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL) of:

14% to 18% at 2 hours;
36% to 45% at 4 hours;
55% to 69% at 6 hours;
74% to 88% at 8 hours;
89% to at least 100% at 10 hours; and
97% to at least 100% at 12 hours.

A69. The formulation of any one of the preceding aspects or a dosage form comprising a formulation of any one of the preceding aspects, wherein the formulation or dosage form is free of hydrocarbon waxes, including paraffin.

A70. The formulation of any one of the preceding aspects or a dosage form comprising a formulation of any one of the preceding aspects, wherein the formulation or dosage form is free of hydrocarbon oils, including mineral oil.

A71. A pharmaceutical batch of dosage forms comprising a formulation according to any one of the preceding aspects, characterized by dosage form to dosage form variation in in vitro dissolution release (USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL) at 2, 4, 6, 8, 10, and 12 hour time points less than 15% RSD, or less than 10% RSD, as determined by measurement of six dosage forms.

A72. Pharmaceutical batches of dosage forms comprising a formulation according to any one of the preceding aspects, characterized by batch-to-batch variation in in vitro dissolution release (USP Apparatus II (Paddle with Sinker) at 75 RPM, with a medium of 0.5% SDS in 5 mM Sodium Dihydrogenphosphate Monohydrate, pH 6.8, 37±0.5° C., with a volume of 500 mL) at 2, 4, 6, 8, 10, and 12 hour time points less than 15% RSD, or less than 10% RSD, as determined by measurement of representative dosage forms from six batches.

A73. An oral dosage form comprising a formulation according to any one of the preceding aspects.

A74. The oral dosage form of aspect A73, comprising a formulation according to any one of the previous aspects disposed in a capsule shell, optionally a HPMC shell or hard gelatin shell.

A75. The oral dosage form of aspect A73, comprising a formulation according to any one of the previous aspects disposed in a sachet.

A76. Use of a formulation or dosage form according to any one of aspects A1 to A75 for the manufacture of a medicament for treating a vitamin D responsive disease or condition.

A77. The use according to aspect A76, wherein the medicament is for treating a pediatric patient.

A78. The use according to aspect A76, wherein the medicament is for treating a geriatric patient.

A79. The use according to any one of aspects A76 to A78, wherein the medicament is for administration by a method including sprinkling the formulation onto a substrate prior to orally ingesting the formulation and substrate.

A80. The use according to any one of aspects A76 to A78, wherein the medicament is for administration by a method including dispersing the formulation into a suspension base prior to orally ingesting the formulation and suspension base.

A81. The use according to any one of aspects A76 to A80, wherein the medicament is treating a patient having hyperparathyroidism secondary to Chronic Kidney Disease.

A82. A method for improving batch to batch consistency in an in vitro release profile of an extended release vitamin D compound formulation, comprising compounding the vitamin D compound with a water-insoluble polymer material and optionally one or more additional excipients.

A83. The method of aspect A82, wherein the compounding comprises wet granulation.

A84. The method of aspect A83, wherein the compounding comprises extrusion spheronization.

A85. The method of any one of aspects A82 to A84, wherein the water-insoluble polymer comprises one or more polymers selected from the group of a methacrylic acid polymer and ethylcellulose.

A86. The method of any one of aspects A82 to A85, wherein the one or more additional excipients comprise one or more selected from the group of a diluent, an absorption enhancer, and a binder.

A87. A method of making an extended release pharmaceutical formulation, optionally one according to any one of the preceding formulation aspects, comprising compounding a vitamin D compound with a water-insoluble polymer, and optionally further with at least one pharmaceutically acceptable excipient selected from one or more of a diluent, an absorption enhancer, and a binder.

A88. The method of aspect A87, wherein the water-insoluble polymer material comprises one or more polymers selected from the group of a methacrylic acid polymer and ethylcellulose.

A89. The method of any one of aspects A87 to A88, comprising compounding the vitamin D compound and water-insoluble polymer with a diluent which is selected from one or more in the group of lactose, saccharose, glucose, starch, microcrystalline cellulose, microfine cellulose, mannitol, sorbitol, calcium hydrogen phosphate, aluminum silicate, amorphous silica, and sodium chloride, starch, and dibasic calcium phosphate dihydrate.

A90. The method of any one of aspects A87 to A89 comprising compounding the vitamin D compound and water-insoluble polymer with a diluent which is a pore former.

A91. The method of any one of aspects A87 to A90, comprising compounding the vitamin D compound and water-insoluble polymer with an absorption enhancer which is selected from one or more in the group of triglycerides, medium chain triglycerides, caprylocaproyl macrogolglycerides, and polyglycolized glycerides.

A92. The method of any one of aspects A87 to A91, comprising compounding the vitamin D compound and water-insoluble polymer with a binder which is selected from one or more in the group of low-viscosity, hydrophilic cellulose ethers, PVP, carboxymethyl cellulose, starch, pregelatinized starch, acacia, tragacanth, gelatin, sodium alginate, microcrystalline cellulose, and low-substituted hydroxypropyl cellulose.

A93. The method of aspect A92, wherein the binder is a spheronizing aid, optionally MCC.

A94. The method of any one of aspects A85 to A93, wherein the compounding comprises wet granulation.

A95. The method of any one of aspects A85 to A94, wherein the compounding comprises extrusion and spheronization.

A96. The method of any one of aspects A82 to A95, further comprising omitting hydrocarbon waxes from the formulation, optionally paraffin.

A97. The method of any one of aspects A82 to A96, further comprising omitting hydrocarbon oils from the formulation, optionally mineral oil.

A98. The method of any one of aspects A85 to A97, wherein the spheronized pellet is a spheronized matrix pellet.

A99. The method of any one of aspects A83 to A98, comprising creating a liquid mixture of the vitamin D compound, a solubilized binder, and an absorption enhancer, and applying the liquid mixture to a dry composition comprising the water-insoluble polymer material, with mixing.

A100. A formulation, dosage form, or method as substantially herein described.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A tablet, consisting of:
a mixture of 25-hydroxyvitamin $D_3$, microcrystalline cellulose, starch, magnesium stearate, crospovidone, sucrose, medium chain triglycerides, and silicon dioxide, or
a mixture of 25-hydroxyvitamin D, microcrystalline cellulose, starch, magnesium stearate, crospovidone, sucrose, medium chain triglycerides, silicon dioxide and a disintegrant,
wherein the 25-hydroxyvitamin $D_3$ is the sole active agent in the tablet.

2. The tablet of claim 1, wherein the 25-hydroxyvitamin $D_3$ is present in the tablet in an amount in a range of about 0.01 wt. % to about 0.06 wt. %, based on the total weight of the tablet, based on the total weight of the tablet.

3. The tablet of claim 1, wherein the 25-hydroxyvitamin $D_3$ is in an amount in a range of about 1 µg to about 1 g, or about 10 µg to about 100 µg.

4. The tablet of claim 1, wherein the magnesium stearate is present in the tablet in an amount in a range of about 0.1 wt. % to about 5 wt. %, based on the total weight of the tablet.

5. The tablet of claim 1, wherein the starch is present in the tablet in an amount in a range of about 70 wt. % to about 90 wt. %, based on the total weight of the tablet.

6. The tablet of claim 1, wherein the microcrystalline cellulose is present in the tablet in an amount in a range of about 1 wt % to about 30 wt %, based on the total weight of the tablet.

7. A tablet, consisting of a mixture of 25-hydroxyvitamin $D_3$ and an excipient, the excipient consisting of:
a filler, a disintegrant, a lubricant, and an absorption enhancer, or
a filler, a disintegrant, a lubricant, an absorption enhancer, and a release modifier,
wherein the 25-hydroxyvitamin $D_3$ is present in the tablet in an amount in a range of about 0.01 wt. % to about 0.06 wt. %, based on the total weight of the tablet, and wherein the filler is present in the tablet in an amount of at least 70 wt %, based on the total weight of the tablet, the lubricant is present in the tablet in an amount in a range of about 0.1 wt. % to about 5 wt. %, based on the total weight of the tablet, and the absorption enhancer is present in the tablet in an amount in a range of about 1 wt. % to about 15 wt. %, based on the total weight of the tablet,
wherein the filler is selected from the group consisting of lactose, saccharose, glucose, starch, microcrystalline cellulose, microfine cellulose, mannitol, sorbitol, calcium hydrogen phosphate, aluminum silicate, amorphous silica, sodium chloride, dibasic calcium phosphate dihydrate, crospovidone, carrageenan, chitosan, pectinic acid, glycerides, beta-cyclodextrine, cellulose derivatives, powdered cellulose, polyplasdone crospovidone, polyethylene oxide, and combinations thereof,
wherein the lubricant is selected from the group consisting of stearic acid, magnesium stearate, calcium stearate, aluminum stearate, talc, siliconized talc, and combinations thereof,
wherein the absorption enhancer is selected from the group consisting of capryolcaproyl macrogolglcyerides, triglycerides, and combinations thereof,
wherein the release modifier is a pore former and is a sugar, and
wherein the 25-hydroxyvitamin $D_3$ is the sole active agent in the tablet.

8. The tablet of claim 7, wherein the 25-hydroxyvitamin $D_3$ is present in the tablet in an amount in a range of about 1 µg to about 1 g, or about 10 µg to about 100 µg.

9. The tablet of claim 7, wherein the 25-hydroxyvitamin $D_3$ is present in the tablet in an amount of about 0.03 wt. %.

10. The tablet of claim 7, wherein the filler is starch.

11. The tablet of claim 7, wherein the filler is present in the tablet in an amount in a range of about 70 wt. % to about 90 wt. %, based on the total weight of the tablet.

12. The tablet of claim 7, wherein the filler is crospovidone and microcrystalline cellulose.

13. The tablet of claim 12, wherein the crospovidone and microcrystalline cellulose are in the tablet in an amount in a range of about 1 wt % to about 30 wt %, based on the total weight of the tablet.

14. The tablet of claim 7, wherein the lubricant is magnesium stearate.

15. The tablet of claim 7, wherein the lubricant is in the tablet in an amount in a range of about 0.5 wt. % to about 3 wt. %, based on the total weight of the tablet.

16. The tablet of claim 7, wherein the sugar is lactose and/or sucrose.

17. The tablet of claim 7, wherein the caprylocaproyl macrogolglycerides are polyethylene glycosylated glycerides selected from mixtures of monoglycerides, diglycerides, and triglycerides and monoesters, diesters of polyethylene glycol, polyethylene glycosylated almond glycerides, polyethylene glycosylated corn glycerides, or polyethylene glycosylated caprylic/capric triglyceride.

18. The tablet of claim 7, wherein the absorption enhancer is in the tablet in an amount in a range of about 1 wt. % to about 10 wt. %, based on the total weight of the tablet.

19. The tablet of claim 7, wherein the absorption enhancer is medium chain triglycerides.

20. The tablet of claim 7, wherein the mixture is a spray-dried mixture.

21. The tablet of claim 7, wherein the tablet consists of the 25-hydroxyvitamin $D_3$, microcrystalline cellulose, starch, magnesium stearate, crospovidone, sucrose, medium chain triglycerides, and silicon dioxide.

22. A tablet consisting of a spray-dried 25-hydroxyvitamin $D_3$ composition consisting of a mixture of 25-hydroxyvitamin $D_3$, microcrystalline cellulose, starch, magnesium stearate, crospovidone, sucrose, medium chain triglycerides, and silicon dioxide, wherein the 25-hydroxyvitamin $D_3$ is the sole active agent in the tablet.

23. The tablet of claim 22, wherein the composition is a compressed tablet.

24. The tablet of claim 22, wherein the 25-hydroxyvitamin $D_3$ is present in the tablet in an amount in a range of about 0.01 wt. % to about 0.06 wt. %.

25. A method of treating a vitamin D-responsive disease or condition, a mammal in need of vitamin D supplementation, or a mammal at risk for vitamin D insufficiency or deficiency consisting of administering the tablet according to claim 1 to a mammal in need thereof.

26. The method of claim 25, wherein the mammal is in need of vitamin D supplementation.

27. The method of claim 25, wherein the mammal is at risk for vitamin D insufficiency or deficiency.

28. The method of claim 25, wherein the vitamin D-responsive disease is selected from the group consisting of hyperparathyroidism, hyperparathyroidism secondary to Chronic Kidney Disease ("CKD"), hyperparathyroidism secondary to CKD in mammals undergoing hemodialysis, tertiary hyperparathyroidism, cancer, and autoimmune diseases.

29. The method of claim 28, wherein the autoimmune disease is selected from the group consisting of type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, and combinations thereof.

30. The method of claim 29, wherein the dermatitis is selected from the group consisting of atopic dermatitis, contact dermatitis, allergic dermatitis, chronic dermatitis, and combinations thereof.

* * * * *

UNITED STATES PATENT AND TRADEMARK OFFICE
CERTIFICATE OF CORRECTION

PATENT NO. : 12,133,917 B2
APPLICATION NO. : 17/478395
DATED : November 5, 2024
INVENTOR(S) : Praful Balavant Deshpande et al.

It is certified that error appears in the above-identified patent and that said Letters Patent is hereby corrected as shown below:

In the Claims

At Column 62, Line 42, "beta-cyclodextrine," should be -- beta-cyclodextrin, --.

At Column 62, Lines 51-52, "capryolcaproyl macrogolglcyerides," should be -- caprylocaproyl macrogolglycerides, --.

At Column 64, Lines 28-29, "erythematosis," should be -- erythematosus, --.

Signed and Sealed this
Fourth Day of March, 2025

Coke Morgan Stewart
*Acting Director of the United States Patent and Trademark Office*